(12) United States Patent
Pouliot et al.

(10) Patent No.: US 11,083,196 B2
(45) Date of Patent: Aug. 10, 2021

(54) MICROBIOCIDAL OXADIAZOLE DERIVATIVES

(71) Applicant: SYNGENTA PARTICIPATIONS AG, Basel (CH)

(72) Inventors: Martin Pouliot, Stein (CH); Thomas James Hoffman, Stein (CH); Daniel Stierli, Stein (CH); Renaud Beaudegnies, Stein (CH); Myriem El Qacemi, Stein (CH); Thomas Pitterna, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 84 days.

(21) Appl. No.: 16/087,448

(22) PCT Filed: Mar. 24, 2017

(86) PCT No.: PCT/EP2017/057109
§ 371 (c)(1),
(2) Date: Sep. 21, 2018

(87) PCT Pub. No.: WO2017/162868
PCT Pub. Date: Sep. 28, 2017

(65) Prior Publication Data
US 2019/0387740 A1 Dec. 26, 2019

(30) Foreign Application Priority Data
Mar. 24, 2016 (EP) ..................................... 16162395

(51) Int. Cl.
| A01N 43/82 | (2006.01) |
|---|---|
| A01N 25/28 | (2006.01) |
| C07D 413/10 | (2006.01) |
| C07D 413/14 | (2006.01) |
| C07D 417/10 | (2006.01) |

(52) U.S. Cl.
CPC .............. *A01N 43/82* (2013.01); *A01N 25/28* (2013.01); *C07D 413/10* (2013.01); *C07D 413/14* (2013.01); *C07D 417/10* (2013.01)

(58) Field of Classification Search
CPC .... A01N 43/82; C07D 417/10; C07D 413/14; C07D 413/10
See application file for complete search history.

(56) References Cited

U.S. PATENT DOCUMENTS

2018/0317490 A1* 11/2018 Wiebe .................... A01N 43/82

FOREIGN PATENT DOCUMENTS

| CN | 1927860 A | 3/2007 |
|---|---|---|
| EP | 0276432 A2 | 8/1988 |
| EP | 3165093 A1 | 5/2017 |
| EP | 3165094 A1 | 5/2017 |
| EP | 3187497 A1 | 7/2017 |
| JP | 2017/190296 A | 10/2017 |
| WO | 2005/082898 A1 | 9/2005 |
| WO | 2008/037789 A1 | 4/2008 |
| WO | 2009/133861 A1 | 11/2009 |
| WO | 2010/072602 A1 | 7/2010 |
| WO | 2011/088181 A1 | 7/2011 |
| WO | 2011/088192 A1 | 7/2011 |
| WO | 2012/052490 A1 | 4/2012 |
| WO | 2013/006408 A1 | 1/2013 |
| WO | 2013/008162 A1 | 1/2013 |
| WO | 2013/009810 A1 | 1/2013 |
| WO | 2013/009827 A1 | 1/2013 |
| WO | 2013/009830 A1 | 1/2013 |
| WO | 2013/064079 A1 | 5/2013 |
| WO | 2013/066831 A1 | 5/2013 |
| WO | 2013/066835 A2 | 5/2013 |
| WO | 2013/066839 A2 | 5/2013 |
| WO | 2013/080120 A1 | 6/2013 |
| WO | 2015/055706 A2 | 4/2015 |
| WO | 2015/185485 A1 | 12/2015 |
| WO | 2017/033946 A1 | 3/2017 |
| WO | 2017/076739 A1 | 5/2017 |
| WO | 2017/076740 A1 | 5/2017 |
| WO | 2017/076742 A1 | 5/2017 |
| WO | 2017/076757 A1 | 5/2017 |
| WO | 2017/076935 A1 | 5/2017 |
| WO | 2017/081309 A1 | 5/2017 |
| WO | 2017/081310 A1 | 5/2017 |

(Continued)

OTHER PUBLICATIONS

Hynes J B et al; Hydroxylamine Derivatives as Potential Antimalaria Agents; 3; 1,2,4-Oxadiazoles; Journal of Medicinal Chemistry; American Chemical Society; US; vol. 15, No. 11, Nov. 1, 1972, pp. 1198-1200.

European Search Report for European Patent Application No. 16162395.4 dated May 10, 2016.

International Search Report for International Patent Application No. PCT/EP2017/057109 dated Apr. 26, 2017.

*Primary Examiner* — Amanda L. Aguirre
(74) *Attorney, Agent, or Firm* — Bakerhostetler; Toni-Junell Herbert

(57) ABSTRACT

Compounds of the formula (I) wherein the substituents are as defined in claim 1, useful as a pesticides, especially as fungicides.

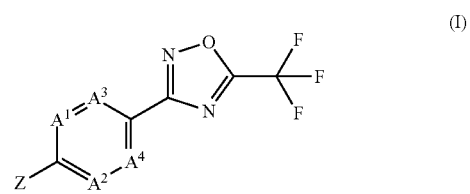

20 Claims, No Drawings

(56) References Cited

FOREIGN PATENT DOCUMENTS

| WO | 2017/081311 A1 | 5/2017 | | |
|----|----|----|----|----|
| WO | 2017/081312 A1 | 5/2017 | | |
| WO | 2017/085098 A1 | 5/2017 | | |
| WO | 2017/085100 A1 | 5/2017 | | |
| WO | 2017/093019 A1 | 6/2017 | | |
| WO | 2017/110861 A1 | 6/2017 | | |
| WO | 2017/110862 A1 | 6/2017 | | |
| WO | 2017/110864 A1 | 6/2017 | | |
| WO | 2017/110865 A1 | 6/2017 | | |
| WO | 2017/111152 A1 | 6/2017 | | |
| WO | 2017/169893 A1 | 10/2017 | | |
| WO | 2017/178245 A1 | 10/2017 | | |
| WO | 2017/211649 A1 | 12/2017 | | |
| WO | 2017/211650 A1 | 12/2017 | | |
| WO | 2017/211652 A1 | 12/2017 | | |
| WO | 2017/213252 A1 | 12/2017 | | |
| WO | 2017/222951 A1 | 12/2017 | | |
| WO | 2018/030460 A1 | 2/2018 | | |
| WO | WO-2018118781 A1 * | 6/2018 | ........... | C07D 413/10 |

\* cited by examiner

MICROBIOCIDAL OXADIAZOLE DERIVATIVES

CROSS-REFERENCE TO RELATED APPLICATIONS

This application is a 371 National Stage application of International Application No. PCT/EP2017/057109, filed Mar. 24, 2017, which claims priority to European Patent Application No. 16162395.4 filed Mar. 24, 2016.

The present invention relates to microbiocidal oxadiazole derivatives, eg, as active ingredients, which have microbiocidal activity, in particular, fungicidal activity. The invention also relates to agrochemical compositions which comprise at least one of the oxadiazole derivatives, to processes of preparation of these compounds and to uses of the oxadiazole derivatives or compositions in agriculture or horticulture for controlling or preventing infestation of plants, harvested food crops, seeds or non-living materials by phytopathogenic microorganisms, preferably fungi.

EP 0 276 432 discloses oxadiazole derivatives with microbiocidal activity.

According to the present invention, there is provided a compound of formula (I):

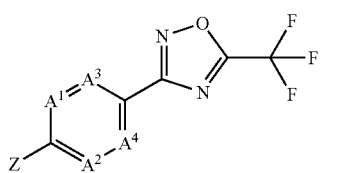

wherein $A^1$ represents N or $CR^1$, wherein $R^1$ represents hydrogen, halogen, methyl, ethyl, difluoromethyl, trifluoromethyl, methoxy, ethoxy or difluoromethoxy;

$A^2$ represents N or $CR^2$, wherein $R^2$ represents hydrogen, halogen, methyl, ethyl, difluoromethyl, trifluoromethyl, methoxy, ethoxy or difluoromethoxy;

$A^3$ represents N or $CR^3$, wherein $R^3$ represents hydrogen or halogen;

$A^4$ represents N or $CR^4$, wherein $R^4$ represents hydrogen or halogen; and wherein 0, 1 or 2 of $A^1$, $A^2$, $A^3$ and $A^4$ are N;

Z is selected from $Z^2$, $Z^2$, $Z^3$, $Z^4$ or $Z^5$; wherein $Z^1$ represents a 5- or 6-membered non-aromatic heterocycle containing 1 ring nitrogen or $NR^5$ group, wherein, optionally: (i) the heterocycle ring further comprises 1 or 2 groups independently selected from N, $NR^5$, C(O) and $S(O)_2$ or 1 group selected from O or S; (ii) the heterocycle ring is 5-membered and further comprises 1 group selected from N, $NR^5$, C(O) and $S(O)_2$ and 1 group selected from O or S; (iii) the heterocycle ring is 6-membered and further comprises 1 or 2 groups independently selected from N, $NR^5$, C(O) and $S(O)_2$ and 1 group selected from O or S; or (iv) the heterocycle ring further comprises 1 group which is C(O) and 2 groups independently selected from N and $NR^5$; and wherein the heterocycle ring is optionally substituted by 1, 2 or 3 substituents, which may be the same or different, selected from $R^9$, or a single substituent selected from $R^{11}$, and wherein the 5- or 6-membered non-aromatic heterocycle is bound to the rest of the molecule by a carbon-carbon bond through a ring carbon;

$Z^2$ represents a 5- or 6-membered non-aromatic heterocycle containing 1 ring nitrogen, wherein optionally: (i) the heterocycle ring further comprises 1 or 2 groups independently selected from C(O) and $S(O)_2$ or 1 group selected from O or S; or (ii) the heterocycle ring further comprises 1 or 2 groups independently selected from C(O) and $S(O)_2$ and 1 group selected from O or S; and wherein when the heterocycle ring is 5-membered it is optionally substituted by 1 or 2 substituents, which may be the same or different, selected from $R^{10}$, or a single substituent selected from $R^{11}$, and wherein when the heterocycle ring is 6-membered it is optionally substituted by 1, 2 or 3 substituents, which may be the same or different, selected from $R^{10}$, or a single substituent selected from $R^{11}$, and wherein a position α to the ring nitrogen is not C(O) or $S(O)_2$, and the heterocycle ring is bound to the rest of the molecule by a nitrogen-carbon bond through the ring nitrogen;

$Z^3$ represents a 5-membered heteroaryl containing 1 ring nitrogen or $NR^5$ group, wherein optionally the heteroaryl ring comprises 1 additional ring atom selected from O, S or N, or 2 additional ring nitrogen atoms, and is optionally substituted by 1, 2 or 3 substituents, which may be the same or different, selected from $R^{12}$, or a single substituent selected from $R^{13}$, and wherein the heteroaryl is bound to the rest of the molecule by a carbon-carbon bond through a ring carbon;

$Z^4$ represents a 6-membered heteroaryl containing 1 ring nitrogen, wherein optionally the heteroaryl ring further comprises 1 or 2 additional ring nitrogen atoms, and is optionally substituted by 1, 2 or 3 substituents, which may be the same or different, selected from $R^{14}$, or a single substituent selected from $R^{15}$, and wherein the heteroaryl is bound to the rest of the molecule by a carbon-carbon bond through a ring carbon; and $Z^5$ represents a 5-membered heteroaryl containing 1 ring nitrogen, wherein optionally the heteroaryl ring further comprises 1 or 2 additional ring nitrogen atoms, and is optionally substituted by 1, 2 or 3 substituents, which may be the same or different, selected from $R^{14}$, and wherein the heteroaryl is bound to the rest of the molecule by a nitrogen-carbon bond through a ring nitrogen;

$R^5$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^6$, $S(O)_2R^6$, $C(O)OR^7$, $C(O)N(R^7)(R^8)$ or $S(O)_2N(R^7)(R^8)$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano;

$R^6$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-2}$alkoxy$C_{1-2}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl, imidazol-1-yl or $C_{3-6}$cycloalkyl;

$R^7$ represents hydrogen, $C_{1-6}$alkyl, $C_{3-6}$cycloalkyl, $C_{3-6}$cycloalkyl$C_{1-2}$alkyl, $C_{1-4}$ alkoxy$C_{1-4}$alkyl, wherein $C_{1-6}$alkyl, $C_{3-6}$cycloalkyl, $C_{3-6}$cycloalkyl$C_{1-2}$alkyl and $C_{1-4}$alkoxy$C_{1-4}$alkyl are optionally substituted by halogen or cyano;

$R^8$ represents hydrogen, $C_{1-4}$alkyl, $C_{1-4}$haloalkyl, $C_{1-4}$alkoxy or $C_{1-4}$alkoxy$C_{1-4}$alkyl;

$R^9$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylsulfinylamino, N—$C_{1-4}$alkylaminocarbonyl, N,N-di$C_{1-4}$alkylaminocarbonyl, N—$C_{1-4}$alkyl-N—$C_{1-4}$alkoxyaminocarbonyl, $C_{3-6}$cycloalkyl, pyridinyl, or phenyl optionally substituted by one or two groups independently selected from fluoro, chloro, methyl or methoxy, or $R^9$ represents —NHC(O)$R^a$, wherein $R^a$ is selected from $C_{1-4}$alkyl, $C_{1-2}$alkoxy$C_{1-2}$alkyl, N,N-di-$C_{1-4}$alkylaminocarbonyl, $C_{3-6}$cycloalkyl, or phenyl optionally substituted by one or two groups independently selected from fluoro, chloro, methyl or methoxy;

$R^{10}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl;

$R^{11}$ represents a three- to six-membered saturated carbocycle which shares a carbon atom of the heterocycle as defined by $Z^1$ or $Z^2$ to form a spirocycle, and wherein optionally the saturated carbocycle further comprises one group selected from O or S;

$R^{12}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, methoxy, ethoxy, iso-propoxy, n-butoxy, sec-butoxy, iso-butoxy, tert-butoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonyloxy$C_{1-4}$alkyl, $C_{1-4}$alkylcarbonylamino, N—$C_{1-4}$alkylaminocarbonyl, N,N-di$C_{1-4}$ alkylaminocarbonyl or $C_{3-6}$cycloalkyl;

$R^{13}$ represents phenyl or pyridinyl, wherein phenyl or pyridinyl are optionally substituted by one or two groups independently selected from fluoro, chloro, methyl, amino or methoxy;

$R^{14}$ represents cyano, amino, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, N—$C_{1-4}$alkylamino, N-cyclopropylamino, N—$C_{1-4}$ alkylaminocarbonyl, N,N-di$C_{1-4}$alkylaminocarbonyl or $C_{3-6}$cycloalkyl, or $R^{14}$ represents —NHC(O)$R^b$, wherein $R^b$ is selected from $C_{1-4}$alkyl, $C_{1-4}$haloalkyl, N—$C_{1-4}$alkylamino, $C_{3-6}$cycloalkyl, or —N[C(O)cyclopropyl]$_2$; and $R^{15}$ represents morpholin-4-yl; or a salt or N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I).

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

As used herein, the term "halogen" or "halo" refers to fluorine, chlorine, bromine or iodine, preferably fluorine, chlorine or bromine.

As used herein, cyano means a —CN group.

As used herein, hydroxy means a —OH group.

As used herein, amino means an —NH$_2$ group.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_{1-4}$alkyl" and "$C_{1-2}$alkyl" are to be construed accordingly. Examples of $C_{1-6}$alkyl include, but are not limited to, methyl, ethyl, n-propyl, 1-methylethyl (iso-propyl), n-butyl, 1-dimethylethyl (f-butyl) and n-pentyl.

As used herein, the term "$C_{3-6}$alkenyl" refers to a straight or branched hydrocarbon chain radical group consisting solely of carbon and hydrogen atoms, containing at least one double bond that can be of either the (E)- or (Z)-configuration, having from three to six carbon atoms, which is attached to the rest of the molecule by a single bond. The term "$C_{2-4}$alkenyl" is to be construed accordingly. Examples of $C_{3-6}$alkenyl and $C_{2-4}$alkenyl include, but are not limited to, allyl, prop-1-enyl, but-1-enyl.

As used herein, the term "$C_{3-6}$alkynyl" refers to a straight or branched hydrocarbon chain radical group consisting solely of carbon and hydrogen atoms, containing at least one triple bond, having from three to six carbon atoms, and which is attached to the rest of the molecule by a single bond. The term "$C_{2-4}$alkynyl" is to be construed accordingly. Examples of $C_{3-6}$alkynyl and $C_{2-4}$alkynyl include, but are not limited to, ethynyl, prop-1-ynyl, but-1-ynyl.

As used herein, the term "$C_{3-6}$cycloalkyl" refers to a stable, monocyclic ring radical which is saturated or partially unsaturated and contains 3 to 6 carbon atoms. Examples of $C_{3-6}$cycloalkyl include, but are not limited to, cyclopropyl, cyclobutyl, cyclopentyl and cyclohexyl.

As used herein, the term "$C_{1-4}$alkoxy" refers to a radical of the formula —OR$^x$ where R$^x$ is a $C_{1-4}$alkyl radical as generally defined above. Examples of $C_{1-4}$alkoxy include, but are not limited to, methoxy, ethoxy, propoxy, iso-propoxy, butoxy.

As used herein, the term "$C_{1-4}$haloalkyl" refers to a $C_{1-4}$alkyl radical as generally defined above substituted by one or more of the same or different halogen atoms. Examples of $C_{1-4}$haloalkyl include, but are not limited to fluoromethyl, difluoromethyl, fluoroethyl, trifluoromethyl, 2,2,2-trifluoroethyl.

As used herein, the term "$C_{2-4}$haloalkenyl" refers to a $C_{2-4}$alkenyl radical as generally defined above substituted by one or more of the same or different halogen atoms.

As used herein, the term "$C_{1-4}$haloalkoxy" refers to a $C_{1-4}$alkoxy radical as generally defined above substituted by one or more of the same or different halogen atoms.

As used herein, the term "$C_{3-4}$alkenoxy" refers to a radical of the formula —OR$^x$ where R$^x$ is a $C_{3-4}$alkenyl radical as generally defined above.

As used herein, the term "$C_{3-4}$alkynyloxy" refers to a radical of the formula —OR$^x$ where R$^x$ is a $C_{3-4}$alkynyl radical as generally defined above.

As used herein, the term "$C_{1-4}$alkylcarbonyl" refers to a radical of the formula —C(O)R$^x$ where R$^x$ is a $C_{1-4}$alkyl radical as generally defined above.

As used herein, the term "$C_{1-4}$alkoxycarbonyl" refers to a radical of the formula —C(O)OR$^x$ where R$^x$ is a $C_{1-4}$alkyl radical as generally defined above.

As used herein, the term "$C_{1-4}$alkylcarbonylamino" refers to a radical of the formula —NHC(O)R$^x$ where R$^x$ is a $C_{1-4}$alkyl radical as generally defined above.

As used herein, the term "N—$C_{1-4}$alkylaminocarbonyl" refers to a radical of the formula —C(O)NHR$^x$ where R$^x$ is a $C_{1-4}$alkyl radical as generally defined above.

As used herein, the term "N,N-di$C_{1-4}$alkylaminocarbonyl" refers to a radical of the formula —C(O)NR$^x$(R$^x$) where each R$^x$ is a $C_{1-4}$alkyl radical as generally defined above.

As used herein, the term "$C_{1-4}$alkoxy$C_{1-4}$alkyl" refers to a $C_{1-4}$alkyl radical as generally defined above substituted by a $C_{1-4}$alkoxy group as defined above. Examples of $C_{1-4}$alkoxy$C_{1-4}$alkyl include, but are not limited to methoxymethyl, 2-methoxyethyl.

As used herein, the term "$C_{1-4}$alkylcarbonyloxy$C_{1-4}$alkyl" refers to a $C_{1-4}$alkyl radical as generally defined above substituted by a radical of formula —OC(O)R$^x$, where R$^x$ is a $C_{1-4}$alkyl radical as generally defined above.

As used herein, the term "$C_{1-4}$alkylsulfinylamino" refers to a radical represented by —NHS(O)R$^x$ wherein R$^x$ is a $C_{1-4}$alkyl as generally defined above.

As used herein, the term "N—$C_{1-4}$alkylamino" refers to a radical represented by —NHR$^x$ wherein R$^x$ is a $C_{1-4}$alkyl as generally defined above.

As used herein, the term "N—$C_{1-4}$alkyl-N—$C_{1-4}$alkoxyaminocarbonyl" refers to a radical represented by —C(O)NR$^x$(OR$^x$) wherein R$^x$ independently of one another are a $C_{1-4}$alkyl as generally defined above.

The presence of one or more possible asymmetric carbon atoms in a compound of formula (I) (eg, in substituent Z) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers (including lactam-lactim tautomerism and keto-enol tautomerism) where present. The present invention includes all possible tautomeric forms for a compound of formula (I).

In each case, the compounds of formula (I) according to the invention are in free form, in covalently hydrated form, in oxidized form as an N-oxide or in salt form, e.g., an agronomically usable or agrochemically acceptable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The following list provides definitions, including preferred definitions, for substituents $A^1$, $A^2$, $A^3$, $A^4$, $R^1$, $R^2$, $R^3$, $R^4$, Z (including Z-1, Z-2, Z-3, Z-4 and Z-5), $R^5$, $R^6$, $R^7$, $R^8$, $R^9$ (including R$^a$), $R^{10}$, $R^{11}$, $R^{12}$, $R^{13}$, $R^{14}$ (including R$^b$) and $R^{15}$ with reference to the compounds of formula (I). For any one of these substituents, any of the definitions given below may be combined with any definition of any other substituent given below or elsewhere in this document.

$A^1$ represents N or CR$^1$, wherein R$^1$ represents hydrogen, halogen, methyl, ethyl, difluoromethyl, trifluoromethyl, methoxy, ethoxy, or difluoromethoxy. In one embodiment of the invention, $A^1$ is CR$^1$. Preferably, R$^1$ represents hydrogen, halogen or methyl. More preferably, R$^1$ represents hydrogen or fluoro. Most preferably, R$^1$ represents hydrogen. In another embodiment of the invention, $A^1$ is N.

$A^2$ represents N or CR$^2$, wherein R$^2$ represents hydrogen, halogen, methyl, ethyl, difluoromethyl, trifluoromethyl, methoxy, ethoxy, or difluoromethoxy. In one embodiment of the invention, $A^2$ is CR$^2$. Preferably, R$^2$ represents hydrogen, halogen or methyl. More preferably, R$^2$ represents hydrogen or fluoro. Most preferably, R$^2$ represents hydrogen. In another embodiment of the invention, $A^2$ is N.

$A^3$ represents N or CR$^3$, wherein R$^3$ represents hydrogen or halogen. In one embodiment of the invention, $A^3$ represents CR$^3$. Preferably, R$^3$ represents hydrogen or fluorine. More preferably, R$^3$ represents hydrogen.

$A^4$ represents N or CR$^4$, wherein R$^4$ represents hydrogen or halogen. In one embodiment of the invention, $A^4$ represents CR$^4$. Preferably, R$^4$ represents hydrogen.

In the compounds of Formula (I) according to the invention, 0, 1 or 2 of $A^1$ to $A^4$ are N. Preferably, 0 or 1 of $A^1$ to $A^4$ are N. More preferably, one of $A^1$ to $A^4$ represents C-halogen and three of $A^1$ to $A^4$ represent C—H, or $A^1$ to $A^4$ represent C—H. Even more preferably, $A^1$ to $A^4$ represent C—H.

Z is selected from $Z^1$, $Z^2$, $Z^3$, $Z^4$ or $Z^5$.

$Z^1$ represents a 5- or 6-membered non-aromatic heterocycle containing 1 ring nitrogen or NR$^5$ group, wherein, optionally: (i) the heterocycle ring further comprises 1 or 2 groups independently selected from N, NR$^5$, C(O) and S(O)$_2$ or 1 group selected from O or S; (ii) the heterocycle ring is 5-membered and further comprises 1 group selected from N, NR$^5$, C(O) and S(O)$_2$ and 1 group selected from O or S; (Hi) the heterocycle ring is 6-membered and further comprises 1 or 2 groups independently selected from N, NR$^5$, C(O) and S(O)$_2$ and 1 group selected from O or S; or (iv) the heterocycle ring further comprises 1 group which is C(O) and 2 groups independently selected from N and NR$^5$; and wherein the heterocycle ring is optionally substituted by 1, 2 or 3 substituents, which may be the same or different, selected from R$^9$, or a single substituent selected from R$^{11}$, and wherein the 5- or 6-membered non-aromatic heterocycle is bound to the rest of the molecule by a carbon-carbon bond through a ring carbon.

Preferably, $Z^1$ is selected from:

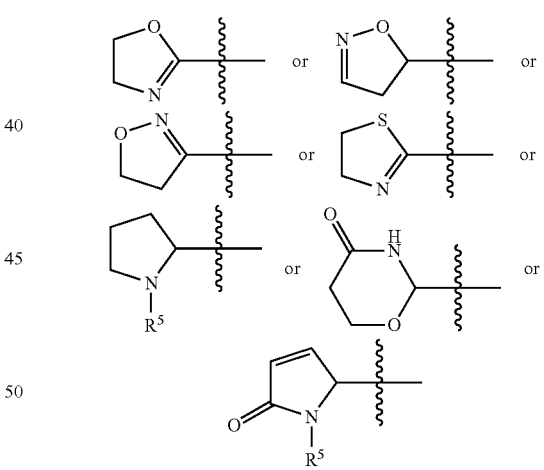

optionally substituted by 1, 2 or 3 substituents, which may be the same or different, selected from R$^9$, or a single substituent selected from R$^{11}$.

In one embodiment of the invention, $Z^1$ is a 5-membered heterocycle containing 1 ring nitrogen, wherein the heterocycle ring further comprises an oxygen or sulfur atom, and wherein the heterocycle ring is optionally substituted by 1, 2 or 3 substituents, which may be the same or different, selected from R$^9$, wherein R$^9$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylsulfinylamino, N—$C_{1-4}$ alkylaminocarbonyl, N,N-di$C_{1-4}$alkylaminocarbonyl, N—$C_{1-4}$alkyl-N—$C_{1-4}$alkoxyaminocarbonyl, $C_{3-6}$cycloalkyl, pyridinyl, or phenyl optionally substituted by one or two groups independently selected from fluoro, chloro, methyl or methoxy, or $R^9$ represents —NHC(O)$R^a$, wherein $R^a$ is selected from $C_{1-4}$alkyl, $C_{1-2}$alkoxy$C_{1-2}$alkyl, N,N-di-$C_{1-4}$ alkylaminocarbonyl, $C_{3-6}$cycloalkyl, or phenyl optionally substituted by one or two groups independently selected from fluoro, chloro, methyl or methoxy. Preferably, $R^9$ is selected from cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl, or $R^9$ represents —NHC(O)$R^a$, wherein $R^a$ is selected from $C_{1-4}$alkyl, $C_{1-2}$alkoxy$C_{1-2}$alkyl, N,N-di-$C_{1-2}$alkylaminocarbonyl, $C_{3-4}$cycloalkyl, or phenyl optionally substituted by one or two groups independently selected from fluoro, chloro, methyl or methoxy. More preferably, $R^9$ is selected from halogen, $C_{1-4}$alkyl, $C_{1-4}$haloalkyl, $C_{1-4}$alkoxy, $C_{1-2}$alkoxy$C_{1-2}$alkyl, $C_{1-4}$haloalkoxy, $C_{1-4}$alkoxycarbonyl, or $C_{3-4}$cycloalkyl, or $R^9$ is selected from —NHC(O)$R^a$, wherein $R^a$ is selected from $C_{1-4}$alkyl, $C_{1-2}$alkoxy$C_{1-2}$alkyl, N,N-di-$C_{1-2}$alkylaminocarbonyl, $C_{3-4}$cycloalkyl, or phenyl optionally substituted by one group selected from fluoro, chloro, methyl or methoxy.

Preferably, in this embodiment, $Z^1$ is:

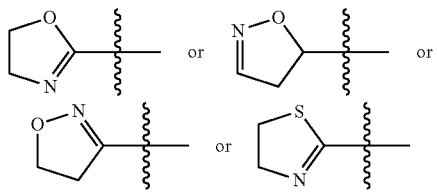

and is optionally substituted by 1, 2 or 3 substituents, which may be the same or different, selected from $R^9$, wherein $R^9$ is cyano, halogen, hydroxy, $C_{1-4}$alkyl, $C_{1-4}$haloalkyl, $C_{1-4}$alkoxy, $C_{1-4}$alkoxy$C_{1-4}$alkyl, $C_{1-4}$haloalkoxy, $C_{1-4}$alkylcarbonyl, $C_{1-4}$alkoxycarbonyl, or $C_{3-6}$cycloalkyl; or more preferably is optionally substituted by 1 or 2 substituents, which may be the same or different, selected from $R^9$, wherein $R^9$ is halogen, $C_{1-4}$alkyl, $C_{1-4}$haloalkyl, $C_{1-4}$alkoxy, $C_{1-4}$alkoxy$C_{1-4}$alkyl, $C_{1-4}$haloalkoxy, $C_{1-4}$alkoxycarbonyl, or $C_{3-6}$cycloalkyl; or even more preferably, is optionally substituted by 1 or 2 substituents, which may be the same or different, selected from $R^9$, wherein $R^9$ is fluoro, chloro, bromo, methyl, ethyl, n-propyl, trifluoromethyl, methoxycarbonyl, methoxymethyl, methoxy, ethoxy, 2,2,2-trifluoroethoxy, cyclopropyl or cyclohexyl.

In one embodiment of the invention, $Z^1$ is a 6-membered heterocycle containing 1 ring nitrogen, wherein the heterocycle ring further comprises a C(O) and an O, and wherein the heterocycle ring is optionally substituted by 1, 2 or 3 substituents, which may be the same or different, selected from $R^9$, wherein $R^9$ is cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl.

Preferably, in this embodiment, $Z^1$ is:

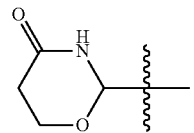

and is optionally substituted by 1, 2 or 3 substituents, which may be the same or different, selected from $R^9$, wherein $R^9$ is fluoro, chloro, bromo, methyl, ethyl, n-propyl, trifluoromethyl, methoxy, or ethoxy; or more preferably is optionally substituted by 1, 2 or 3 substituents, which may be the same or different, selected from $R^9$, wherein $R^9$ is methyl, ethyl, trifluoromethyl, or methoxy.

In some embodiments of the invention, $Z^1$ preferably represents a 5- or 6-membered non-aromatic heterocycle containing 1 ring nitrogen, wherein, optionally: (i) the heterocycle ring further comprises 1 or 2 groups independently selected from N, $NR^5$ and C(O), or 1 group which is $S(O)_2$, or 1 group selected from O or S; (ii) the heterocycle ring is 5-membered and further comprises 1 group selected from N, $NR^5$, C(O) and $S(O)_2$ and 1 group selected from O or S; (iii) the heterocycle ring is 6-membered and further comprises, 1 or 2 groups independently selected from N, $NR^5$ and C(O) or 1 group which is $S(O)_2$, and 1 group selected from O or S; or (iv) the heterocycle ring further comprises 1 group which is C(O) and 2 groups independently selected from N and $NR^5$; and wherein the heterocycle ring is optionally substituted by 1, 2 or 3 substituents, which may be the same or different, selected from $R^9$, or a single substituent selected from $R^{11}$, and wherein the 5- or 6-membered non-aromatic heterocycle is bound to the rest of the molecule by a carbon-carbon bond through a ring carbon.

$Z^2$ represents a 5- or 6-membered non-aromatic heterocycle containing 1 ring nitrogen, wherein optionally: (i) the heterocycle ring further comprises 1 or 2 groups independently selected from C(O) and $S(O)_2$ or 1 group selected from O or S; or (ii) the heterocycle ring further comprises 1 or 2 groups independently selected from C(O) and $S(O)_2$ and 1 group selected from O or S; and wherein when the heterocycle ring is 5-membered it is optionally substituted by 1 or 2 substituents, which may be the same or different, selected from $R^{10}$, or a single substituent selected from $R^{11}$, and wherein when the heterocycle ring is 6-membered it is optionally substituted by 1, 2 or 3 substituents, which may be the same or different, selected from $R^{10}$, or a single substituent selected from $R^{11}$, and wherein a position α to the ring nitrogen is not C(O) or $S(O)_2$, and the heterocycle ring is bound to the rest of the molecule by a nitrogen-carbon bond through the ring nitrogen.

In some embodiments of the invention, $Z^2$ represents a 5- or 6-membered non-aromatic heterocycle containing 1 ring nitrogen, wherein optionally: (i) the heterocycle ring further comprises 1 or 2 groups which is C(O) or 1 group which is $S(O)_2$ or 1 group selected from O or S; or (ii) the heterocycle ring further comprises 1 or 2 groups which is C(O) or 1 group which is $S(O)_2$, and 1 group selected from O or S; and wherein when the heterocycle ring is 5-membered it is optionally substituted by 1 or 2 substituents, which may be the same or different, selected from $R^{10}$, or a single substituent selected from $R^{11}$, and wherein when the heterocycle ring is 6-membered it is optionally substituted by 1, 2 or 3 substituents, which may be the same or different, selected from $R^{10}$, or a single substituent selected from $R^{11}$, wherein a position α to the ring nitrogen is not C(O) or S(O)$_2$, and the heterocycle ring is bound to the rest of the molecule by a nitrogen-carbon bond through the ring nitrogen;

When Z is Z$^2$, a position a to the ring nitrogen bound to the rest of the molecule (ie, contiguous/adjacent) may not be a C(O) or S(O)$_2$ group. This exclusion may be generally represented in a compound of Formula (I) comprising a Z$^2$ fragment, as follows:

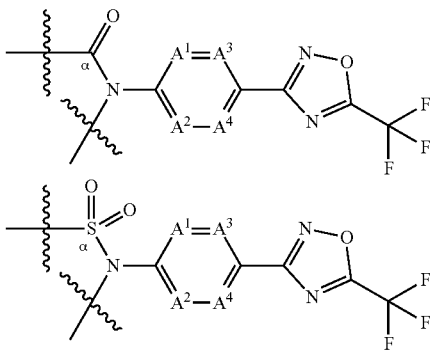

In accordance with the definitions of Z$^1$ and Z$^2$, it is preferable that when the heterocycle ring contains an S(O)$_2$ group, that an adjacent ring atom is not sulfur, ie, an S group or an S(O)$_2$ group.

Z$^3$ represents a 5-membered heteroaryl containing 1 ring nitrogen or NR$^5$ group, wherein optionally the heteroaryl ring comprises 1 additional ring atom selected from O, S or N, or 2 additional ring nitrogen atoms, and is optionally substituted by 1, 2 or 3 substituents, which may be the same or different, selected from R$^{12}$, or a single substituent selected from R$^{13}$, and wherein the heteroaryl is bound to the rest of the molecule by a carbon-carbon bond through a ring carbon.

In one embodiment of the invention, Z$^3$ is a 5-membered heteroaryl containing 1 ring nitrogen, wherein the heteroaryl ring further comprises an oxygen atom or a sulfur atom, and wherein the heteroaryl ring is optionally substituted by 1 or 2 substituents, which may be the same or different, selected from R$^{12}$, wherein R$^{12}$ is cyano, halogen, hydroxy, C$_{1-4}$alkyl, C$_{2-4}$alkenyl, C$_{2-4}$alkynyl, C$_{1-4}$haloalkyl, C$_{2-4}$haloalkenyl, methoxy, ethoxy, iso-propoxy, n-butoxy, sec-butoxy, iso-butoxy, tert-butoxy, C$_{1-4}$alkoxyC$_{1-4}$alkyl, C$_{1-4}$haloalkoxy, C$_{3-4}$alkenyloxy, C$_{3-4}$alkynyloxy, C$_{1-4}$alkylcarbonyl, C$_{1-4}$alkoxycarbonyl, C$_{1-4}$alkylcarbonyloxyC$_{1-4}$alkyl, C$_{1-4}$alkylcarbonylamino, N—C$_{1-4}$alkylaminocarbonyl, N,N-diC$_{1-4}$alkylaminocarbonyl or C$_{3-6}$cycloalkyl, or the heteroaryl ring is optionally substituted by 1 substituent selected from R$^{13}$, wherein R$^{13}$ represents phenyl or pyridinyl, wherein phenyl or pyridinyl are optionally substituted by one or two groups independently selected from fluoro, chloro, methyl, amino or methoxy.

Preferably, in this embodiment, wherein Z$^3$ is a heteroaryl selected from:

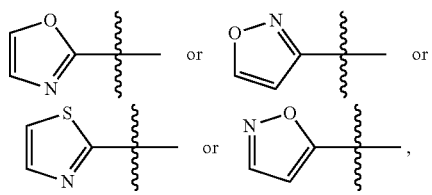

and is optionally substituted by 1 or 2 substituents, which may be the same or different, selected from R$^{12}$, wherein R$^{12}$ is C$_{1-4}$alkyl, C$_{1-4}$haloalkyl, methoxy, ethoxy, iso-propoxy, n-butoxy, sec-butoxy, iso-butoxy, tert-butoxy, C$_{1-4}$alkoxy C$_{1-4}$alkyl, C$_{1-4}$haloalkoxy, C$_{1-4}$alkylcarbonyl, C$_{1-4}$alkoxycarbonyl, C$_{1-4}$alkylcarbonyloxyC$_{1-4}$alkyl or C$_{3-6}$cycloalkyl, or a single substituent selected from R$^{13}$ which is phenyl or pyridinyl; or preferably, is optionally substituted by 1 or 2 substituents, which may be the same or different, selected from R$^{12}$, wherein R$^{12}$ is C$_{1-4}$alkyl, C$_{1-4}$haloalkyl, C$_{1-4}$alkoxyC$_{1-4}$alkyl, C$_{1-4}$alkoxycarbonyl, C$_{1-4}$alkylcarbonyloxyC$_{1-4}$alkyl, or C$_{3-6}$cycloalkyl, or the heteroaryl ring is optionally substituted by 1 substituent selected from R$^{13}$, wherein R$^{13}$ is phenyl or pyridinyl.

In another embodiment of the invention, Z$^3$ is a 5-membered heteroaryl which is a pyrazolyl group, wherein the pyrazolyl group is optionally substituted by 1 or 2 substituents, which may be the same or different, selected from R$^{12}$, or preferably, is optionally substituted by 1 or 2 substituents, which may be the same or different, selected from R$^{12}$, wherein R$^{12}$ is methyl, ethyl, n-propyl, trifluoromethyl, methoxy, ethoxy, or difluoromethoxy. Preferably, in this embodiment, R$^{12}$ is methyl, ethyl, trifluoromethyl, or methoxy.

In another embodiment of the invention, Z$^3$ is a 5-membered heteroaryl which is a triazolyl group, wherein the triazolyl group is optionally substituted by 1 substituent selected from R$^{12}$, or preferably, is optionally substituted by 1 substituent selected from R$^{12}$, wherein R$^{12}$ is methyl, ethyl, n-propyl, trifluoromethyl, methoxy, ethoxy, or difluoromethoxy. Preferably, in this embodiment, R$^{12}$ is methyl, ethyl, trifluoromethyl, or methoxy.

Z$^4$ represents a 6-membered heteroaryl containing 1 ring nitrogen, wherein optionally the heteroaryl ring further comprises 1 or 2 additional ring nitrogen atoms, and is optionally substituted by 1, 2 or 3 substituents, which may be the same or different, selected from R$^{14}$, or a single substituent selected from R$^{15}$, and wherein the heteroaryl is bound to the rest of the molecule by a carbon-carbon bond through a ring carbon.

In one embodiment of the invention, Z$^4$ is a pyridin-2-yl, pyridin-3-yl, pyridin-4-yl, pyrimidin-2-yl, pyrimidin-4-yl or pyrimidin-5-yl group (and preferably pyridin-2-yl, pyridin-3-yl or pyridin-4-yl) optionally substituted by 1, 2 or 3 substituents, which may be the same or different, selected from R$^{14}$ or a single substituent represented by R$^{15}$. In particular, R$^{14}$ may be selected from cyano, amino, halogen, hydroxy, C$_{1-4}$alkyl, C$_{1-4}$alkoxy, or —NHC(O)R$^b$, wherein R$^b$ is selected from C$_{1-4}$alkyl, C$_{1-4}$haloalkyl, N—C$_{1-4}$alkylamino, C$_{3-6}$cycloalkyl, or —N[C(O)cyclopropyl]$_2$. Preferably, R$^{14}$ may be selected from cyano, amino, halogen, hydroxy, C$_{1-4}$alkyl, C$_{1-4}$alkoxy, or —NHC(O)R$^b$, wherein R$^b$ is selected from C$_{1-4}$alkyl, C$_{1-2}$haloalkyl, N—C$_{1-2}$alkylamino, C$_{3-4}$cycloalkyl, or —N[C(O)cyclopropyl]$_2$. More preferably, R$^{14}$ is selected from fluoro, chloro, bromo, methyl, ethyl, n-propyl, trifluoromethyl, methoxy and ethoxy.

Z$^5$ represents a 5-membered heteroaryl containing 1 ring nitrogen, wherein optionally the heteroaryl ring further comprises 1 or 2 additional ring nitrogen atoms, and is optionally substituted by 1, 2 or 3 substituents, which may be the same or different, selected from R$^{14}$, and wherein the heteroaryl is bound to the rest of the molecule by a nitrogen-carbon bond through a ring nitrogen.

In one embodiment of the invention, Z$^5$ is a pyrazolyl group, wherein the pyrazolyl group is optionally substituted by 1 or 2 substituents, which may be the same or different, selected from R¹⁴, wherein R¹⁴ is fluoro, chloro, bromo, methyl, ethyl, n-propyl, trifluoromethyl, methoxy, ethoxy, or difluoromethoxy. Preferably, in this embodiment, R¹⁴ is fluoro, chloro, methyl, ethyl, methoxy.

In another embodiment of the invention, $Z^5$ is a triazolyl group, wherein the triazolyl group is optionally substituted by 1 substituent selected from R¹⁴, wherein R¹⁴ is methyl, ethyl, n-propyl, trifluoromethyl, methoxy, ethoxy, or difluoromethoxy. Preferably, in this embodiment, R¹⁴ is methyl, ethyl, trifluoromethyl, or methoxy.

$R^5$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^6$, $S(O)_2R^6$, $C(O)OR^7$, $C(O)N(R^7)(R^8)$ or $S(O)_2N(R^7)(R^8)$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano. Preferably, $R^5$ represents hydrogen, $C(O)R^6$, $S(O)_2R^6$, $C(O)OR^7$ or $C(O)N(R^7)(R^8)$, wherein $R^6$ is selected from $C_{1-4}$alkyl, $C_{1-2}$alkoxyC_{1-2}alkyl, imidazol-1-yl or $C_{3-6}$cycloalkyl; $R^7$ is selected from hydrogen or $C_{1-4}$alkyl; and $R^8$ represents hydrogen, $C_{1-4}$alkyl or $C_{1-4}$alkoxy.

$R^6$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-2}$alkoxyC_{1-2}alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl, imidazol-1-yl or $C_{3-6}$cycloalkyl.

$R^7$ represents hydrogen, $C_{1-6}$alkyl, $C_{3-6}$cycloalkyl, $C_{3-6}$cycloalkylC_{1-2}alkyl, $C_{1-4}$ alkoxyC_{1-4}alkyl, wherein $C_{1-6}$alkyl, $C_{3-6}$cycloalkyl, $C_{3-6}$cycloalkylC_{1-2}alkyl and $C_{1-4}$alkoxyC_{1-4}alkyl are optionally substituted by halogen or cyano.

$R^8$ represents hydrogen, $C_{1-4}$alkyl, $C_{1-4}$haloalkyl, $C_{1-4}$alkoxy or $C_{1-4}$alkoxyC_{1-4}alkyl.

$R^9$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxyC_{1-4}alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylsulfinylamino, N—$C_{1-4}$alkylaminocarbonyl, N,N-di$C_{1-4}$alkylaminocarbonyl, N—$C_{1-4}$alkyl-N—$C_{1-4}$alkoxyaminocarbonyl, $C_{3-6}$cycloalkyl, pyridinyl, or phenyl optionally substituted by one or two groups independently selected from fluoro, chloro, methyl or methoxy, or $R^9$ represents —$NHC(O)R^a$, wherein $R^a$ is selected from $C_{1-4}$alkyl, $C_{1-2}$alkoxyC_{1-2}alkyl, N,N-di-$C_{1-4}$alkylaminocarbonyl, $C_{3-6}$cycloalkyl, or phenyl optionally substituted by one or two groups independently selected from fluoro, chloro, methyl or methoxy.

$R^{10}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxyC_{1-4}alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl.

$R^{11}$ represents a three- to six-membered saturated carbocycle which shares a carbon atom of the heterocycle as defined by $Z^1$ or $Z^2$ to form a spirocycle, and wherein optionally the saturated carbocycle further comprises one group selected from O or S.

$R^{12}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, methoxy, ethoxy, iso-propoxy, n-butoxy, sec-butoxy, isobutoxy, tert-butoxy, $C_{1-4}$alkoxyC_{1-4}alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkoxycarbonyloxyC_{1-4}alkyl, $C_{1-4}$alkylcarbonylamino, N—$C_{1-4}$alkylaminocarbonyl, N,N-di$C_{1-4}$alkylaminocarbonyl or $C_{3-6}$cycloalkyl.

$R^{13}$ represents phenyl or pyridinyl, wherein phenyl or pyridinyl are optionally substituted by one or two groups independently selected from fluoro, chloro, methyl, amino or methoxy.

$R^{14}$ represents cyano, amino, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxyC_{1-4}alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylamino, N-cyclopropylamino, N—$C_{1-4}$alkylaminocarbonyl, N,N-di$C_{1-4}$alkylaminocarbonyl or $C_{3-6}$cycloalkyl, or $R^{14}$ represents —$NHC(O)R^b$, wherein $R^b$ is selected from $C_{1-4}$alkyl, $C_{1-4}$haloalkyl, N—$C_{1-4}$alkylamino, $C_{3-6}$cycloalkyl, or —$N[C(O)cyclopropyl]_2$.

$R^{15}$ represents morpholin-4-yl.

In embodiments of the compounds of Formula (I) according to the invention:

Preferably, one of $A^1$ to $A^4$ represents C-halogen, and three of $A^1$ to $A^4$ represent C—H, or $A^1$ to $A^4$ represent C—H;

Z is $Z^1$, where $Z^1$ is selected from:

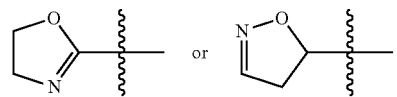 [SMILES: *C1=NCCO1 ; *C1CC=NO1]

optionally substituted by 1, 2 or 3 substituents, which may be the same or different, selected from $R^9$, and $R^9$ is cyano, halogen, hydroxy, $C_{1-4}$alkyl, $C_{1-4}$haloalkyl, $C_{1-4}$alkoxy, $C_{1-4}$alkoxyC_{1-4}alkyl, $C_{1-4}$haloalkoxy, $C_{1-4}$alkylcarbonyl, $C_{1-4}$alkoxycarbonyl, or $C_{3-6}$cycloalkyl.

More preferably, $A^1$ to $A^4$ represent C—H;

Z is $Z^1$, where $Z^1$ is selected from:

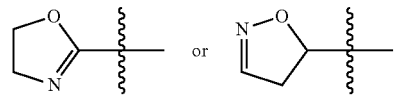 [SMILES: *C1=NCCO1 ; *C1CC=NO1]

optionally substituted by 1 or 2 substituents, which may be the same or different, selected from $R^9$; and $R^9$ is fluoro, chloro, bromo, methyl, ethyl, n-propyl, trifluoromethyl, methoxycarbonyl, methoxymethyl, methoxy, ethoxy, 2,2,2-trifluoroethoxy, cyclopropyl or cyclohexyl.

Preferably, one of $A^1$ to $A^4$ represents C-halogen, and three of $A^1$ to $A^4$ represent C—H, or $A^1$ to $A^4$ represent C—H;

Z is $Z^1$, wherein $Z^1$ is:

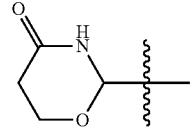 [SMILES: *C1NC(=O)CCO1]

optionally substituted by 1, 2 or 3 substituents, which may be the same or different, selected from $R^9$;

$R^9$ is fluoro, chloro, bromo, methyl, ethyl, n-propyl, trifluoromethyl, methoxy, ethoxy, or trifluoromethoxy.

Preferably, one of $A^1$ to $A^4$ represents C-halogen, and three of $A^1$ to $A^4$ represent C—H, or $A^1$ to $A^4$ represent C—H;

Z is $Z^3$, wherein $Z^3$ is:

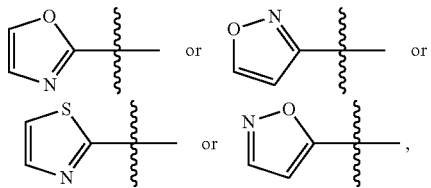

optionally substituted by 1 or 2 substituents, which may be the same or different, selected from $R^{12}$; and $R^{12}$ is $C_{1-4}$alkyl, $C_{1-4}$haloalkyl, methoxy, ethoxy, iso-propoxy, n-butoxy, sec-butoxy, iso-butoxy, tert-butoxy, $C_{1-4}$alkoxy$C_{1-4}$alkyl, $C_{1-4}$haloalkoxy, $C_{1-4}$alkylcarbonyl, $C_{1-4}$alkoxycarbonyl, $C_{1-4}$alkylcarbonyloxy$C_{1-4}$alkyl, or $C_{3-6}$cycloalkyl.

It is understood that when in aqueous media, the compounds of formula (I) according to the invention may be present in a reversible equilibrium with the corresponding covalently hydrated forms (ie, the compounds of formula (I-I) and formula (I-II) as shown below, which may also exist in tautomeric form as the compounds of formula (I-Ia) and formula (I-IIa)) at the $CF_3$-oxadiazole motif. This dynamic equilibrium may be important for the biological activity of the compounds of Formula (I). The designations of $A^1$, $A^2$, $A^3$, $A^4$, $R^1$, $R^2$, $R^3$, $R^4$, Z (including Z-1, Z-2, Z-3, Z-4 and Z-5), $R^5$, $R^6$, $R^7$, $R^8$, $R^9$ (including $R^a$), $R^{10}$, $R^{11}$, $R^{12}$, $R^{13}$, $R^{14}$ (including $R^b$) and $R^{15}$, with reference to the compounds of formula (I) of the present invention apply generally to the compounds of Formulae (I-I) and (I-Ia), and Formulae (I-II) and (I-IIa), as do the specific disclosures of combinations of $A^1$, $A^2$, $A^3$, $A^4$, $R^1$, $R^2$, $R^3$, $R^4$, Z (including Z-1, Z-2, Z-3, Z-4 and Z-5), $R^5$, $R^6$, $R^7$, $R^8$, $R^9$ (including $R^a$), $R^{10}$, $R^{11}$, $R^{12}$, $R^{13}$, $R^{14}$ (including $R^b$) and $R^{15}$ for the compounds as represented in Tables 2 to 10 (below) or Tables 2a to 7a (below) or in Table A (entries A-1 to A-51), Table B (entry B-1), Table C (entries C-1 to C-14), Table D (entries D-1 to D-27) and Table E (entry E-1) (below).

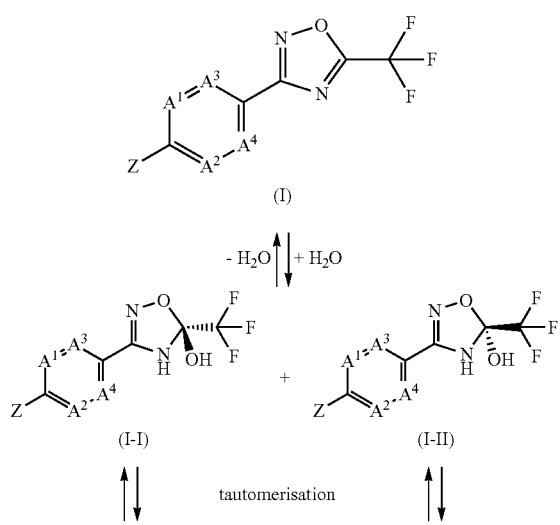

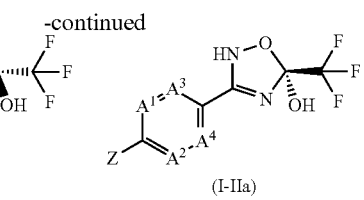

Compounds of the present invention can be made as shown in the following schemes 1 to 17, in which, unless otherwise stated, the definition of each variable is as defined above for a compound of formula (I).

Compounds of formula (Ia), wherein $R^z$ represents suitable definitions for $R^9$, $R^{11}$, and $R^{12}$, and wherein Q is S, O, or $NR^5$, can be prepared from compounds of formula (Ib) via treatment with an oxidant (e.g. $MnO_2$ or 2,3-dichloro-5,6-dicyano-1,4-benzoquinone (DDQ)) in a suitable solvent (e.g. chloroform or dichloromethane) at a temperature between 25° C. and reflux. For related examples, see Martin, P. K. et al J. Org. Chem. 1968, 33, 3758 and Barrish, J. C. et al *J. Org. Chem.* 1993, 58, 4494. This reaction is shown in Scheme 1.

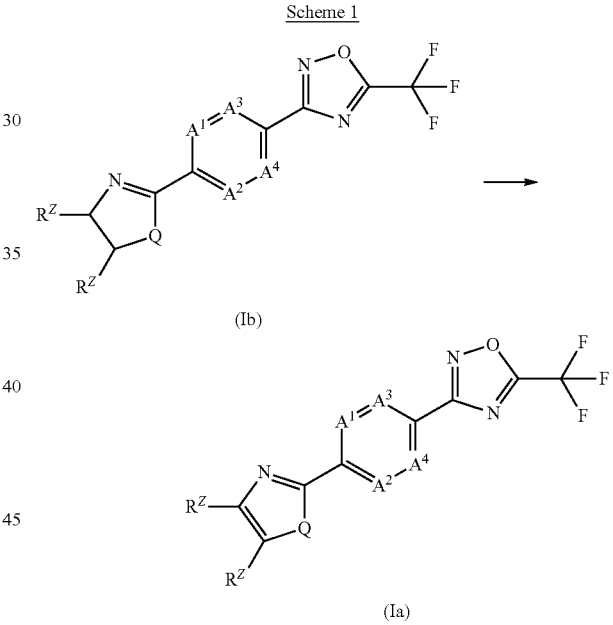

Compounds of formula (Ic), wherein $R^z$ represents suitable definitions for $R^9$ and $R^{11}$, can be obtained by an amide coupling transformation with compounds of formula (II) and compounds of formula (III) by activating the carboxylic acid function of the compounds of formula (II), a process that usually takes place by converting the —OH of the carboxylic acid into a good leaving group, such as a chloride group, for example by using $(COCl)_2$ or $SOCl_2$, prior to treatment with the compounds of formula (III), preferably in a suitable solvent (e.g., dimethylformamide, dichloromethane or tetrahydrofuran), preferably at a temperature of between 25° C. and 100° C., and optionally in the presence of a base such as triethyl amine or N,N-diisopropylethylamine, or under conditions described in the literature for an amide coupling. For examples, see Valeur, E.; Bradley, M. *Chem. Soc. Rev.* (2009), 38, 606 and Chinchilla, R., Najera, C. *Chem. Soc. Rev.* (2011), 40, 5084. This is followed by the cyclodehydration of an intermediated hydroxyl amide species upon the introduction of diethylaminosulfur trifluoride (DAST) or bis(2-methoxyethyl)aminosulfur trifluoride (Deoxyfluor). For examples, see Williams, D. R. et al *Org. Lett.* 2000, 2, 1165. Compounds of formula (II) can be made by known methods from known compounds or are commercially available. For examples, see: Liu, K. et al. *J. Med. Chem.* (2008), 51, 7843 and WO 2013/008162 A1. Compounds of formula (III) are commercially available. This reaction is shown in Scheme 2 below.

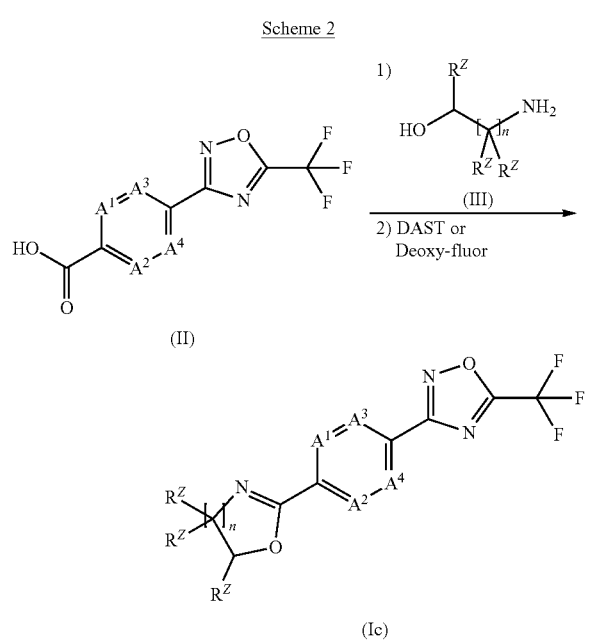

Compounds of formula (Id), wherein $R^z$ and —$CH_2R^{Z'}$ are within the definitions of $R^{12}$, can be obtained by an amide coupling transformation with compounds of formula (II) and compounds of formula (IV) by activating the carboxylic acid function of the compounds of formula (II), a process that usually takes place by converting the —OH of the carboxylic acid into a good leaving group, such as a chloride group, for example by using (COCl)$_2$ or SOCl$_2$, prior to treatment with the compounds of formula (IV), preferably in a suitable solvent (eg, dimethylformamide, dichloromethane or tetrahydrofuran), preferably at a temperature of between 25° C. and 100° C., and optionally in the presence of a base such as triethyl amine or N,N-diisopropylethylamine, or under conditions described in the literature for an amide coupling. For examples, see Valeur, E.; Bradley, M. *Chem. Soc. Rev.* (2009), 38, 606 and Chinchilla, R., Najera, C. *Chem. Soc. Rev.* (2011), 40, 5084. This is followed by the cycloisomerization of the intermediate alkynyl amide species upon the introduction of an acid (e.g., SiO$_2$ or p-tolylsulfonic acid). For examples, see: Wipf, P. et al *J. Org. Chem.* 1998, 63, 7132 and Wipf, P. et al *Org. Lett.* 2004, 6, 3593. Compounds of formula (IV) are commercially available. This reaction is shown in Scheme 3 below.

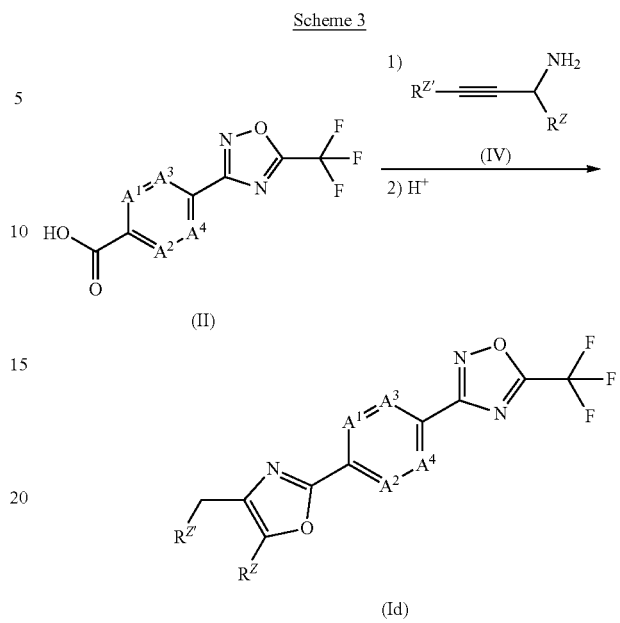

Compounds of formula (Ie), wherein $R^z$ is within the definitions of $R^{12}$, can be obtained via a Hantzsch-type cyclization using compounds of formula (V) and compounds of formula (VI) wherein X is chloro or bromo, a process that usually takes place by in the presence of a base (e.g., Et$_3$N or K$_2$CO$_3$) in a suitable solvent (eg, methanol or dichloromethane), at a temperature between 25° C. and reflux. In some cases, an enhanced reaction performance may be achieved using microwaves irradiation. For examples, see Reck, S. et al *Heterocycles* 1998, 48, 853. Bredenkamp, M. W. et al *Synth. Comm.* 1990, 20, 2235. Compounds of formula (VI) are either commercially available or are known compounds.

Alternatively, aromatic compounds of formula (If), wherein $R^z$ and —$CH_2R^{Z'}$ are within the definitions of $R^{12}$, can be obtained via the same transformation protocol and involves alkyne compounds of formula (VII) wherein X is chloro or bromo. For examples, see: Castagnolo, D. *Synlett* 2009, 2093.

Non-aromatic heterocyclic compounds of formula (Im) can be obtained from compounds of the formula (V) by reaction with a compound (Io), wherein LG is a leaving group, eg, a tosylate or a halogen, such as chlorine or bromine. This transformation can be done between –20° C. and 150° C., and preferably at ambient temperature. It can be done in the presence of a base, such as potassium carbonate, or potassium bicarbonate, and in the presence of a salt, such as an iodide, preferably potassium iodide. Compounds of the formula (In), wherein $R^{Z''}$ is H can be made from compounds of the formula (Im) by deprotection, for instance with acid, such as hydrochloric acid. Compounds of the formula (In), wherein NH—$R^{Z''}$ is within the scope of $R^9$ can be made from compounds of the formula (Im) by deprotection, followed by coupling of the intermediate compound of the formula (In), wherein $R^{Z''}$ is H, for example with a carboxylic acid or an acid chloride by known methods. These reactions are shown in Scheme 4 below.

Scheme 4

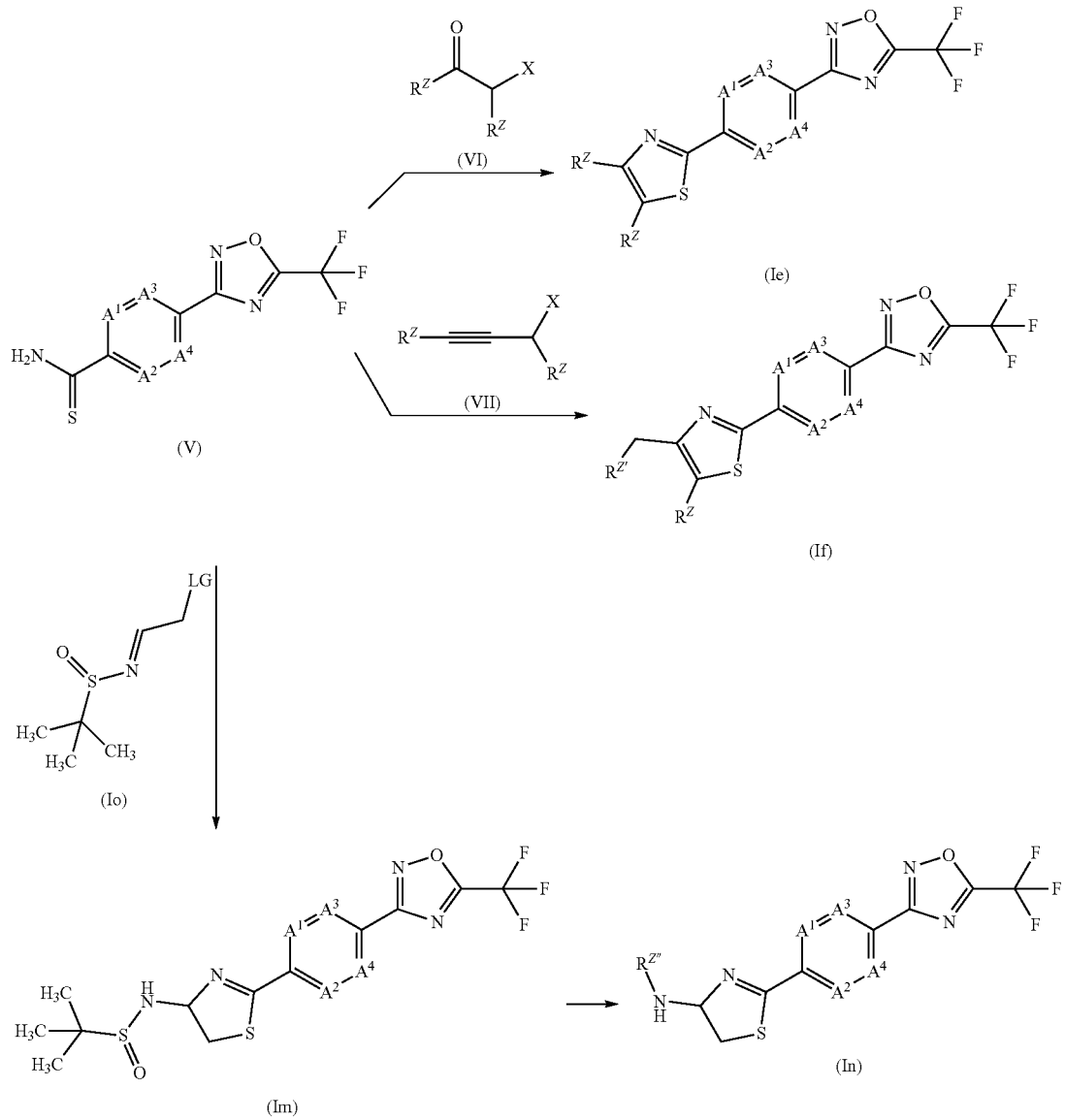

Compounds of formula (V) can be prepared from compounds of formula (VIII) via treatment with Lawesson's reagent (2,4-bis(4-methoxyphenyl)-1,3,2,4-dithiadiphosphetane-2,4-dithione) in a suitable solvent (e.g. toluene) at a temperature of 120° C. For examples, see: Lawesson, O. L. et al *Org. Synth.* 1990, 7, 372. This reaction is shown in Scheme 5 below.

Scheme 5

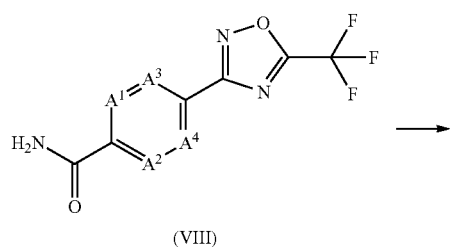

-continued

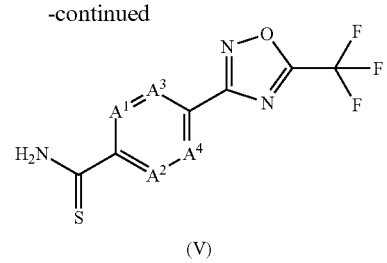

The compounds of formula (Ig), wherein $R^z$ represents suitable definitions for $R^9$ and $R^{11}$, can be obtained by an 1,3-dipolar cycloaddition of nitrile oxides generated in situ from compounds of formula (X) and compounds of formula (XI) under basic conditions, preferably in a suitable solvent (eg, methanol or dichloromethane), preferably at a temperature of 25° C. For examples, see K.-C. Liu et al., *J. Org. Chem.* 1980, 45, 3916 and Lee, G. *Synthesis* 1982, 508.

Compounds of formula (X) are prepared in situ from compounds of formula (IX) using N-chlorosuccimide with known methods. For examples, see: Himo, F. et al *J. Am. Chem. Soc.,* 2005, 127, 210.

Alternatively, aromatic compounds of formula (Ih), wherein $R^z$ is within the definition of $R^{12}$, can be obtained via the same protocol involving alkyne compounds of formula (XII). These reactions are shown in Scheme 6 below.

Scheme 6

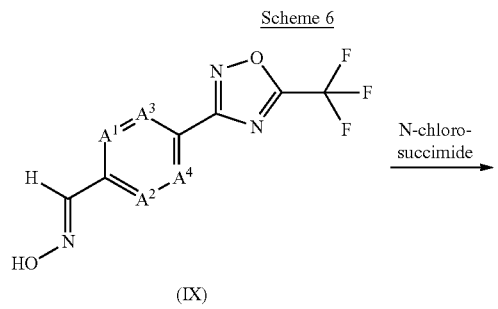

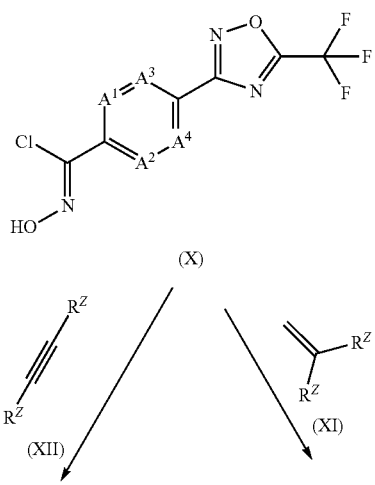

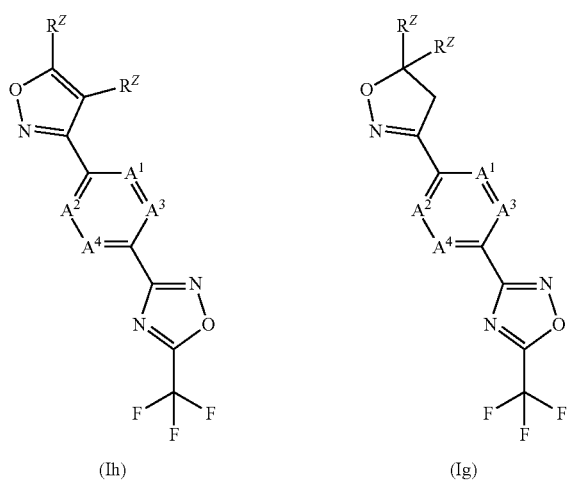

Compounds of formula (IX) can be prepared from compounds of formula (XIII) via treatment with hydroxyamine hydrochloride in the presence of a base (e.g. $Et_3N$) in a suitable solvent (e.g. EtOH) at temperature of 25° C. For examples, see: Ach, D. *Eur. J. Org. Chem.* 2003, 3398. This reaction is shown in Scheme 7 below.

Scheme 7

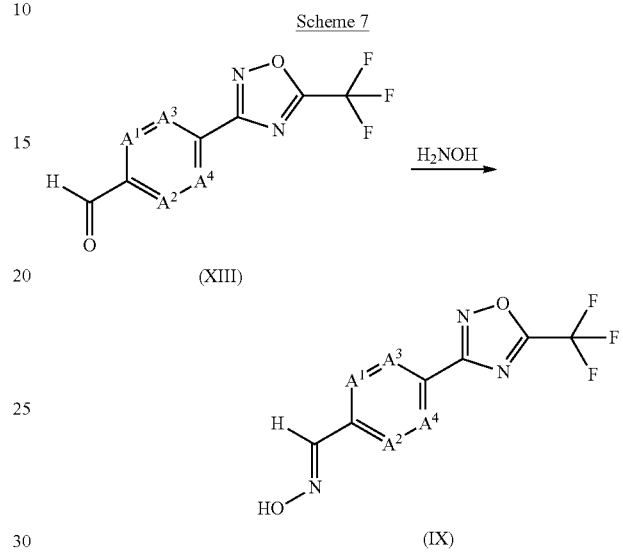

The compounds of formula (Ii), wherein $R^z$ represents suitable definitions for $R^9$ and $R^{11}$, can be obtained by an 1,3-dipolar cycloaddition of nitrile sulphides, generated in situ from compounds of formula (XIV), with compounds of formula (XI), a process that usually takes place via thermal decarboxylation of the corresponding 1,3,4-oxathiazole-2-one of formula (XIV), in a suitable solvent (e.g. toluene) at a temperature of 120° C. For examples, see: Crosby, J. et al *ARKIVOC* 2000, 7, 720. Compounds of formula (XIV) are prepared by known methods reacting carbonochloridothioic acid ($CCl_2OS$) with benzamide compounds of formula (VIII). For examples, see: Pavlik, J. W. et al *J. Org. Chem.* 2003, 68, 4855.

Alternatively, aromatic compounds of formula (Ij), wherein $R^z$ represents a suitable definition of $R^{12}$, can be obtained via the same protocol involving alkyne compounds of formula (XII). This reaction is shown in Scheme 8 below.

Scheme 8

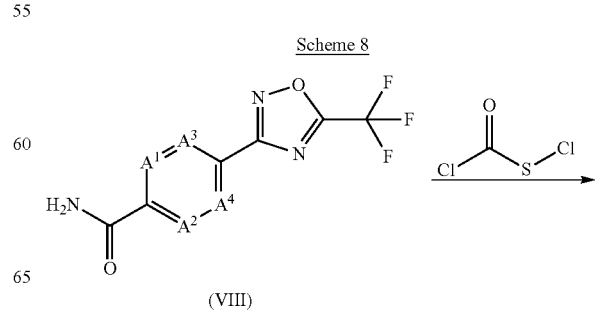

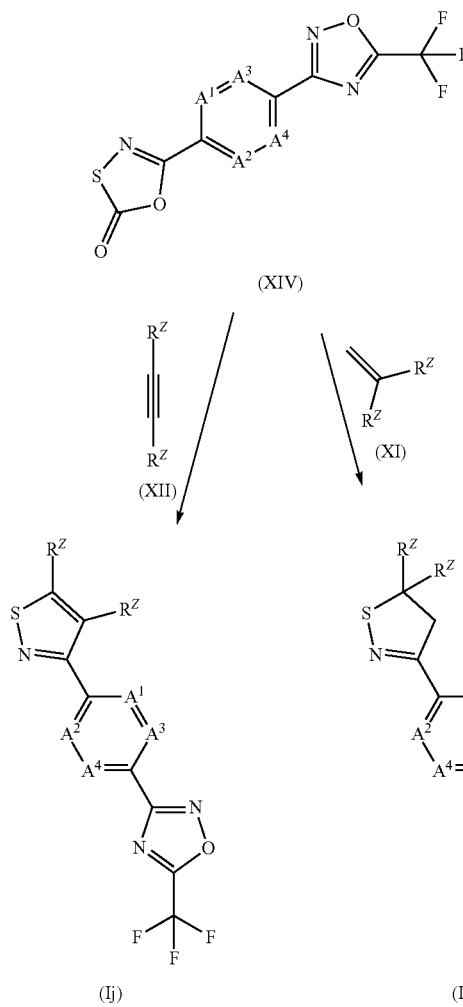

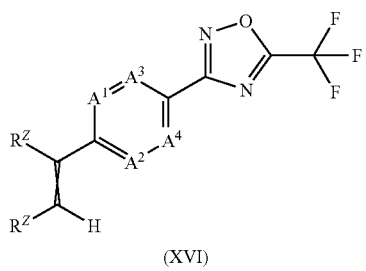

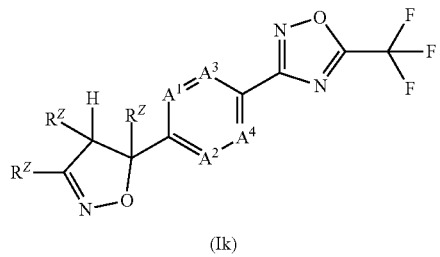

Compounds of formula (XVI), wherein $R^z$ represents suitable definitions for $R^9$ and $R^{11}$, can be prepared from compounds of formula (XVII) via treatment with a phosphonium ylide of formula (XVIII) in the presence of a base (eg. nBuLi, NaH, or potassium tertbutoxide) in a suitable solvent (e.g. tetrahydrofuran) at a temperature between −78° C. and 25° C. Compounds of formula (XVIII) are commercially available. This reaction is shown in Scheme 10 below.

Scheme 10

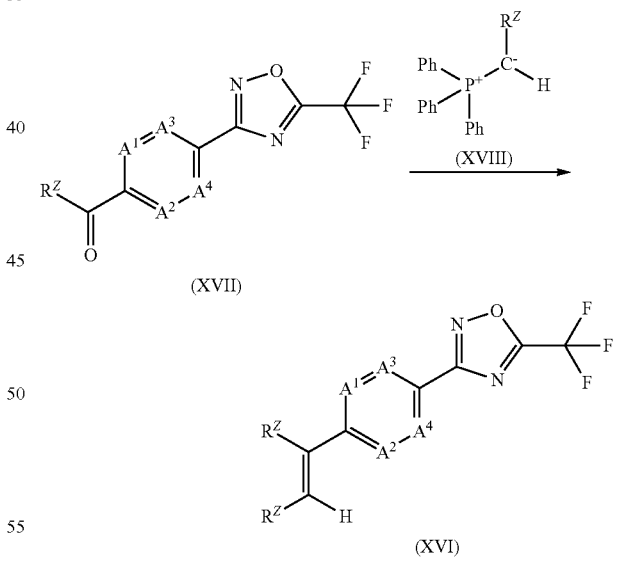

The compounds of formula (Ik), wherein $R^z$ represents suitable definitions for $R^9$ and $R^{11}$, can be obtained by an 1,3-dipolar cycloaddition of nitrile oxides generated in situ from compounds of formula (XV) and compounds of formula (XVI) under basic conditions, in a suitable solvent (e.g., methanol or dichloromethane), preferably at a temperature of 25° C. For examples, see K.-C. Liu et al., *J. Org. Chem.* 1980, 45, 3916 and Lee, G. *Synthesis* 1982, 508. Compounds of formula (XV) are either commercially available or prepared from commercially available aldehydes using known methods. For examples, see: Ach, D. *Eur. J. Org. Chem.* 2003, 3398. This reaction is shown in Scheme 9 below.

Compounds of formula (XIX), wherein T represents Z, CHO, $CO_2H$, $C(O)NH_2$, $C(O)N(Me)OMe$, $C(S)NH_2$, or $-C(R^8)=C(R^8)(R^8)$, can be prepared from compounds of formula (XX) by treatment with trifluoroacetic anhydride in the presence of a base (eg, pyridine or 4-dimethylaminopyridine) in a suitable solvent, such as tetrahydrofuran or ethanol, at a temperature between 25° C. and 75° C. For related examples, see: WO 2003/028729 and WO 2010/045251. This reaction is shown in Scheme 11 below.

Scheme 9

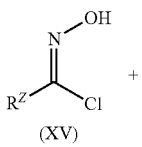

(XV)

Scheme 11

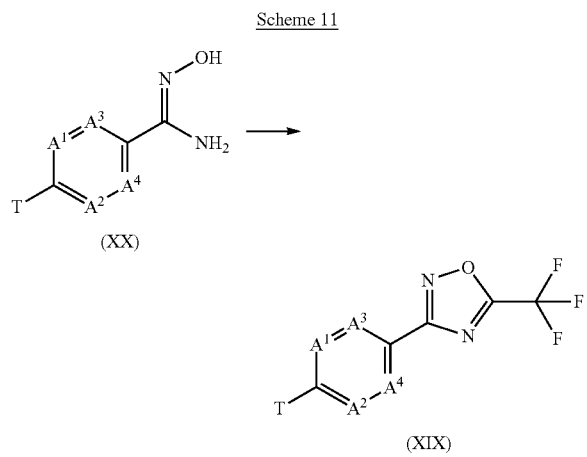

Compounds of formula (XX), wherein T represents Z, C(O)R$^8$, CHO, CO$_2$H, C(O)NH$_2$, C(S)NH$_2$, or —C(R$^8$)═C(R$^8$)(R$^8$), can be prepared from compounds of formula (XXI) by treatment with a hydroxylamine hydrochloride salt in the presence of a base, such as triethylamine, in a suitable solvent, such as methanol, at a temperature between 0° C. and 100° C. For related examples, see Kitamura, S. et al Chem. Pharm. Bull. (2001), 49, 268 and WO 2013/066838. Compounds of formula (XX) are prepared by known methods or are commercially available. This reaction is shown in Scheme 12.

Scheme 12

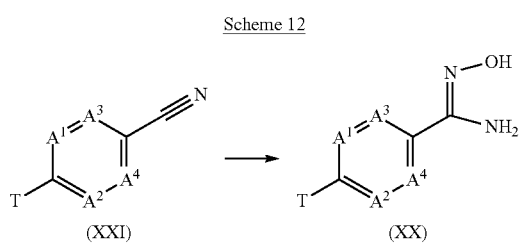

Compounds of formula (XXI) can be prepared from compounds of formula (XXII), wherein X is F, Cl, Br, or I, via treatment with compounds of formula (XXIII), in the presence of a suitable base, (eg., NaH or potassium carbonate), in a suitable solvent, (e.g. dimethylsulfoxide) at a temperature between 25° C. and 120° C. In some cases, a greater reaction performance may be gained with microwaves irradiation. For related examples, see: WO 2015/190506.

Alternatively, wherein X is Cl, Br, or I, compounds of formula (XXI) can be prepared via Pd-catalyzed cross-coupling using a monodentate phosphine palladium complex and a suitable base (eg., sodium tert-butoxide) in a suitable solvent (e.g. toluene, dimethylformamide, sulfolane, dimethylsulfoxide, or dioxane). For examples see, Buchwald, S. L. et al Angew. Chem. Int. Ed. 2006, 45, 6523 and Hartwig, J. Acc. Chem. Res., 2008, 41, 1534. Compounds of formula (XXII) and compounds of formula (XXIII) are commercially available. This reaction is shown in Scheme 13.

Scheme 13

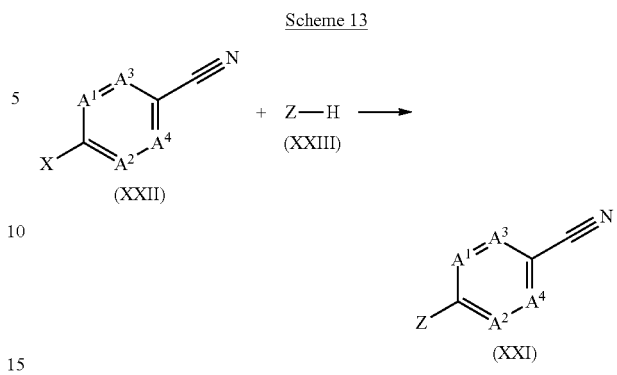

Alternatively, compounds of formula (XXI) can be prepared from compounds of formula (XXII), wherein X is Cl, Br, or I and compounds of formula (VIII), wherein Met is a metalloid [e.g. Sn(Bu)$_3$ or InCl$_2$], through a cross-coupling reaction using a metal (e.g. Cu or Pd) in a suitable solvent (eg. toluene, dimethylformamide, sulfolane, dimethylsulfoxide, or dioxane) at a temperature of between 60° C. and 150° C. For related examples, see J. E. Baldwin et al Angew. Chem. Int. Ed., 2004, 43, 1132 and Font-Sanchis, E. et al J. Org. Chem. 2007, 72, 3589. This reaction is shown in Scheme 14.

Scheme 14

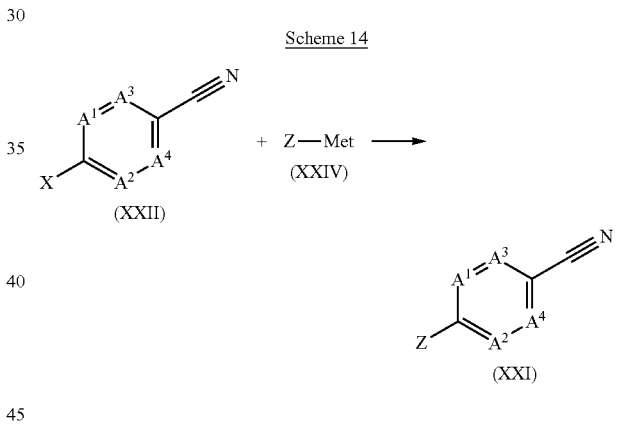

Additionally, compounds of formula (XXI) can be prepared from compounds of formula (XXV), wherein Met is a metal or a metalloid (e.g. ZnCl.LiCl, B(OH)$_2$ or B(pinacol)), and compounds of formula (XXVI) wherein Y is Cl, Br, or I, via cross-coupling reaction using a metal (e.g. Cu or Pd) in the presence of base (e.g. KO-t-Bu, K$_2$CO$_3$, or CS$_2$CO$_3$) and in a suitable solvent (e.g. toluene, dimethylformamide, sulfolane, dimethylsulfoxide, or dioxane) at a temperature of between 60° C. and 150° C. For examples, see: P. Knochel, P. et al Angew. Chem., Int. Ed., 2008, 47, 6802. This reaction is shown in Scheme 15

Scheme 15

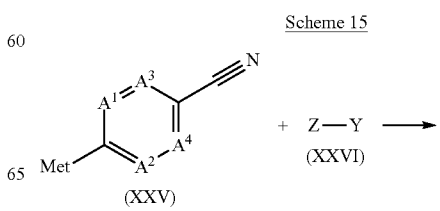

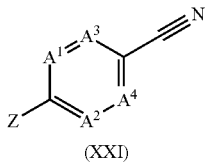

(XXI)

Compounds of formula (XXV), wherein Met is a metal [e.g. ZnCl.LiCl] or a metalloid [e.g. B(OH)$_2$, BF$_3$K, or B(pinacol)], are made from compounds of formula (XXII), wherein X is Cl, Br, or I, via treatment with an organometallic reagent (e.g. n-butyllithium or isopropyl magnesium chloride-LiCl) in a suitable degassed solvent (e.g. tetrahydrofuran) at a temperature between −65° C. and −80° C. with the introduction of ZnCl$_2$ or a suitable boronic ester (e.g. B(OBu)$_3$ of iPrO-B(pinacol)) followed by aqueous acidic hydrolysis with an acid source (e.g. ammonium chloride).

Alternatively, compounds of formula (XXV) can be made from compounds of formula (XXII) via catalysis using a suitable metal source (e.g. palladium) and a diborane species, such as bis(pinacolato)diborane, in the presence of a base (e.g. K$_2$CO$_3$, AcONa or AcOK) and in a suitable solvent (e.g. dioxane or dimethylsulfoxide) at a temperature between 25° C. and 90° C. For related examples, see: Chen, R. et al *Chemistry of Materials* 2007, 19, 4007; Zhu, W. et al *J. Med. Chem.* 2014, 57, 7811. This reaction is shown in Scheme 16.

Scheme 16

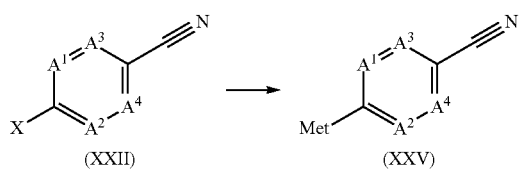

Furthermore, compounds of formula (XXI) can be prepared from compounds of formula (XXVII), wherein X is Br or I, via metal-promoted reaction with a suitable cyanide reagent, such as Pd(0)/Zn(CN)$_2$ or CuCN, in a suitable solvent (e.g. dimethylformamide or N-methylpyrrolidone) at elevated temperature between 100° C. and 120° C. For related examples, see US 2007/0155739 and WO 2009/022746. This reaction is shown in Scheme 17.

Scheme 17

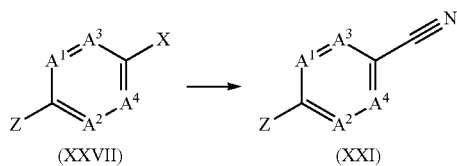

As already indicated, surprisingly, it has now been found that the novel compounds of formula (I) according to the invention have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of formula (I) before planting: seed, for example, can be dressed before being sown. The active compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of formula (I) can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula (I) are for example, effective against fungi and fungal vectors of disease as well as phytopathogenic bacteria and viruses. These fungi and fungal vectors of disease as well as phytopathogenic bacteria and viruses are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. including *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola*, *Cercosporidium personatum*, *Cladosporium* spp, *Claviceps purpurea*, *Coccidioides immitis*, *Cochliobolus* spp, *Colletotrichum* spp. including *C. musae*, *Cryptococcus neoformans*, *Diaporthe* spp, *Didymella* spp, *Drechslera* spp, *Elsinoe* spp, *Epidermophyton* spp, *Erwinia amylovora*, *Erysiphe* spp. including *E. cichoracearum*, *Eutypa lata*, *Fusarium* spp. including *F. culmorum*, *F. graminearum*, *F. langsethiae*, *F. moniliforme*, *F. oxysporum*, *F. proliferatum*, *F. subglutinans*, *F. solani*, *Gaeumannomyces graminis*, *Gibberella fujikuroi*, *Gloeodes pomigena*, *Gloeosporium musarum*, *Glomerella cingulate*, *Guignardia bidwellii*, *Gymnosporangium juniperi-virginianae*, *Helminthosporium* spp, *Hemileia* spp, *Histoplasma* spp. including *H. capsulatum*, *Laetisaria fuciformis*, *Leptographium lindbergi*, *Leveillula taurica*, *Lophodermium seditiosum*, *Microdochium nivale*, *Microsporum* spp, *Monilinia* spp, *Mucor* spp, *Mycosphaerella* spp. including *M. graminicola*, *M. pomi*, *Oncobasidium theobromaeon*, *Ophiostoma piceae*, *Paracoccidioides* spp, *Penicillium* spp. including *P. digitatum*, *P. italicum*, *Petriellidium* spp, *Peronosclerospora* spp. Including *P. maydis*, *P. philippinensis* and *P. sorghi*, *Peronospora* spp, *Phaeosphaeria nodorum*, *Phakopsora pachyrhizi*, *Phellinus igniarus*, *Phialophora* spp, *Phoma* spp, *Phomopsis viticola*, *Phytophthora* spp. including *P. infestans*, *Plasmopara* spp. including *P. halstedii*, *P. viticola*, *Pleospora* spp., *Podosphaera* spp. including *P. leucotricha*, *Polymyxa graminis*, *Polymyxa betae*, *Pseudocercosporella herpotrichoides*, *Pseudomonas* spp, *Pseudoperonospora* spp. including *P. cubensis*, *P. humuli*, *Pseudopeziza tracheiphila*, *Puccinia* Spp. including *P. hordei*, *P. recondita*, *P. striiformis*, *P. triticina*, *Pyrenopeziza* spp, *Pyrenophora* spp, *Pyricularia* spp. including *P. oryzae*, *Pythium* spp. including *P. ultimum*, *Ramularia* spp, *Rhizoctonia* spp, *Rhizomucor pusillus*, *Rhizopus arrhizus*, *Rhynchosporium* spp, *Scedosporium* spp. including *S. apiospermum* and *S. prolificans*, *Schizothyrium pomi*, *Sclerotinia* spp, *Sclerotium* spp, *Septoria* spp, including *S. nodorum*, *S. tritici*, *Sphaerotheca macularis*, *Sphaerotheca fusca* (*Sphaerotheca fuliginea*), *Sporothorix* spp, *Stagonospora nodorum*, *Stemphylium* spp., *Stereum hirsutum*, *Thanatephorus cucumeris*, *Thielaviopsis basicola*, *Tilletia* spp, *Trichoderma* spp. including *T. harzianum*, *T. pseudokoningii*, *T. viride*, *Trichophyton* spp, *Typhula* spp, *Uncinula necator*, *Urocystis* spp, *Ustilago* spp, *Venturia* spp. including *V. inaequalis*, *Verticillium* spp, and *Xanthomonas* spp.

The compounds of formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by 5-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1 Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art. Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2, 5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2, 6-xylyl)-2-methoxyacetamido]-y-butyrolactone, 4-chloro-2-cyano-N,-dimethyl-5-p-tolylimidazole-1-sulfonamide, N-allyl-4, 5,-dimethyl-2-trimethylsilylthiophene-3-carboxamide, N-(l-cyano-1, 2-dimethylpropyl)-2-(2, 4-dichlorophenoxy) propionamide, N-(2-methoxy-5-pyridyl)-cyclopropane carboxamide, (.+-.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy) pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy) phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxy-acrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy) phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy) phenyl]-3-methoxyacrylate, methyl (E)-2-[2-[3-(2-fluoro-phenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy] phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximi-nomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl) methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimi-din-4-yl)-methyloximinomethyl]phenyl}-3-methoxyacry-late, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy] phenyl}-3-methoxyacrylate, methyl (E),(E)-2-{2-[(3-nitrop-henyl)methyloximinomethyl]phenyl}-3-methoxyacrylate, 3-chloro-7-(2-aza-2,7,7-trimethyl-oct-3-en-5-ine), 2,6-di-chloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbam-ate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyetha-nol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithi-azolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dicloran, dichlorophen, dichlozoline, diclobutrazol, diclocymet, diethofencarb, difenoconazole, difenzoquat, diflumetorim, O, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneamino-oxycarbonyl) amino] thio)-β-alaninate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-isopropyl, nuarimol, octhilinone, ofurace, organomercury compounds, orysastrobin, osthol, oxadixyl, oxasulfuron, oxinecopper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, solatenol, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1 R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG- 505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195,RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

The following mixtures of the compounds of formula (I) with active ingredients are preferred. The abbreviation "TX" means one compound selected from the group consisting of the compounds described in Tables 2 to 10 (below) or 2a to 7a (below) or Tables A (entries A-1 to A-51), B (entry B-1), C (entries C-1 to C-14), D (entries D-1 to D-27) and E (entry E-1) (below).

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-A/-methyl-A/-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniarfii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name)

(286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B$_1$ (839)+TX, trimedlure B2 (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl 0-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloropralethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, benzovindiflupyr [1072957-71-1]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, Miconazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-DO-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, fenpicoxamid [517875-34-2]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, oxathiapiprolin [1003318-67-9]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1- b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX; lancotrione [1486617-21-3]+TX, florpyrauxifen [943832-81-3] ]+TX, trifluconazole [1417782-08-1]+TX, mefentrifluconazole [1417782-03-6]+TX, quinofumelin [861647-84-9] ]+TX, chloroprallethrin [399572-87-3] ]+TX, cyhalodiamide [1262605-53-7] ]+TX, fluazaindolizine [1254304-22-7]+TX, fluxametamide [928783-29-3]+TX, epsilon-metofluthrin [240494-71-7] ]+TX, epsilon-momfluorothrin [1065124-65-3]+TX, pydiflumetofen [1228284-64-7]+TX, kappa-bifenthrin [439680-76-9]+TX, broflanilide [1207727-04-5]+TX, dicloromezotiaz [1263629-39-5]+TX, dipymetitrone [16114-35-5]+TX, pyraziflumid [942515-63-1] and kappa-tefluthrin [391634-71-2]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* bacteria var. *aizawai* (XenTari®+TX, DiPel®)+TX, bacteria spp. (GROW-MEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmominiatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+

TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces aibaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verficillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, *Andersoni*-System®)+TX, *Amblyseius californicus* (Amblyline®+TX, Spical®)+TX, *Amblyseius cucumeris* (Thripex®+TX, *Bugline cucumeris*®)+TX, *Amblyseius fallacis* (Fallacis®)+TX, *Amblyseius swirskii* (*Bugline swirskii*®+TX, Swirskii-Mite®)+TX, *Amblyseius womersleyi* (WomerMite®)+TX, *Amitus hesperidum*+TX, *Anagrus atomus*+TX, *Anagrus fusciventris*+TX, *Anagrus kamali*+TX, *Anagrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX,

*Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (*Encarsia* max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (Nesidio-Bug®+TX, Nesibug®)+TX, *Ophyra aenescens* (Biofly®)+TX, *Orius insidiosus* (Thripor-I®+TX, Oriline i®)+TX, *Orius laevigatus* (Thripor —L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline sf®+TX, Sciarid®+TX, Entonem®)+TX, *Steinernema kraussei* (Nemasys L®+TX, BioNem L®+TX, Exhibitline srb®)+TX, *Steinernema nobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus*®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*, and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula (I) selected from a compound described in one of Tables 2 to 10 (below) or 2a to 7a (below) or Tables A (entries A-1 to A-51), B (entry B-1), C (entries C-1 to C-14), D (entries D-1 to D-27) and E (entry E-1) (below), and an active ingredient as described above are preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from one of Tables 2 to 10 (below) or 2a to 7a (below) or Tables A (entries A-1 to A-51), B (entry B-1), C (entries C-1 to C-14), D (entries D-1 to D-27) and E (entry E-1) (below), and one or more active ingredients as described above can be applied, for example, in a single "ready-mix" form, in a combined spray mixture com-posed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Tables 1.1 to 1.19 (below) or Table T1 (below), and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds (I) for the preparation of these compositions are also a subject of the invention.

Another aspect of invention is related to the use of a compound of formula (I) or of a preferred individual compound as defined herein, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula I per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

Table 1 (below) discloses 80 combinations (compounds 1.001 to 1.080) of $A^1$, $A^2$, $A^3$, $A^4$ and $R^9$ substituents in accordance with compounds as defined for Formula (T-1). Formula (T-1) corresponds to Formula (I) as defined for the present invention.

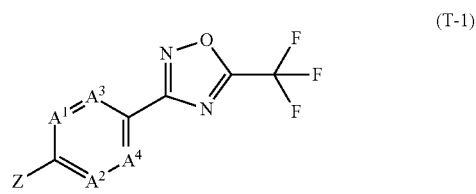

(T-1)

Each of Tables 2 to 10 (which follow Table 1) make available 80 additional individual compounds of the formula (T-1) in which Z is as specifically defined in Tables 2 to 10 (Formulae T-1.2 to T-1.10), which refer to Table 1 wherein $A^1$, $A^2$, $A^3$, $A^4$ and $R^9$ are specifically defined.

TABLE 1

| Compound no. | $A^1$ | $A^2$ | $A^3$ | $A^4$ | $R^9$ |
|---|---|---|---|---|---|
| 1.001 | C—H | C—H | C—H | C—H | — |
| 1.002 | C—H | C—H | C—H | C—H | $CH_3$ |
| 1.003 | C—H | C—H | C—H | C—H | $CH_2CH_3$ |
| 1.004 | C—H | C—H | C—H | C—H | cyclopropyl |
| 1.005 | C—H | C—H | C—H | C—H | cyclohexyl |
| 1.006 | C—H | C—H | C—H | C—H | $CF_3$ |
| 1.007 | C—H | C—H | C—H | C—H | $CH_2OCH_3$ |
| 1.008 | C—H | C—H | C—H | C—H | $CO_2CH_3$ |
| 1.009 | C—F | C—H | C—H | C—H | — |
| 1.010 | C—F | C—H | C—H | C—H | $CH_3$ |
| 1.011 | C—F | C—H | C—H | C—H | $CH_2CH_3$ |
| 1.012 | C—F | C—H | C—H | C—H | cyclopropyl |
| 1.013 | C—F | C—H | C—H | C—H | cyclohexyl |
| 1.014 | C—F | C—H | C—H | C—H | $CF_3$ |
| 1.015 | C—F | C—H | C—H | C—H | $CH_2OCH_3$ |
| 1.016 | C—F | C—H | C—H | C—H | $CO_2CH_3$ |
| 1.017 | C—$CH_3$ | C—H | C—H | C—H | — |
| 1.018 | C—$CH_3$ | C—H | C—H | C—H | $CH_3$ |
| 1.019 | C—$CH_3$ | C—H | C—H | C—H | $CH_2CH_3$ |
| 1.020 | C—$CH_3$ | C—H | C—H | C—H | cyclopropyl |
| 1.021 | C—$CH_3$ | C—H | C—H | C—H | cyclohexyl |
| 1.022 | C—$CH_3$ | C—H | C—H | C—H | $CF_3$ |
| 1.023 | C—$CH_3$ | C—H | C—H | C—H | $CH_2OCH_3$ |
| 1.024 | C—$CH_3$ | C—H | C—H | C—H | $CO_2CH_3$ |
| 1.025 | N | C—H | C—H | C—H | — |
| 1.026 | N | C—H | C—H | C—H | $CH_3$ |
| 1.027 | N | C—H | C—H | C—H | $CH_2CH_3$ |
| 1.028 | N | C—H | C—H | C—H | cyclopropyl |
| 1.029 | N | C—H | C—H | C—H | cyclohexyl |
| 1.030 | N | C—H | C—H | C—H | $CF_3$ |
| 1.031 | N | C—H | C—H | C—H | $CH_2OCH_3$ |
| 1.032 | N | C—H | C—H | C—H | $CO_2CH_3$ |
| 1.033 | C—Cl | C—H | C—H | C—H | — |
| 1.034 | C—Cl | C—H | C—H | C—H | $CH_3$ |
| 1.035 | C—Cl | C—H | C—H | C—H | $CH_2CH_3$ |
| 1.036 | C—Cl | C—H | C—H | C—H | cyclopropyl |
| 1.037 | C—Cl | C—H | C—H | C—H | cyclohexyl |
| 1.038 | C—Cl | C—H | C—H | C—H | $CF_3$ |
| 1.039 | C—Cl | C—H | C—H | C—H | $CH_2OCH_3$ |
| 1.040 | C—Cl | C—H | C—H | C—H | $CO_2CH_3$ |
| 1.041 | C—$OCH_3$ | C—H | C—H | C—H | — |
| 1.042 | C—$OCH_3$ | C—H | C—H | C—H | $CH_3$ |
| 1.043 | C—$OCH_3$ | C—H | C—H | C—H | $CH_2CH_3$ |
| 1.044 | C—$OCH_3$ | C—H | C—H | C—H | cyclopropyl |
| 1.045 | C—$OCH_3$ | C—H | C—H | C—H | cyclohexyl |
| 1.046 | C—$OCH_3$ | C—H | C—H | C—H | $CF_3$ |
| 1.047 | C—$OCH_3$ | C—H | C—H | C—H | $CH_2OCH_3$ |
| 1.048 | C—$OCH_3$ | C—H | C—H | C—H | $CO_2CH_3$ |
| 1.049 | C—$OCH_3$ | C—H | C—H | C—H | — |
| 1.050 | C—$OCH_3$ | C—H | C—H | C—H | $CH_3$ |

TABLE 1-continued

| Compound no. | A¹ | A² | A³ | A⁴ | R⁹ |
|---|---|---|---|---|---|
| 1.051 | C—OCH₃ | C—H | C—H | C—H | CH₂CH₃ |
| 1.052 | C—OCH₃ | C—H | C—H | C—H | cyclopropyl |
| 1.053 | C—OCH₃ | C—H | C—H | C—H | cyclohexyl |
| 1.054 | C—OCH₃ | C—H | C—H | C—H | CF₃ |
| 1.055 | C—OCH₃ | C—H | C—H | C—H | CH₂OCH₃ |
| 1.056 | C—OCH₃ | C—H | C—H | C—H | CO₂CH₃ |
| 1.057 | C—H | C—H | C—F | C—H | — |
| 1.058 | C—H | C—H | C—F | C—H | CH₃ |
| 1.059 | C—H | C—H | C—F | C—H | CH₂CH₃ |
| 1.060 | C—H | C—H | C—F | C—H | cyclopropyl |
| 1.061 | C—H | C—H | C—F | C—H | cyclohexyl |
| 1.062 | C—H | C—H | C—F | C—H | CF₃ |
| 1.063 | C—H | C—H | C—F | C—H | CH₂OCH₃ |
| 1.064 | C—H | C—H | C—F | C—H | CO₂CH₃ |
| 1.065 | C—H | C—H | N | C—H | — |
| 1.066 | C—H | C—H | N | C—H | CH₃ |
| 1.067 | C—H | C—H | N | C—H | CH₂CH₃ |
| 1.068 | C—H | C—H | N | C—H | cyclopropyl |
| 1.069 | C—H | C—H | N | C—H | cyclohexyl |
| 1.070 | C—H | C—H | N | C—H | CF₃ |
| 1.071 | C—H | C—H | N | C—H | CH₂OCH₃ |
| 1.072 | C—H | C—H | N | C—H | CO₂CH₃ |
| 1.073 | N | N | C—H | C—H | — |
| 1.074 | N | N | C—H | C—H | CH₃ |
| 1.075 | N | N | C—H | C—H | CH₂CH₃ |
| 1.076 | N | N | C—H | C—H | cyclopropyl |
| 1.077 | N | N | C—H | C—H | cyclohexyl |
| 1.078 | N | N | C—H | C—H | CF₃ |
| 1.079 | N | N | C—H | C—H | CH₂OCH₃ |
| 1.080 | N | N | C—H | C—H | CO₂CH₃ |

Table 2: This table discloses compounds 2.001 to 2.080 of the formula (T-1.2), which is a compound of formula (I) wherein A¹, A², A³, A⁴, and R⁹ have the specific meanings given in the Table 1.

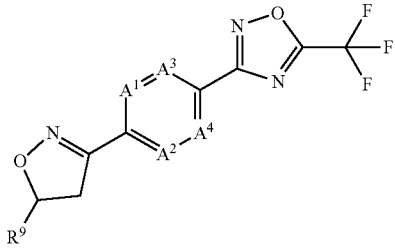

(T-1.2)

Table 3: This table discloses compounds 3.001 to 3.080 of the formula (T-1.3), which is a compound of formula (I) wherein A¹, A², A³, A⁴, and R⁹ have the specific meanings given in the Table 1.

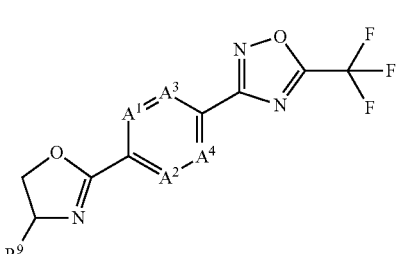

(T-1.3)

Table 4: This table discloses compounds 4.001 to 4.080 of the formula (T-1.4), which is a compound of formula (I) wherein A¹, A², A³, A⁴, and R⁹ have the specific meanings given in the Table 1.

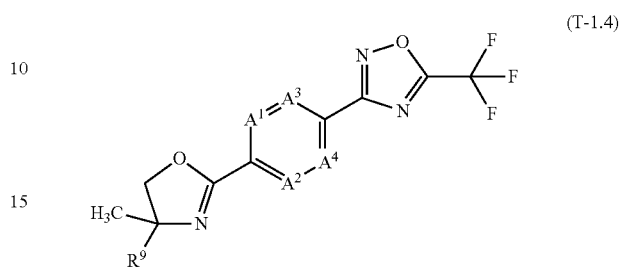

(T-1.4)

Table 5: This table discloses compounds 5.001 to 5.080 of the formula (T-1.5), which is a compound of formula (I) wherein A¹, A², A³, A⁴, and R⁹ have the specific meanings given in the Table 1.

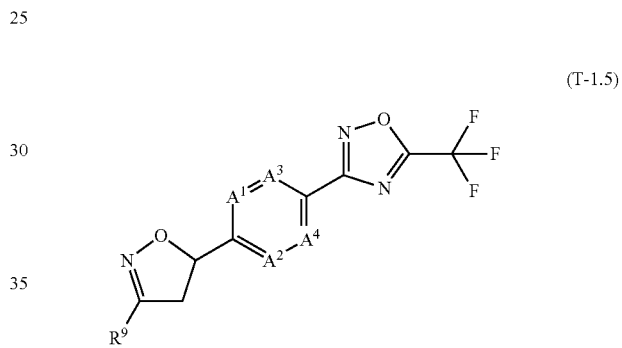

(T-1.5)

Table 6: This table discloses compounds 6.001 to 6.080 of the formula (T-1.6), which is a compound of formula (I) wherein A¹, A², A³, A⁴, and R⁹ have the specific meanings given in the Table 1.

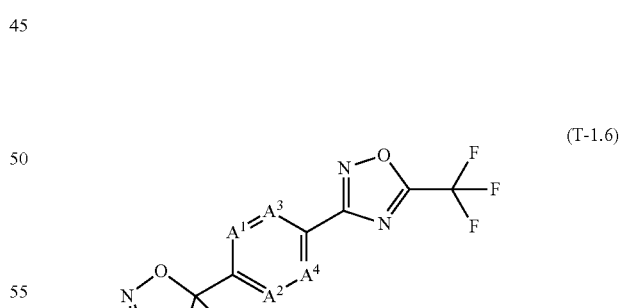

(T-1.6)

Table 7: This table discloses compounds 7.001 to 7.080 of the formula (T-1.7), which is a compound of formula (I) wherein A¹, A², A³, A⁴, and R⁹ have the specific meanings given in the Table 1.

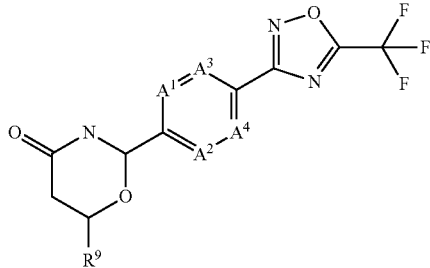

(T-1.7)

Table 8: This table discloses compounds 8.001 to 8.080 of the formula (T-1.8), which is a compound of formula (I) wherein $A^1$, $A^2$, $A^3$, $A^4$, and $R^9$ have the specific meanings given in the Table 1.

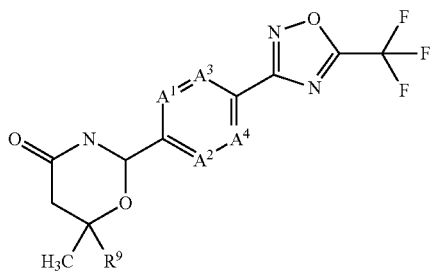

(T-1.8)

Table 9: This table discloses compounds 9.001 to 9.080 of the formula (T-1.9), which is a compound of formula (I) wherein $A^1$, $A^2$, $A^3$, $A^4$, and $R^9$ have the specific meanings given in the Table 1.

(T-1.9)

Table 10: This table discloses compounds 10.001 to 10.080 of the formula (T-1.10), which is a compound of formula (I) wherein $A^1$, $A^2$, $A^3$, $A^4$, and $R^9$ have the specific meanings given in the Table 1.

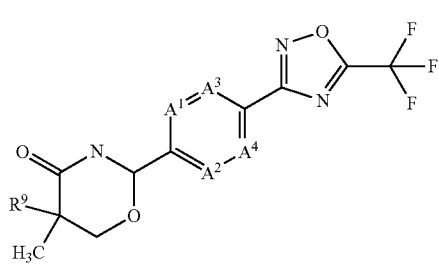

(T-1.10)

Table 1a (below) discloses 80 combinations (compounds 1a.001 to 1a.080) of $A^1$, $A^2$, $A^3$, $A^4$ and $R^{12}$ or $R^{14}$ substituents in accordance with compounds as defined for Formula (T-1). Formula (T-1) corresponds to Formula (I) as defined for the present invention.

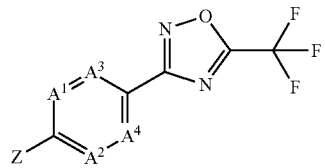

(T-1)

Each of Tables 2a to 7a (which follow Table 1a) make available 80 additional individual compounds of the formula (T-1) in which Z is as specifically defined in Tables 2a to 7a (Formulae T-1.2a to T-1.7a), which refer to Table 1a wherein $A^1$, $A^2$, $A^3$, $A^4$ and $R^{12}$ or $R^{14}$ are specifically defined.

TABLE 1a

| Compound no. | $A^1$ | $A^2$ | $A^3$ | $A^4$ | $R^{12}$ or $R^{14}$ |
|---|---|---|---|---|---|
| 1a.001 | C—H | C—H | C—H | C—H | — |
| 1a.002 | C—H | C—H | C—H | C—H | CH₃ |
| 1a.003 | C—H | C—H | C—H | C—H | CH₂CH₃ |
| 1a.004 | C—H | C—H | C—H | C—H | cyclopropyl |
| 1a.005 | C—H | C—H | C—H | C—H | cyclohexyl |
| 1a.006 | C—H | C—H | C—H | C—H | CF₃ |
| 1a.007 | C—H | C—H | C—H | C—H | CH₂OCH₃ |
| 1a.008 | C—H | C—H | C—H | C—H | CO₂CH₃ |
| 1a.009 | C—F | C—H | C—H | C—H | — |
| 1a.010 | C—F | C—H | C—H | C—H | CH₃ |
| 1a.011 | C—F | C—H | C—H | C—H | CH₂CH₃ |
| 1a.012 | C—F | C—H | C—H | C—H | cyclopropyl |
| 1a.013 | C—F | C—H | C—H | C—H | cyclohexyl |
| 1a.014 | C—F | C—H | C—H | C—H | CF₃ |
| 1a.015 | C—F | C—H | C—H | C—H | CH₂OCH₃ |
| 1a.016 | C—F | C—H | C—H | C—H | CO₂CH₃ |
| 1a.017 | C—CH₃ | C—H | C—H | C—H | — |
| 1a.018 | C—CH₃ | C—H | C—H | C—H | CH₃ |
| 1a.019 | C—CH₃ | C—H | C—H | C—H | CH₂CH₃ |
| 1a.020 | C—CH₃ | C—H | C—H | C—H | cyclopropyl |
| 1a.021 | C—CH₃ | C—H | C—H | C—H | cyclohexyl |
| 1a.022 | C—CH₃ | C—H | C—H | C—H | CF₃ |
| 1a.023 | C—CH₃ | C—H | C—H | C—H | CH₂OCH₃ |
| 1a.024 | C—CH₃ | C—H | C—H | C—H | CO₂CH₃ |
| 1a.025 | N | C—H | C—H | C—H | — |
| 1a.026 | N | C—H | C—H | C—H | CH₃ |
| 1a.027 | N | C—H | C—H | C—H | CH₂CH₃ |
| 1a.028 | N | C—H | C—H | C—H | cyclopropyl |
| 1a.029 | N | C—H | C—H | C—H | cyclohexyl |
| 1a.030 | N | C—H | C—H | C—H | CF₃ |
| 1a.031 | N | C—H | C—H | C—H | CH₂OCH₃ |
| 1a.032 | N | C—H | C—H | C—H | CO₂CH₃ |
| 1a.033 | C—Cl | C—H | C—H | C—H | — |
| 1a.034 | C—Cl | C—H | C—H | C—H | CH₃ |
| 1a.035 | C—Cl | C—H | C—H | C—H | CH₂CH₃ |
| 1a.036 | C—Cl | C—H | C—H | C—H | cyclopropyl |
| 1a.037 | C—Cl | C—H | C—H | C—H | cyclohexyl |
| 1a.038 | C—Cl | C—H | C—H | C—H | CF₃ |
| 1a.039 | C—Cl | C—H | C—H | C—H | CH₂OCH₃ |
| 1a.040 | C—Cl | C—H | C—H | C—H | CO₂CH₃ |
| 1a.041 | C—OCH₃ | C—H | C—H | C—H | — |
| 1a.042 | C—OCH₃ | C—H | C—H | C—H | CH₃ |
| 1a.043 | C—OCH₃ | C—H | C—H | C—H | CH₂CH₃ |
| 1a.044 | C—OCH₃ | C—H | C—H | C—H | cyclopropyl |
| 1a.045 | C—OCH₃ | C—H | C—H | C—H | cyclohexyl |
| 1a.046 | C—OCH₃ | C—H | C—H | C—H | CF₃ |
| 1a.047 | C—OCH₃ | C—H | C—H | C—H | CH₂OCH₃ |
| 1a.048 | C—OCH₃ | C—H | C—H | C—H | CO₂CH₃ |
| 1a.049 | C—OCH₃ | C—H | C—H | C—H | — |
| 1a.050 | C—OCH₃ | C—H | C—H | C—H | CH₃ |

TABLE 1a-continued

| Compound no. | $A^1$ | $A^2$ | $A^3$ | $A^4$ | $R^{12}$ or $R^{14}$ |
|---|---|---|---|---|---|
| 1a.051 | C—OCH$_3$ | C—H | C—H | C—H | CH$_2$CH$_3$ |
| 1a.052 | C—OCH$_3$ | C—H | C—H | C—H | cyclopropyl |
| 1a.053 | C—OCH$_3$ | C—H | C—H | C—H | cyclohexyl |
| 1a.054 | C—OCH$_3$ | C—H | C—H | C—H | CF$_3$ |
| 1a.055 | C—OCH$_3$ | C—H | C—H | C—H | CH$_2$OCH$_3$ |
| 1a.056 | C—OCH$_3$ | C—H | C—H | C—H | CO$_2$CH$_3$ |
| 1a.057 | C—H | C—H | C—F | C—H | — |
| 1a.058 | C—H | C—H | C—F | C—H | CH$_3$ |
| 1a.059 | C—H | C—H | C—F | C—H | CH$_2$CH$_3$ |
| 1a.060 | C—H | C—H | C—F | C—H | cyclopropyl |
| 1a.061 | C—H | C—H | C—F | C—H | cyclohexyl |
| 1a.062 | C—H | C—H | C—F | C—H | CF$_3$ |
| 1a.063 | C—H | C—H | C—F | C—H | CH$_2$OCH$_3$ |
| 1a.064 | C—H | C—H | C—F | C—H | CO$_2$CH$_3$ |
| 1a.065 | C—H | C—H | N | C—H | — |
| 1a.066 | C—H | C—H | N | C—H | CH$_3$ |
| 1a.067 | C—H | C—H | N | C—H | CH$_2$CH$_3$ |
| 1a.068 | C—H | C—H | N | C—H | cyclopropyl |
| 1a.069 | C—H | C—H | N | C—H | cyclohexyl |
| 1a.070 | C—H | C—H | N | C—H | CF$_3$ |
| 1a.071 | C—H | C—H | N | C—H | CH$_2$OCH$_3$ |
| 1a.072 | C—H | C—H | N | C—H | CO$_2$CH$_3$ |
| 1a.073 | N | N | C—H | C—H | — |
| 1a.074 | N | N | C—H | C—H | CH$_3$ |
| 1a.075 | N | N | C—H | C—H | CH$_2$CH$_3$ |
| 1a.076 | N | N | C—H | C—H | cyclopropyl |
| 1a.077 | N | N | C—H | C—H | cyclohexyl |
| 1a.078 | N | N | C—H | C—H | CF$_3$ |
| 1a.079 | N | N | C—H | C—H | CH$_2$OCH$_3$ |
| 1a.080 | N | N | C—H | C—H | CO$_2$CH$_3$ |

Table 2a: This table discloses compounds 2a.001 to 2a.080 of the formula (T-1.2a), which is a compound of formula (I) wherein $A^1$, $A^2$, $A^3$, $A^4$, and $R^{12}$ have the specific meanings given in the Table 1a.

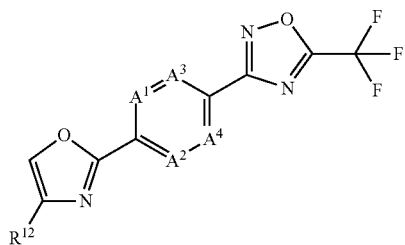

(T-1.2a)

Table 3a: This table discloses compounds 3a.001 to 3a.080 of the formula (T-1.3a), which is a compound of formula (I) wherein $A^1$, $A^2$, $A^3$, $A^4$, and $R^{12}$ have the specific meanings given in the Table 1a.

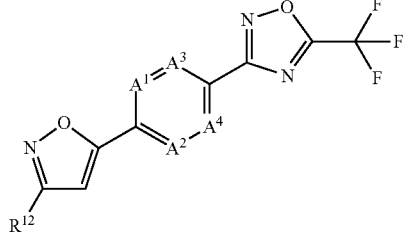

(T-1.3a)

Table 4a: This table discloses compounds 4a.001 to 4a.080 of the formula (T-1.4a), which is a compound of formula (I) wherein $A^1$, $A^2$, $A^3$, $A^4$, and $R^{12}$ have the specific meanings given in the Table 1a.

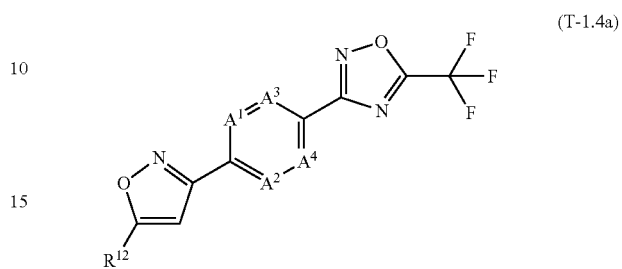

(T-1.4a)

Table 5a: This table discloses compounds 5a.001 to 5a.080 of the formula (T-1.5a), which is a compound of formula (I) wherein $A^1$, $A^2$, $A^3$, $A^4$, and $R^{12}$ have the specific meanings given in the Table 1.

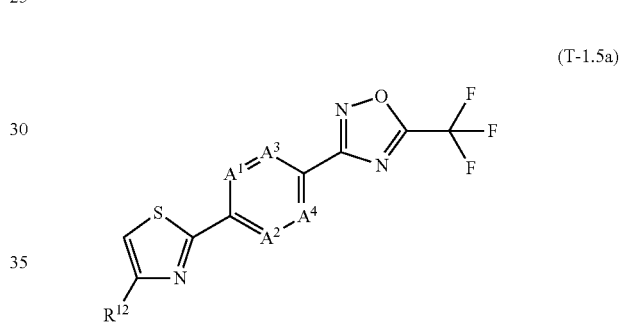

(T-1.5a)

Table 6a: This table discloses compounds 6a.001 to 6a.080 of the formula (T-1.6a), which is a compound of formula (I) wherein $A^1$, $A^2$, $A^3$, $A^4$, and $R^{14}$ have the specific meanings given in the Table 1a.

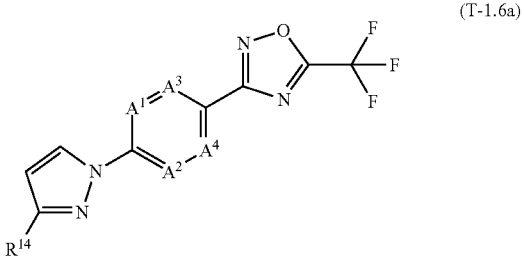

(T-1.6a)

Table 7a: This table discloses compounds 7a.001 to 7a.080 of the formula (T-1.7a), which is a compound of formula (I) wherein $A^1$, $A^2$, $A^3$, $A^4$, and $R^{14}$ have the specific meanings given in the Table 1a.

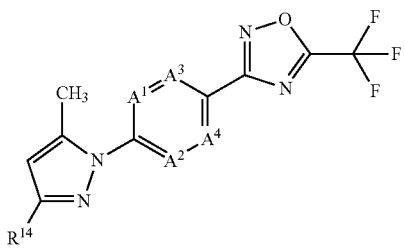

(T-1.7a)

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Throughout this description, temperatures are given in degrees Celsius (° C.) and "mp." means melting point. LC/MS means Liquid Chromatography Mass Spectrometry and the description of the apparatus and the method is as follows:
The LC/MS Apparatus and Method is:
Method A:
Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (mL/min) 0.85.
Method B:
Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (mL/min) 0.85.

Where necessary, enantiomerically pure final compounds may be obtained from racemic materials as appropriate via standard physical separation techniques, such as reverse phase chiral chromatography, or through stereoselective synthetic techniques, eg, by using chiral starting materials.

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

List of Abbreviations

AIBN=azobisisobutyronitrile
DMF=dimethylformamide
DIPEA=N,N-di-isopropylethylamine
EtOAc=ethyl acetate
KHMDS=potassium bis(trimethylsilyl)amide
HCl=hydrochloric acid
mp=melting point
° C.=degrees Celsius
MeOH=methyl alcohol
NaOH=sodium hydroxide
NBS=N-bromosuccinimide
min=minutes
rt=room temperature
TFAA=trifluoroacetic acid anhydride
THF=tetrahydrofuran
$t_R$=Retention time
LC/MS=Liquid Chromatography Mass Spectrometry (description of the apparatus and the methods used for LC/MS analysis are given above)

PREPARATION EXAMPLES

Example 1: This example illustrates the preparation of 3-[4-(5-methyloxazol-2-yl)phenyl]-5-(trifluoromethyl)-1,2,4-oxadiazole (Compound C-2 of Table C).

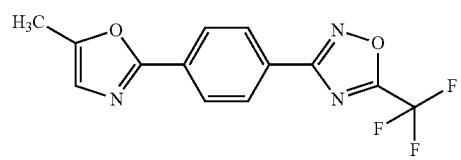 [SMILES: Cc1cnc(-c2ccc(-c3noc(C(F)(F)F)n3)cc2)o1]

Step 1: Preparation of 4-[5-(trifluoromethyl)-1,2,4-oxadiazol-3-yl]benzoyl chloride

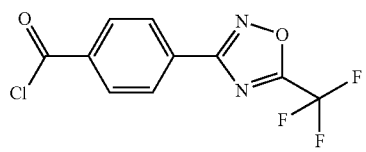 [SMILES: O=C(Cl)c1ccc(-c2noc(C(F)(F)F)n2)cc1]

To a solution of 4-[5-(trifluoromethyl)-1,2,4-oxadiazol-3-yl]benzoic acid (5.0 g, 19 mmol) in a mixture of dichloromethane (190 mL) and dimethylformamide (0.15 mL) was slowly added thionylchloride (2.8 mL, 39 mmol). The resulting suspension was then heated under reflux for 4 hours, and then evaporated to dryness under vacuum to afford 4-[5-(trifluoromethyl)-1,2,4-oxadiazol-3-yl]benzoyl chloride as a beige solid. The product was used for the next step without further purification.

Step 2: Preparation of N-prop-2-ynyl-4-[5-(trifluoromethyl)-1,2,4-oxadiazol-3-yl]benzamide

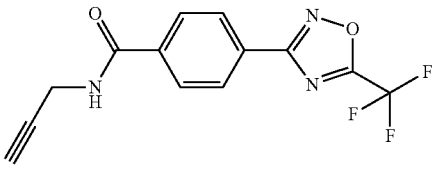 [SMILES: C#CCNC(=O)c1ccc(-c2noc(C(F)(F)F)n2)cc1]

To a solution of prop-2-yn-1-amine (0.7 mL, 11 mmol) and triethylamine (3.1 mL, 22 mmol) in dichloromethane (54 mL) was added 4-[5-(trifluoromethyl)-1,2,4-oxadiazol-3-yl]benzoyl chloride (3 g, 11 mmol) in one portion. The resulting mixture was stirred for 6 hours at room temperature. The reaction mixture was then diluted with dichloromethane and water. The organic layer was washed with 1N HCl, 1N NaOH and brine, dried over $Na_2SO_4$ and concentrated under reduced pressure. The crude residue was purified by flash chromatography to give N-prop-2-ynyl-4-[5-(trifluoromethyl)-1,2,4-oxadiazol-3-yl]benzamide as a white solid.

$^1$H NMR (400 MHz, $CDCl_3$) δ ppm: 2.32 (t, J=2.6 Hz, 1H) 4.30 (dd, J=5.1, 2.6 Hz, 2H) 6.38 (br. s., 1H) 7.89-7.99 (m, 2H) 8.16-8.27 (m, 2H).

LC/MS (Method A) retention time=0.93 min; 296 [M+H$^+$], mp: 168-170° C.

Step 3: Synthesis of 3-[4-(5-methyloxazol-2-yl)phenyl]-5-(trifluoromethyl)-1,2,4-oxadiazole To a suspension of N-prop-2-ynyl-4-[5-(trifluoromethyl)-1,2,4-oxadiazol-3-yl]benzamide (295 mg, 1 mmol) in dichloroethane (5 mL) was added iron trichloride (81 mg, 0.5 mmol). The resulting mixture was heated up to 80° C. and stirred for 4 hours. The reaction mixture was then cooled and diluted with water. The aqueous layer was extracted 3 times with dichloromethane, and the combined organic layers were washed with water and brine, dried over $Na_2SO_4$ and concentrated under reduced pressure. The crude product was purified by flash chromatography to give 3-[4-(5-methyloxazol-2-yl)phenyl]-5-(trifluoromethyl)-1,2,4-oxadiazole.

$^1$H NMR (400 MHz, $CDCl_3$) δ ppm: 2.43 (d, J=1.1 Hz, 3H) 6.90 (d, J=1.1 Hz, 1H) 8.08-8.22 (m, 4H).

LC/MS (Method A) retention time=1.18 min; 296 [M+H$^+$], mp: 109-111° C.

Example 2: This example illustrates the preparation of 3-[4-(4-methylthiazol-2-yl)phenyl]-5-(trifluoromethyl)-1,2,4-oxadiazole (Compound C-8 of Table C)

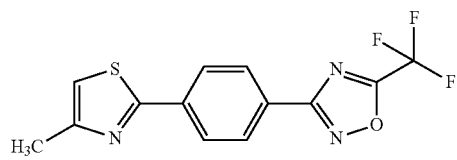

Step 1: Preparation of 4-[5-(trifluoromethyl)-1,2,4-oxadiazol-3-yl]benzamide

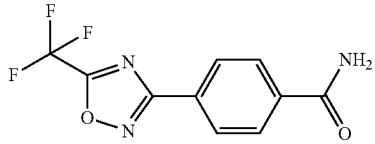 [SMILES: NC(=O)c1ccc(-c2noc(C(F)(F)F)n2)cc1]

A solution of 4-[5-(trifluoromethyl)-1,2,4-oxadiazol-3-yl]benzoyl chloride (26.8 g, 96.9 mmol) in dichloromethane (25 mL) was added dropwise over a period of 60 min to a mixture of dichloromethane (100 mL) and 25% ammonia solution (30 mL) at 0° C. After the addition, the reaction mixture was further diluted with dichloromethane (40 mL). The suspension was stirred for 2 hours at 0° C. and then warmed to room temperature. The suspension was filtered and washed with water until the filtrate reached a pH of 7. The obtained crystals were successively washed with cyclohexane (100 ml) and ether (2×100 mL), dried under vacuum at 60° C. to give 4-[5-(trifluoromethyl)-1,2,4-oxadiazol-3-yl]benzamide as a beige solid.

$^1$H NMR (400 MHz, $CD_3OD$) δ ppm: 8.03-8.08 (m, 2H) 8.19-8.25 (m, 2H).

LC/MS (Method B) retention time=1.19 min; 258 [M+H$^+$], mp: 235-237° C.

Step 2: Preparation of 4-[5-(trifluoromethyl)-1,2,4-oxadiazol-3-yl]benzenecarbothioamide

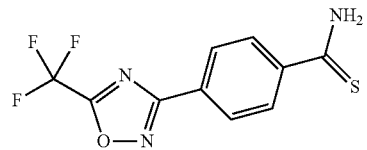 [SMILES: NC(=S)c1ccc(-c2noc(C(F)(F)F)n2)cc1]

To a mixture of 4-[5-(trifluoromethyl)-1,2,4-oxadiazol-3-yl]benzamide (2.57 g, 9.99 mmol) in toluene (100 mL) was added Lawesson's reagent (3.03 g, 7.50 mmol). The resulting reaction mixture was heated to 90-100° C. for 10 min and then cooled before being poured into a mixture of aq $NaHCO_3$ (250 mL) and ethyl acetate (250 mL). The organic phase was separated, dried over $MgSO_4$ and concentrated. The crude product was purified by flash chromatography over silica gel to give 4-[5-(trifluoromethyl)-1,2,4-oxadiazol-3-yl]benzenecarbothioamide as yellow crystal.

LC/MS (Method B) retention time=1.42 min; 274 [M+H$^+$], mp: 192-194° C.

Step 3: Synthesis of 3-[4-(4-methylthiazol-2-yl)phenyl]-5-(trifluoromethyl)-1,2,4-oxadiazole

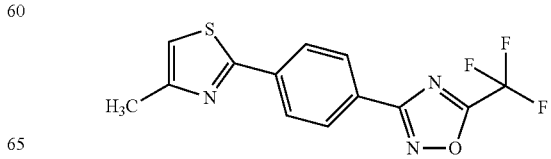

To a solution of 4-[5-(trifluoromethyl)-1,2,4-oxadiazol-3-yl]benzenecarbothioamide (0.2 g, 0.731 mmol) in dry ethanol (5 mL) was added 1-chloropropan-2-one (0.059 mL, 0.731 mmol). The resulting solution was heated to 70° C. and stirred for 24 hours. The cooled reaction mixture was then poured into a mixture of water and ethyl acetate. The organic layer was separated, washed with NaHCO$_3$ and brine, dried over MgSO$_4$ and evaporated. The crude residue was purified over silica gel to give 3-[4-(4-methylthiazol-2-yl)phenyl]-5-(trifluoromethyl)-1,2,4-oxadiazole white crystals.

1H NMR (400 MHz, CDCl$_3$) δ ppm: 2.54 (d, J=0.7 Hz, 3H) 6.97 (d, J=1.1 Hz, 1H) 8.07-8.12 (m, 2H) 8.16-8.22 (m, 2H).

LC/MS (Method B) retention time=2.04 min; 312 [M+H$^+$], mp: 89-90° C.

Example 3: This example illustrates the preparation of 3-[4-(3-methyl-4,5-dihydroisoxazol-5-yl)phenyl]-5-(trifluoromethyl)-1,2,4-oxadiazole (Compound A-4 of Table A).

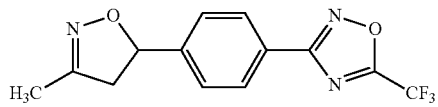 [SMILES: CC1=NOC(c2ccc(-c3noc(C(F)(F)F)n3)cc2)C1]

Step 1: Preparation of N-methoxy-N-methyl-4-[5-(trifluoromethyl)-1,2,4-oxadiazol-3-yl]benzamide

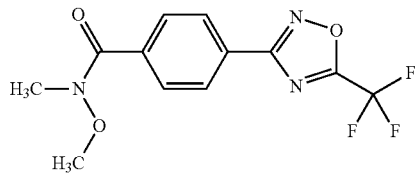

A solution of 4-[5-(trifluoromethyl)-1,2,4-oxadiazol-3-yl] benzoyl chloride (4.15 g, 14.6 mmol) in dichloromethane (20 mL) was added dropwise at room temperature to a stirred solution of N-methoxymethanamine (1.10 g, 17.5 mmol) and triethylamine (3.10 mL, 21.8 mmol) in dichloromethane (80 mL). The mixture was stirred at room temperature for 18 hours. The reaction mixture was poured into water and extracted twice with dichloromethane. The combined organic layers were washed with brine, dried over sodium sulfate, and filtered. The solvent was removed under reduced pressure and the resultant crude residue was subjected to flash chromatography over silica gel (heptane: EtOAc eluent gradient 9:1 to 65:35) to afford 4.12 g of N-methoxy-N-methyl-4-[5-(trifluoromethyl)-1,2,4-oxadiazol-3-yl]benzamide as a solid.

$^1$H NMR (400 MHz, CDCl$_3$) δ ppm: 8.18 (d, 2H), 7.84 (d, 2H), 3.56 (s, 3H), 3.40 (s, 3H).

LC/MS (Method A) retention time=0.97 min; 302 [M+H]$^+$.

Step 2: Preparation of 4-[5-(trifluoromethyl)-1,2,4-oxadiazol-3-yl]benzaldehyde

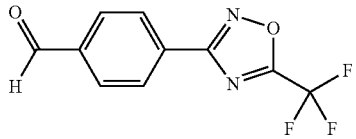 [SMILES: O=Cc1ccc(-c2noc(C(F)(F)F)n2)cc1]

In a 75-mL multi neck flask equipped with stirrer, thermometer at −78° C. under argon, DIBAL-H, 1.0 M in toluene (16 mL, 16.0 mmol) was added dropwise to a solution of N-methoxy-N-methyl-4-[5-(trifluoromethyl)-1,2,4-oxadiazol-3-yl]benzamide (4.10 g, 13.3 mmol) in 2-methyltetrahydrofuran (90 mL). The mixture was stirred two hours at −78° C. and for one hour the temperature was let increase to 0° C. The mixture was quenched by dropwise addition of a sat. ammonium chloride solution. Precipitation of a white solid occurred. 4 M HCl was added until full solubilisation. The mixture was extracted thrice with ethyl acetate. Combined organics were dried over magnesium sulfate and evaporated to afford a crude residue as beige solid. The crude residue was subjected to flash chromatography over silicagel (heptane: EtOAc eluent gradient 99:1 to 90:10) 4-[5-(trifluoromethyl)-1,2,4-oxadiazol-3-yl]benzaldehyde as a white solid.

$^1$H NMR (400 MHz, CDCl$_3$) δ ppm: 10.12 (s, 1H), 8.31 (d, 2H), 8.05 (d, 2H).

$^{19}$F NMR (400 MHz, CDCl$_3$) δ ppm: −65.29 (s).

mp: 40-50° C.

Step 3: Preparation of 5-(trifluoromethyl)-3-(4-vinylphenyl)-1,2,4-oxadiazole

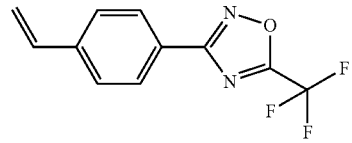 [SMILES: C=Cc1ccc(-c2noc(C(F)(F)F)n2)cc1]

To a white suspension of methyl(triphenyl)phosphonium hydrobromide (7.10 g, 19.8 mmol) in THF (42 mL) at rt was added t-BuOK in THF (1M, 18.6 mL, 18.6 mmol), the resulting yellow solution was stirred at rt for 1 hour. The reaction mixture was then cooled to −78° C. and a solution of 4-[5-(trifluoromethyl)-1,2,4-oxadiazol-3-yl]benzaldehyde (3.00 g, 12.4 mmol) in THF (20 ml) was added dropwise. The reaction mixture was then warmed from −78° C. to −30° C. over a period of 100 min and then warmed to rt and stirred for an additional 90 min. The pH of the mixture was adjusted to neutral by the addition of 1M HCl and the aqueous phase was extracted with AcOEt. The combined organic layers were washed with brine, dried over Na$_2$SO$_4$, filtered, concentrated and purified by Isco combiflash Rf using cyclohexane/AcOEt to give 5-(trifluoromethyl)-3-(4-vinylphenyl)-1,2,4-oxadiazole as a white solid.

$^1$H NMR (400 MHz, CDCl$_3$) δ ppm: 5.34 (d, J=10.6 Hz, 1H) 5.82 (d, J=17.6 Hz, 1H) 6.70 (dd, J=17.6, 10.6 Hz, 1H) 7.48 (d, J=8.0 Hz, 2H) 8.01 (d, J=7.8 Hz, 2H).

LC/MS (Method A) retention time=1.19 min; 259 [M+H]$^+$.

Step 4: Preparation of 3-[4-(3-methyl-4,5-dihydroisoxazol-5-yl)phenyl]-5-(trifluoromethyl)-1,2,4-oxadiazole To a solution of 5-(trifluoromethyl)-3-(4-vinylphenyl)-1,2,4-oxadiazole (0.050 g, 0.21 mmol) in methanol (2.1 mL) was added acetaldoxime (0.014 g, 0.014 mL, 0.23 mmol) followed by (diacetoxyiodo)benzene (0.074 g, 0.23 mmol). The reaction mixture was stirred overnight at rt. As the reaction did not proceed to completion one additional equivalent of (diacetoxyiodo)benzene was added and the reaction mixture was stirred for an additional 1h 40 mins at rt before all the solvents were evaporated. The resulting oil was then purified by Isco combiflash Rf using cyclohexane/AcOEt as eluent to give 3-[4-(3-methyl-4,5-dihydroisoxazol-5-yl)phenyl]-5-(trifluoromethyl)-1,2,4-oxadiazole as a white solid.

$^1$H NMR (400 MHz, CDCl$_3$) δ ppm: 1.98 (s, 3H) 2.85 (ddd, J=17.1, 7.7, 0.9 Hz, 1H) 3.38 (ddd, J=17.1, 11.0, 0.9 Hz, 1H) 5.57 (dd, J=11.0, 7.7 Hz, 1H) 7.43 (d, J=8.1 Hz, 2H) 8.05 (d, J=8.1 Hz, 2H).

LC/MS (Method A) retention time=1.03 min; 298 [M+H]$^+$.

mp: 89-92° C.

Example 4: This example illustrates the preparation of 3-[4-(3-methylisoxazol-5-yl)phenyl]-5-(trifluoromethyl)-1,2,4-oxadiazole (Compound C-11 of Table C).

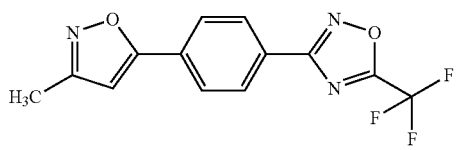 [SMILES: Cc1cc(-c2ccc(-c3noc(C(F)(F)F)n3)cc2)on1]

To a solution of 3-[4-(3-methyl-4,5-dihydroisoxazol-5-yl)phenyl]-5-(trifluoromethyl)-1,2,4-oxadiazole (0.040 g, 0.13 mmol) in toluene (0.45 mL) was added activated manganese (IV) oxide (0.200 g, 2.30 mmol). The reaction mixture was stirred at 100° C. for 70 min. The reaction mixture was then cooled, filtered over celite and washed with toluene. The filtrate was concentrated to give 3-[4-(3-methylisoxazol-5-yl)phenyl]-5-(trifluoromethyl)-1,2,4-oxadiazole as a white solid.

$^1$H NMR (400 MHz, CDCl$_3$) δ ppm: 2.32 (s, 3H) 6.43 (s, 1H) 7.81-7.89 (m, 2H) 8.12-8.18 (m, 2H).

LC/MS (Method A) retention time=1.12 min; 296 [M+H]$^+$.

Example 5: This example illustrates the preparation of 3-[4-(3,5-dimethylpyrazol-1-yl)phenyl]-5-(trifluoromethyl)-1,2,4-oxadiazole (Compound E-1 of Table E).

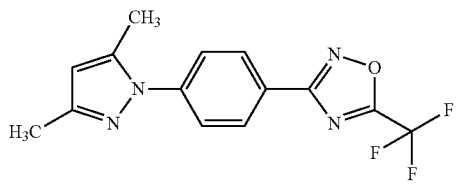 [SMILES: Cc1cc(C)n(-c2ccc(-c3noc(C(F)(F)F)n3)cc2)n1]

In a 100 mL three neck flask, equipped with a stirrer, a condenser and a bubbler was dissolved 4-(3,5-dimethylpyrazol-1-yl)benzonitrile (500 mg, 2.53 mmol) in ethanol (44 mL). Triethylamine (0.72, 5.07 mmol) was added followed by the addition of hydroxylamine hydrochloride (356 mg, 5.07 mmol) in small portions. The reaction mixture was stirred under reflux for 3.5 hours and then evaporated to dryness to give 4-(3,5-dimethylpyrazol-1-yl)-N'-hydroxybenzamidine. In a 100 ml. three-neck round bottom flask, the crude 4-(3,5-dimethylpyrazol-1-yl)-N'-hydroxy-benzamidine was suspended in tetrahydrofuran (22 mL) and pyridine (0.83 mL, 10.14 mmol). The resulting mixture was cooled to 5° C. and then trifluoroacetic anhydride was added dropwise (1.07 mL, 7.6 mmol). The white suspension was allowed to warm to room temperature and was stirred overnight. The reaction mixture was evaporated under vacuum and the yellow oil obtained was mixed with water and extracted with ethyl acetate. The organic phase was washed twice with water and once with brine, dried over sodium sulfate, filtered and evaporated under reduced pressure. The crude product was purified by flash chromatography over silica gel and then the oil obtained was dissolved in ethyl acetate, washed with 1N NaOH and brine, dried over sodium sulfate, filtered and evaporated under reduced pressure to give 3-[4-(3,5-dimethylpyrazol-1-yl)phenyl]-5-(trifluoromethyl)-1,2,4-oxadiazole as a yellow oil.

$^1$H NMR (400 MHz, CDCl$_3$) δ ppm: 2.32 (s, 3H), 2.40 (s, 3H), 6.05 (s, 1H), 7.64 (d, J=8.4 Hz, 2H), 8.21 (d, J=8.4 Hz, 2H).

LC/MS (Method A) retention time=1.12 min; 309 [M+H]$^+$.

mp: 109-111° C.

Example 6: This example illustrates the preparation of methyl 3-[4-[5-(trifluoromethyl)-1,2,4-oxadiazol-3-yl]phenyl]-4,5-dihydroisoxazole-5-carboxylate (Compound A-8 of Table A)

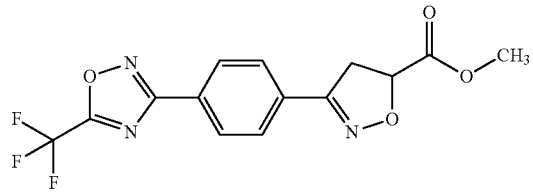 [SMILES: COC(=O)C1CC(c2ccc(-c3noc(C(F)(F)F)n3)cc2)=NO1]

Step 1: Preparation of 4-[5-(trifluoromethyl)-1,2,4-oxadiazol-3-yl]benzaldehyde oxime

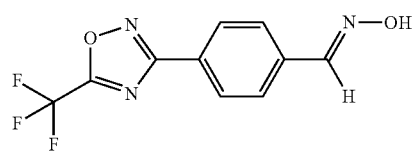

4-[5-(trifluoromethyl)-1,2,4-oxadiazol-3-yl]benzaldehyde (10 g, 37.167 mmol) was dissolved in a mixture of ethanol (100 mL) and triethylamine (8.90 ml, 63.184 mmol). Hydroxylamine hydrochloride (3.87 g, 55.751 mmol) was then added and the resulting mixture was stirred overnight at room temperature. The reaction mixture was evaporated and the crude residue obtained was purified over silica gel to give 4-[5-(trifluoromethyl)-1,2,4-oxadiazol-3-yl]benzaldehyde oxime.

LC/MS (Method B) retention time=1.46 min; 258 [M+H]$^+$.

Step 2: Synthesis of methyl 3-[4-[5-(trifluoromethyl)-1,2,4-oxadiazol-3-yl]phenyl]-4,5-dihydroisoxazole-5-carboxylate To a solution of 4-[5-(trifluoromethyl)-1,2,4-oxadiazol-3-yl]benzaldehyde oxime (175 mg, 0.68 mmol) and methyl acrylate (0.074 mL, 0.816 mmol) in methanol (3 mL) was added TFA (0.005 mL, 0.06 mmol), following by addition of (diacetoxyiodo)benzene (263 mg, 0.816 mmol) in 3 portions over a period of 30 min at room temperature. The suspension was stirred 1 hour at room temperature and then concentrated under reduced pressure. The crude residue was purified by flash chromatography to give methyl 3-[4-[5-(trifluoromethyl)-1,2,4-oxadiazol-3-yl]phenyl]-4,5-dihydroisoxazole-5-carboxylate as yellow crystals.

LC/MS (Method B) retention time=1.63 min; 342 [M+H]$^+$.

Example 7: This example illustrates the preparation of 3-[4-[5-(ethoxymethyl)isoxazol-3-yl]phenyl]-5-(trifluoromethyl)-1,2,4-oxadiazole (Compound C-5 of Table C).

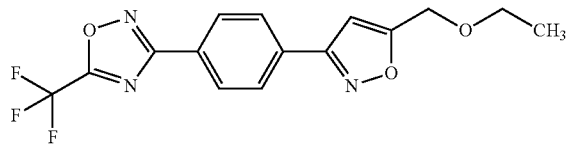 [SMILES: CCOCc1cc(-c2ccc(-c3noc(C(F)(F)F)n3)cc2)no1]

To a solution of 4-[5-(trifluoromethyl)-1,2,4-oxadiazol-3-yl]benzaldehyde oxime (175 mg, 0.680 mmol) and 3-ethoxyprop-1-yne (0.083 ml, 0.82 mmol) in methanol (3 mL) at rt was added TFA (0.005 mL, 0.06 mmol), following by addition of (diacetoxyiodo)benzene (263 mg, 0.197 mmol) in 3 portions over a period of 30 min. The suspension was stirred 1 hour at room temperature. The white suspension was concentrated and dried under vacuum. The crude residue was purified by flash chromatography to 3-[4-[5-(ethoxymethyl)phenyl]-5-(trifluoromethyl)-1,2,4-oxadiazole.

$^1$H NMR (400 MHz, CHLOROFORM-d) δ ppm 1.25-1.32 (t, 3H) 3.66 (qd, J=6.97, 1.10 Hz, 2H) 4.67 (d, J=2.57 Hz, 2H) 6.66 (d, J=7.70 Hz, 1H) 7.98 (d, J=8.44 Hz, 1H) 8.03 (d, J=8.44 Hz, 1H) 8.22 (d, J=8.44 Hz, 1H) 8.29 (d, J=8.44 Hz, 1H).

LC/MS (Method B) retention time=1.92 min; 340 [M+H]$^+$.

Example 8: This example illustrates the preparation of 3-[4-(5-cyclopropylisoxazol-3-yl)phenyl]-5-(trifluoromethyl)-1,2,4-oxadiazole (Compound C-7 of Table C).

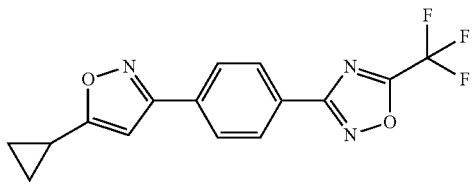 [SMILES: FC(F)(F)c1nc(-c2ccc(-c3cc(C4CC4)on3)cc2)no1]

To a solution of [5-(trifluoromethyl)-1,2,4-oxadiazol-3-yl]benzaldehyde oxime (175 mg, 0.680 mmol) and cyclopropylacetylene (0.069 mL, 0.816 mmol) in methanol (3 mL) at rt was added TFA (0.005 mL, 0.06 mmol), followed by addition of (diacetoxyiodo)benzene (263 mg, 0.197 mmol) in 3 portions over a period of 30 min. The suspension was stirred 1 hour at room temperature. The white suspension was concentrated and dried under vacuum. The crude was purified with the flash chromatography to give 3-[4-(5-cyclopropylisoxazol-3-yl)phenyl]-5-(trifluoromethyl)-1,2,4-oxadiazole as a light yellow solid.

$^1$H NMR (400 MHz, CDCl$_3$) δ ppm: 1.01-1.09 (m, 2H) 1.10-1.17 (m, 2H) 2.07-2.17 (m, 1H) 6.30 (s, 1H) 7.99 (d, J=8.4 Hz, 2H) 8.27 (d, J=8.4 Hz, 2H).

LC/MS (Method B) retention time=1.98 min; 322 [M+H]$^+$.

Example 9: This example illustrates the preparation 5,5-dimethyl-2-[4-[5-(trifluoromethyl)-1,2,4-oxadiazol-3-yl]phenyl]-1,3-oxazinan-4-one (Compound A-10 of Table A).

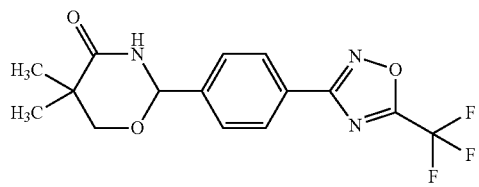 [SMILES: CC1(C)COC(c2ccc(-c3noc(C(F)(F)F)n3)cc2)NC1=O]

Step 1: Preparation of N'-hydroxy-4-methyl-benzamidine

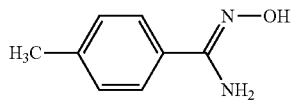

To a stirred suspension of 4-methylbenzonitrile (35 g, 0.29 mol) in ethanol (220 mL) and water (440 mL) at rt was added hydroxylamine hydrochloride (41.1 g, 0.58 mol), potassium carbonate (65.4 g, 0.47 mol) and 8-hydroxyquinoline (0.22 g, 1.5 mmol). The reaction mixture was heated at 80° C. for 4 hours. The mixture was cooled to rt and diluted with 2N HCl until pH 8. Ethanol was evaporated under reduced pressure. The mixture was filtered, washed with water and dried under vacuum to afford the title compound.

LC/MS (Method A) retention time=0.23 minutes, 151.0 (M+H).

Step 2: Preparation of 3-(p-tolyl)-5-(trifluoromethyl)-1,2,4-oxadiazole

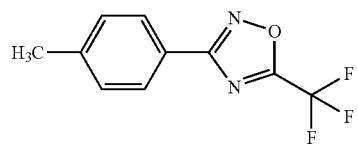 [SMILES: Cc1ccc(-c2noc(C(F)(F)F)n2)cc1]

To a stirred solution of N'-hydroxy-4-methyl-benzamidine (38.7 g, 0.25 mol) in 2-methyltetrahydrofuran (750 mL) was added TFAA at 0° C. The reaction mixture was stirred at 15° C. for two hours and then diluted with water. The organic layer was separated, washed successively with sodium bicarbonate solution, ammonium chloride solution and water, dried over sodium sulfate, filtered and evaporated to dryness. The crude product was purified by flash chromatography over silica gel (750 g pre-packed column) with heptane/EtOAc 99:1 to 90:10 to afford the title compound as a clear oil, which solidified upon storage.

$^1$H NMR (400 MHz, CDCl$_3$) δ ppm: 8.00 (d, 2H), 7.32 (d, 2H), 2.45 (s, 3H).

$^{19}$F NMR (400 MHz, CDCl$_3$) δ ppm: −65.41 (s).

LC/MS (Method A) retention time=1.15 minutes, mass not detected.

Step 3a: Preparation of 3-[4-(bromomethyl)phenyl]-5-(trifluoromethyl)-1,2,4-oxadiazole

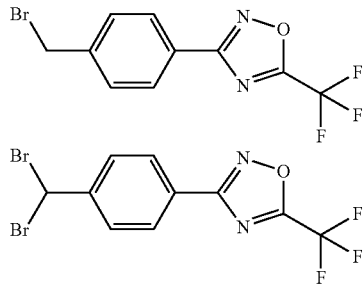

A stirred mixture of 3-(p-tolyl)-5-(trifluoromethyl)-1,2,4-oxadiazole (56.0 g, 0.24 mol) and NBS (45.4 g, 0.25 mol) in tetrachloromethane (480 mL) under argon was heated to 70° C. AIBN (4.03 g, 24 mmol) was added and the reaction mixture stirred at 65° C. for 18 hours. The mixture was cooled to rt and diluted with dichloromethane and water. Layers were separated. The organic layer was washed with a sodium bicarbonate solution, dried over sodium sulfate, filtered and evaporated to dryness. The crude residue was purified by flash chromatography over silica gel (750 g pre-packed column) with cyclohexane/EtOAc 100:0 to 95:5 to afford 3-[4-(bromomethyl)phenyl]-5-(trifluoromethyl)-1,2,4-oxadiazole as a white solid mp: 58-63° C.

$^1$H NMR (400 MHz, CDCl$_3$) δ ppm: 8.11 (d, 2H), 7.55 (d, 2H), 4.53 (s, 2H).

$^{19}$F NMR (400 MHz, CDCl$_3$) δ ppm: −65.32 (s).

The byproduct 3-[4-(dibromomethyl)phenyl]-5-(trifluoromethyl)-1,2,4-oxadiazole was also isolated from the reaction mixture and obtained as a white solid mp: 61-66° C.

$^1$H NMR (400 MHz, CDCl$_3$) δ ppm: 8.15 (d, 2H), 7.73 (d, 2H), 6.68 (s, 1H).

$^{19}$F NMR (400 MHz, CDCl$_3$) δ ppm: −65.34 (s).

Step 3b: Preparation of 3-[4-(bromomethyl)phenyl]-5-(trifluoromethyl)-1,2,4-oxadiazole from 3-[4-(dibromomethyl)phenyl]-5-(trifluoromethyl)-1,2,4-oxadiazole

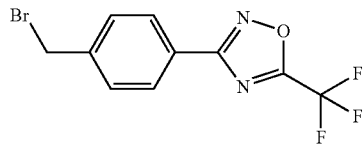 [SMILES: FC(F)(F)c1nc(-c2ccc(CBr)cc2)no1]

To a stirred 1:9 ratio mixture of 3-[4-(bromomethyl)phenyl]-5-(trifluoromethyl)-1,2,4-oxadiazole and 3-[4-(dibromomethyl)phenyl]-5-(trifluoromethyl)-1,2,4-oxadiazole (10.2 g) in acetonitrile (95 mL), water (1.9 mL) and DIPEA (6.20 ml, 35.7 mmol) was added diethylphosphite (4.7 mL, 35.7 mmol) at 5° C. The mixture was stirred at 5-10° C. for two hours, water and 1M HCl were added and acetonitrile evaporated under reduced pressure. The white aqueous slurry was extracted three times with dichloromethane. The combined organic layers were dried over sodium sulfate, and filtered. The solvent was removed under reduced pressure and the resultant crude residue subjected to flash chromatography over silica gel (40 g pre-packed column) with cyclohexane/EtOAc 99:1 to 9:1 to afford 3-[4-(bromomethyl)phenyl]-5-(trifluoromethyl)-1,2,4-oxadiazole.

$^1$H NMR (400 MHz, CDCl$_3$) δ ppm: 8.11 (d, 2H), 7.55 (d, 2H), 4.53 (s, 2H).

$^{19}$F NMR (400 MHz, CDCl$_3$) δ ppm: −65.32 (s).

Step 4: Preparation of 5,5-dimethyl-2-[4-[5-(trifluoromethyl)-1,2,4-oxadiazol-3-yl]phenyl]-1,3-oxazinan-4-one A white suspension of 3-[4-(bromomethyl)phenyl]-5-(trifluoromethyl)-1,2,4-oxadiazole (100 mg, 0.31 mmol), 4,4-dimethylisoxazolidin-3-one (1.5 equiv., 0.46 mmol) and potassium carbonate (2 equiv., 0.62 mmol) in acetonitrile (3.0 mL) was heated in a microwave oven for 30 minutes at 120° C. Solids were removed by filtration and washed with ethyl acetate. The solvents were removed under reduced pressure and the resultant residue was subjected to flash chromatography over silica gel with (EtOAc:cyclohexane eluent gradient 0:1 to 2:8) to afford 5,5-dimethyl-2-[4-[5-(trifluoromethyl)-1,2,4-oxadiazol-3-yl]phenyl]-1,3-oxazinan-4-one as a yellow solid.

$^1$H NMR (600 MHz, CDCl$_3$) δ ppm: 1.21 (s, 3H) 1.42 (s, 3H) 3.81 (d, J=11.6 Hz, 1H) 3.86 (d, J=11.6 Hz, 1H) 5.88 (s, 1H) 6.31 (br. s, 1H) 7.64 (d, J=8.4 Hz, 2H) 8.19 (d, J=8.4 Hz, 2H).

$^{13}$C NMR (151 MHz, CDCl$_3$) δ ppm: 21.1 (s, 1C) 25.6 (s, 1C) 39.2 (s, 1C) 75.3 (s, 1C) 85.9 (s, 1C) 115.9 (q, J=274 Hz, 1C) 126.3 (s, 1C) 127.5 (s, 1C) 128.3 (s, 1C) 142.0 (s, 1C) 166.0 (q, J=44 Hz, 1C) 168.6 (s, 1C) 175.5 (s, 1C).

LC/MS (Method A) retention time=0.99 min; 342 [M+H]$^+$.

mp: 187-187.3° C.

Example 10: This example illustrates the preparation N-[2-[3-fluoro-4-[5-(trifluoromethyl)-1,2,4-oxadiazol-3-yl]phenyl]-4,5-dihydrothiazol-4-yl]cyclopropanecarboxamide (Compound A-22 of Table A).

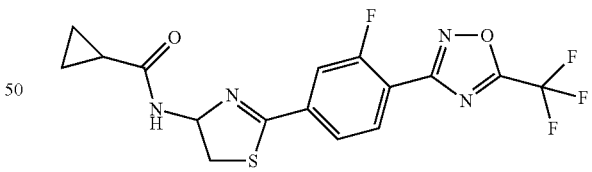

Step 1: Preparation of 3-fluoro-4-[5-(trifluoromethyl)-1,2,4-oxadiazol-3-yl]benzenecarbothioamide

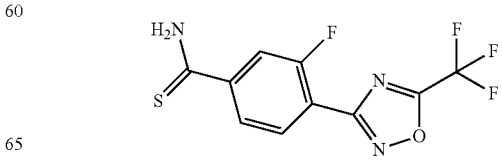

This compound was prepared from 3-fluoro-4-[5-(trifluoromethyl)-1,2,4-oxadiazol-3-yl]benzoic acid (CAS 2036333-66-9) by methods known per se. Thus, a suspension of 3-fluoro-4-[5-(trifluoromethyl)-1,2,4-oxadiazol-3-yl]benzamide (822 mg) in toluene (30 mL) was purged with argon and 2,4-bis(4-methoxyphenyl)-1,3,2,4-dithiadiphosphetane-2,4-disulfide (Lawesson's reagent, 906 mg) was added. The resulting reaction mixture was heated to 100° C. for 10 min, resulting in a dark yellow solution. The mixture was then allowed to cool to ambient temperature and extracted with saturated aqueous sodium bicarbonate (10 mL) and ethyl acetate (10 mL). The organic phase was dried over anhydrous magnesium sulfate and the solvent evaporated. The residue was purified by chromatography on silica gel using a dichloromethane/methanol gradient to afford 3-fluoro-4-[5-(trifluoromethyl)-1,2,4-oxadiazol-3-yl]benzenecarbothioamide (540 mg, 62%) as a yellow solid.

$^1$H NMR (400 MHz, CDCl$_3$) δ ppm: 7.20 (s, broad, 1H), 7.70 (s, broad, 1H), 7.73 (dd, 1H), 7.80 (dd, 1H), 8.15 (t, 1H).

LC/MS (Method A) retention time=0.97 min; 292 [M+H]$^+$.

Mp: 139-142° C.

Step 1a: Preparation of (2-tert-butylsulfinyliminoethyl) 4-methylbenzenesulfonate

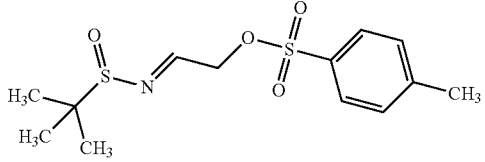 [SMILES: Cc1ccc(S(=O)(=O)OC/C=N/S(=O)C(C)(C)C)cc1]

This compound was prepared from 2-oxoethyl 4-methylbenzenesulfonate (CAS 172328-35-7) by methods known per se. Thus, to a suspension of 2-methylpropane-2-sulfinamide (4.17 g) and anhydrous copper (II) sulfate (16.1 g) in dichloromethane (250 mL) was added dropwise a solution of 2-oxoethyl 4-methylbenzenesulfonate (7.15 g). The mixture was stirred 18 hours at ambient temperature. Then, the mixture was filtered through celite and the filtrate was evaporated. The residue was purified by chromatography on silica gel using a gradient cyclohexane/ethyl acetate (0% to 40%) to afford (2-tert-butylsulfinyliminoethyl) 4-methylbenzenesulfonate (6.13 g, 58% yield) as a white solid.

$^1$H NMR (400 MHz, CDCl$_3$) δ ppm: 1.17 (s, 9H), 2.46 (s, 3H), 4.88 (d, 2H), 7.37 (d, 2H), 7.82 (d, 2H), 7.95 (t, 1H).

LC/MS (Method A) retention time=0.95 min; 318 [M+H]$^+$.

Step 2: Preparation of N-[2-[3-fluoro-4-[5-(trifluoromethyl)-1,2,4-oxadiazol-3-yl]phenyl]-4,5-dihydrothiazol-4-yl]-2-methyl-propane-2-sulfinamide (Compound A-26 of Table A)

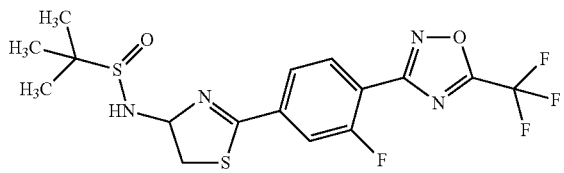 [SMILES: CC(C)(C)S(=O)NC1CSC(c2ccc(-c3noc(C(F)(F)F)n3)c(F)c2)=N1]

To a solution of (2-tert-butylsulfinyliminoethyl) 4-methylbenzenesulfonate (1.07 g) in acetonitrile (15.1 mL) was added 3-fluoro-4-[5-(trifluoromethyl)-1,2,4-oxadiazol-3-yl]benzenecarbothioamide (0.992 g), potassium iodide (0.560 g) and potassium bicarbonate (0.675 g). The mixture was stirred at ambient temperature for 1 h. Then water was added to the mixture, extracted with ethyl acetate and the organic phase dried over anhydrous sodium sulfate. The solvent was evaporated and the residue was purified by chromatography on silica gel using a cyclohexane/ethyl acetate gradient to afford N-[2-[3-fluoro-4-[5-(trifluoromethyl)-1,2,4-oxadiazol-3-yl]phenyl]-4,5-dihydro-thiazol-4-yl]-2-methyl-propane-2-sulfinamide (0.66 g, 45% yield) as a yellow gum.

$^1$H NMR (400 MHz, CDCl$_3$) δ ppm: 1.26 (s, 9H), 3.42 (dd, 1H), 3.77 (dd, 1H), 4.00 (d, 1H), 6.05 (q, 1H), 7.82 (m, 2H), 8.15 (t, 1H).

LC/MS (Method A) retention time=1.09 min; 437 [M+H]$^+$.

Step 3: Preparation of 2-[3-fluoro-4-[5-(trifluoromethyl)-1,2,4-oxadiazol-3-yl]phenyl]-4,5-dihydrothiazol-4-amine

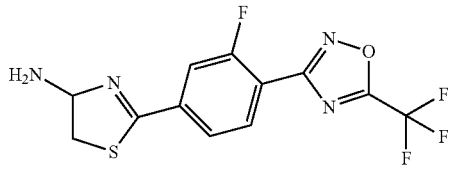 [SMILES: NC1CSC(c2ccc(-c3noc(C(F)(F)F)n3)c(F)c2)=N1]

To a solution of N-[2-[3-fluoro-4-[5-(trifluoromethyl)-1,2,4-oxadiazol-3-yl]phenyl]-4,5-dihydro-thiazol-4-yl]-2-methyl-propane-2-sulfinamide (662 mg) in methanol (40.0 mL) was added dropwise hydrogen chloride (4M in dioxane, 8.65 mL) at 0° C. The mixture was stirred at at 0° C. for 4 hours. Then, saturated aqueous sodium bicarbonate (10 mL) was added and the aqueous phase was extracted three times with dichloromethane. The combined organic phase was washed with brine, dried over anhydrous sodium sulfate and evaporated. The residue was purified by chromatography on silica gel using a dichloromethane/methanol gradient to afford 2-[3-fluoro-4-[5-(trifluoromethyl)-1,2,4-oxadiazol-3-yl]phenyl]-4,5-dihydrothiazol-4-amine (0.43 mg, 85% yield) as a brown oil.

$^1$H NMR (400 MHz, CDCl$_3$) δ ppm: 2.06 (s, broad, 2H), 3.25 (dd, 1H), 3.73 (dd, 1H), 5.61 (t, 1H), 7.77 (m, 2H), 8.15 (t, 1H).

LC/MS (Method A) retention time=0.76 min; 333 [M+H]$^+$.

Step 4: Preparation of N-[2-[3-fluoro-4-[5-(trifluoromethyl)-1,2,4-oxadiazol-3-yl]phenyl]-4,5-dihydro-thiazol-4-yl]cyclopropanecarboxamide (Compound A-22 of Table A)

To a solution of 2-[3-fluoro-4-[5-(trifluoromethyl)-1,2,4-oxadiazol-3-yl]phenyl]-4,5-dihydro-thiazol-4-amine (70 mg) in dichloromethane (0.6 mL) was added cyclopropanecarbonyl chloride (22 mg) followed by triethylamine (64 mg). The reaction mixture was stirred for 18 hours at ambient temperature. Then the mixture was concentrated and the residue was purified by chromatography on silica gel using a cyclohexane/ethyl acetate gradient to afford N-[2-[3-fluoro-4-[5-(trifluoromethyl)-1,2,4-oxadiazol-3-yl]phenyl]-4,5-dihydro-thiazol-4-yl]cyclopropanecarboxamide (72.3 mg, 86% yield) as a white solid.

$^1$H NMR (400 MHz, CDCl$_3$) δ ppm: 0.80 (m, 2H), 1.03 (m, 2H), 1.38 (m, 1H), 3.33 (dd, 1H), 3.83 (dd, 1H), 6.25 (d, 1H), 6.55 (q, 1H), 7.80 (m, 2H), 8.17 (t, 1H).

LC/MS (Method A) retention time=1.04 min; 401 [M+H]$^+$.

Mp: 197-205° C.

Where necessary, enantiomerically pure final compounds may be obtained from racemic materials as appropriate via standard physical separation techniques, such as reverse phase chiral chromatography, or through stereoselective synthetic techniques, (eg, by using chiral starting materials).

TABLE A

Melting point (mp) and/or LC/MS data for compounds of Formula (I):

| Entry | Compound Name | Structure | $t_R$ (min) | [M + H]$^+$ (measured) | method | mp (° C) |
|---|---|---|---|---|---|---|
| A-1 | 3-[4-(4-methyl-4,5-dihydrooxazol-2-yl)phenyl]-5-(trifluoromethyl)-1,2,4-oxadiazole | 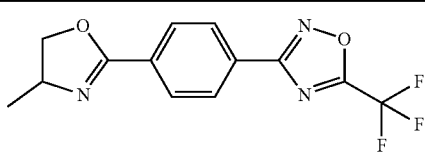 | | | | 77-80 |
| A-2 | 3-[4-(4,4-dimethyl-5H-oxazol-2-yl)phenyl]-5-(trifluoromethyl)-1,2,4-oxadiazole | 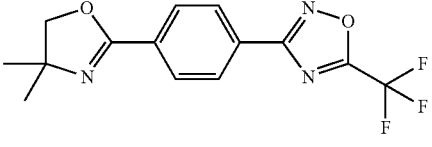 [SMILES: CC1(C)COC(c2ccc(-c3noc(C(F)(F)F)n3)cc2)=N1] | | | | 70-75 |
| A-3 | 3-[4-(4,5-dihydrooxazol-2-yl)phenyl]-5-(trifluoromethyl)-1,2,4-oxadiazole | 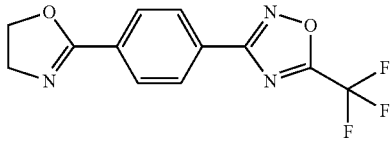 [SMILES: FC(F)(F)c1nc(-c2ccc(C3=NCCO3)cc2)no1] | | | | 120-125 |
| A-4 | 3-[4-(3-methyl-4,5-dihydroisoxazol-5-yl)phenyl]-5-(trifluoromethyl)-1,2,4-oxadiazole | 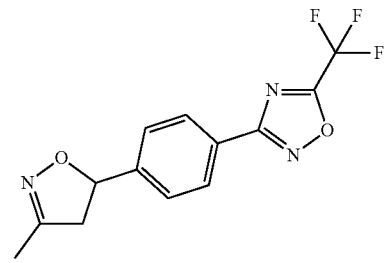 [SMILES: CC1=NOC(c2ccc(-c3noc(C(F)(F)F)n3)cc2)C1] | | | | 89-92 |
| A-5 | 3-[4-(3-ethyl-4,5-dihydroisoxazol-5-yl)phenyl]-5-(trifluoromethyl)-1,2,4-oxadiazole | 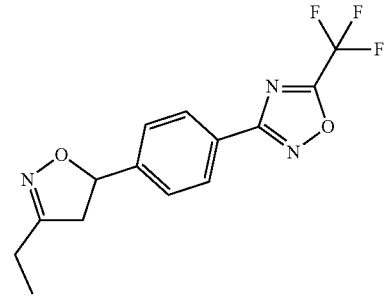 [SMILES: CCC1=NOC(c2ccc(-c3noc(C(F)(F)F)n3)cc2)C1] | | | | 75-80 |

TABLE A-continued

Melting point (mp) and/or LC/MS data for compounds of Formula (I):

| Entry | Compound Name | Structure | $t_R$ (min) | $[M + H]^+$ (measured) | method | mp (°C) |
|---|---|---|---|---|---|---|
| A-6 | 3-[4-(3-propyl-4,5-dihydroisoxazol-5-yl)phenyl]-5-(trifluoromethyl)-1,2,4-oxadiazole | 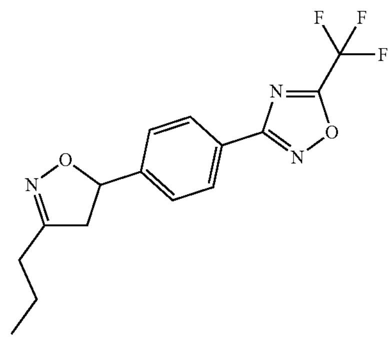 [SMILES: CCCC1=NOC(c2ccc(-c3noc(C(F)(F)F)n3)cc2)C1] | | | | 79-83 |
| A-7 | 3-[4-(3-cyclohexyl-4,5-dihydroisoxazol-5-yl)phenyl]-5-(trifluoromethyl)-1,2,4-oxadiazole | 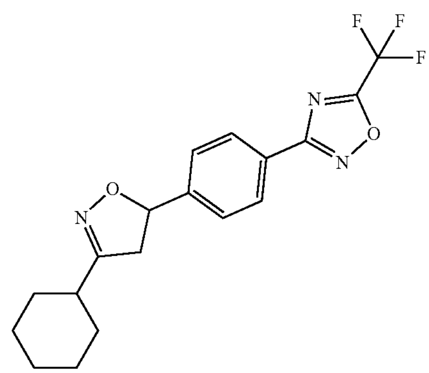 [SMILES: FC(F)(F)c1nc(-c2ccc(C3CC(C4CCCCC4)=NO3)cc2)no1] | | | | 79-82 |
| A-8 | methyl 3-[4-[5-(trifluoromethyl)-1,2,4-oxadiazol-3-yl]phenyl]-4,5-dihydroisoxazole-5-carboxylate | 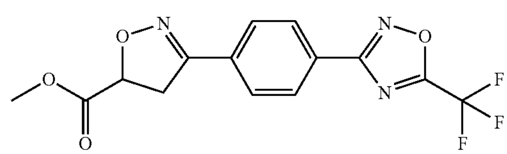 [SMILES: COC(=O)C1CC(c2ccc(-c3noc(C(F)(F)F)n3)cc2)=NO1] | 1.63 | 242 | B | |
| A-9 | 3-[4-[3-(methoxymethyl)-4,5-dihydroisoxazol-5-yl]phenyl]-5-(trifluoromethyl)-1,2,4-oxadiazole | 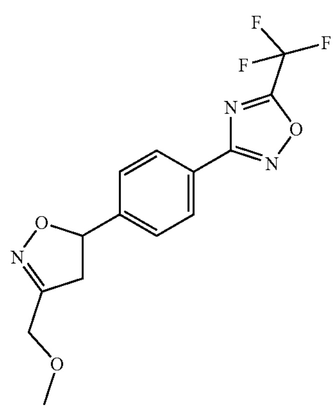 [SMILES: COCC1=NOC(c2ccc(-c3noc(C(F)(F)F)n3)cc2)C1] | | | | 59-63 |
| A-10 | 5,5-dimethyl-2-[4-(5-(trifluoromethyl)-1,2,4-oxadiazol-3-yl]phenyl]-1,3-oxazinan-4-one | 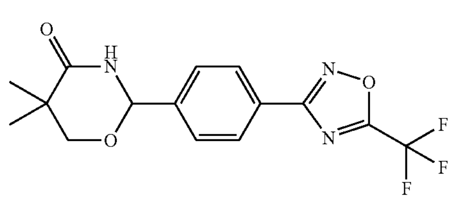 [SMILES: CC1(C)COC(c2ccc(-c3noc(C(F)(F)F)n3)cc2)NC1=O] | | | | 187.3-189 |

TABLE A-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| A-11 | 6,6-dimethyl-2-[4-[5-(trifluoromethyl)-1,2,4-oxadiazol-3-yl]phenyl]-1,3-oxazinan-4-one | 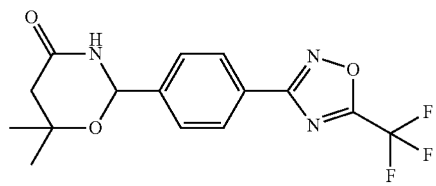 [SMILES: CC1(C)CC(=O)NC(c2ccc(-c3noc(C(F)(F)F)n3)cc2)O1] | 1.03 | 342.2 | A | |
| A-12 | 3-[4-(3-cyclopropyl-4,5-dihydroisoxazol-5-yl)phenyl]-5-(trifluoromethyl)-1,2,4-oxadiazole | 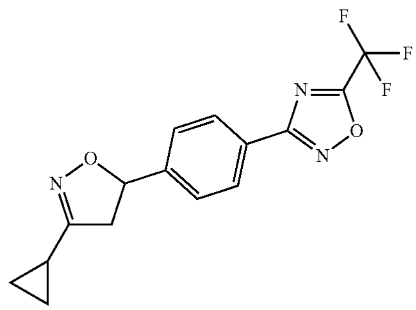 [SMILES: FC(F)(F)c1nc(-c2ccc(C3CC(C4CC4)=NO3)cc2)no1] | | | | 109-112 |
| A-13 | 3-[4-(3,5-dimethyl-4H-isoxazol-5-yl)phenyl]-5-(trifluoromethyl)-1,2,4-oxadiazole | 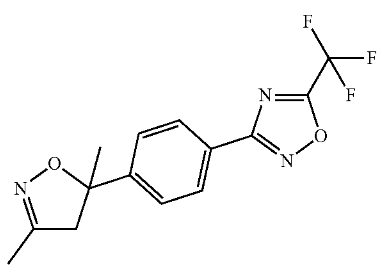 [SMILES: CC1=NOC(C)(c2ccc(-c3noc(C(F)(F)F)n3)cc2)C1] | 1.07 | 312 | A | |
| A-14 | 5-(trifluoromethyl)-3-[4-[3-(trifluoromethyl)-4,5-dihydroisoxazol-5-yl]phenyl]-1,2,4-oxadiazole | 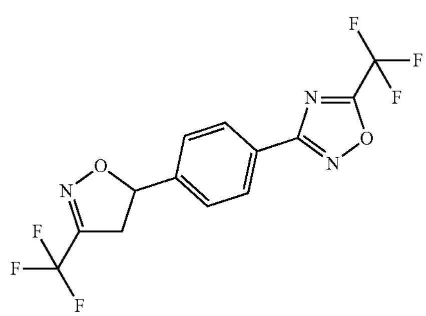 [SMILES: FC(F)(F)C1=NOC(c2ccc(-c3noc(C(F)(F)F)n3)cc2)C1] | | | | 65-69 |
| A-15 | 2-[3-fluoro-4-[5-(trifluoromethyl)-1,2,4-oxadiazol-3-yl]phenyl]-1,3-oxazinan-4-one | 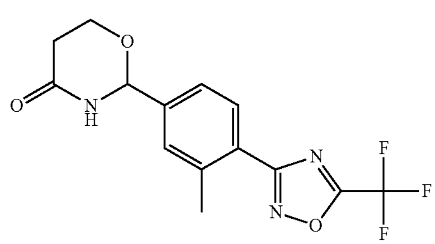 [SMILES: Cc1cc(C2NC(=O)CCO2)ccc1-c1noc(C(F)(F)F)n1] | | | | 142-146 |

TABLE A-continued

Melting point (mp) and/or LC/MS data for compounds of Formula (I):

| Entry | Compound Name | Structure | $t_R$ (min) | [M + H]+ (measured) | method | mp (° C) |
|---|---|---|---|---|---|---|
| A-16 | 3-[4-(3-bromo-4,5-dihydroisoxazol-5-yl)phenyl]-5-(trifluoromethyl)-1,2,4-oxadiazole | 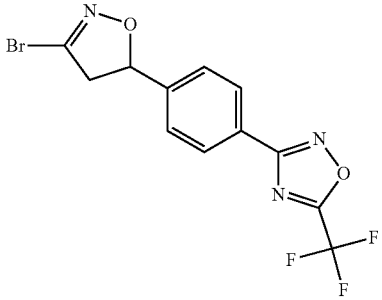 [SMILES: FC(F)(F)c1nc(-c2ccc(C3CC(Cl)=NO3)cc2)no1] | 1.11 | 362 & 364 | A | |
| A-17 | 3-[4-(3-chloro-4,5-dihydroisoxazol-5-yl)phenyl]-5-(trifluoromethyl)-1,2,4-oxadiazole | 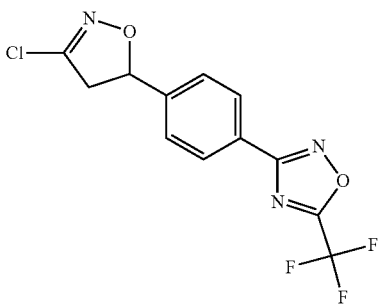 | 1.80 | 318 | B | |
| A-18 | 3-[4-(3-methoxy-4,5-dihydroisoxazol-5-yl)phenyl]-5-(trifluoromethyl)-1,2,4-oxadiazole | 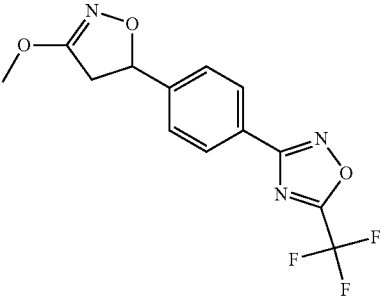 [SMILES: COC1=NOC(c2ccc(-c3noc(C(F)(F)F)n3)cc2)C1] | 1.04 | 314 | A | |
| A-19 | 3-[4-(3-ethoxy-4,5-dihydroisoxazol-5-yl)phenyl]-5-(trifluoromethyl)-1,2,4-oxadiazole | 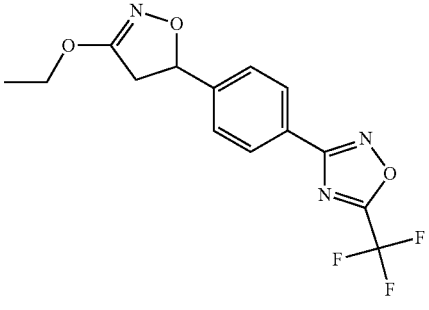 [SMILES: CCOC1=NOC(c2ccc(-c3noc(C(F)(F)F)n3)cc2)C1] | 1.10 | 328 | A | |
| A-20 | 3-[4-[3-(2,2,2-trifluoroethoxy)-4,5-dihydroisoxazol-5-yl]phenyl]-5-(trifluoromethyl)-1,2,4-oxadiazole | 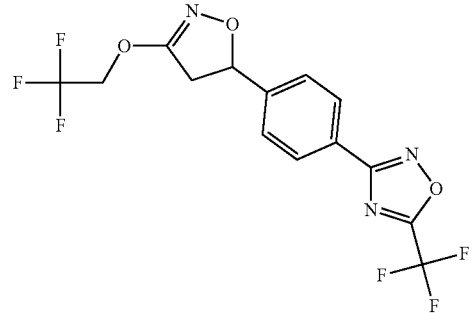 [SMILES: FC(F)(F)COC1=NOC(c2ccc(-c3noc(C(F)(F)F)n3)cc2)C1] | 1.14 | 382 | A | |

TABLE A-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| A-21 | 3-[4-(5,5-dimethyl-4H-oxazol-2-yl)phenyl]-5-(trifluoromethyl)-1,2,4-oxadiazole | 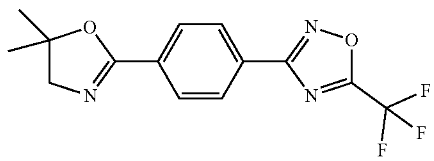 [SMILES: CC1(C)CN=C(c2ccc(-c3noc(C(F)(F)F)n3)cc2)O1] | | | | 178-180 |
| A-22 | N-[2-[3-fluoro-4-[5-(trifluoromethyl)-1,2,4-oxadiazol-3-yl]phenyl]-4,5-dihydrothiazol-4-yl]cyclopropane-carboxamide | 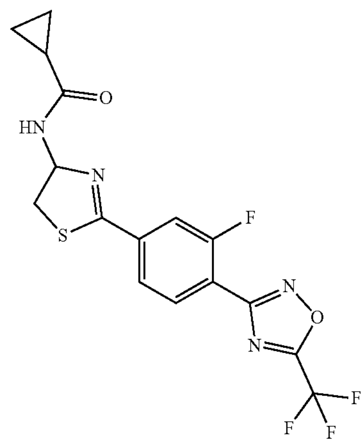 [SMILES: O=C(NC1CSC(c2ccc(-c3noc(C(F)(F)F)n3)c(F)c2)=N1)C1CC1] | | | | 197-205 |
| A-23 | N-[2-[3-fluoro-4-[5-(trifluoromethyl)-1,2,4-oxadiazol-3-yl]phenyl]-4,5-dihydrothiazol-4-yl]-2-methyl-benzamids | 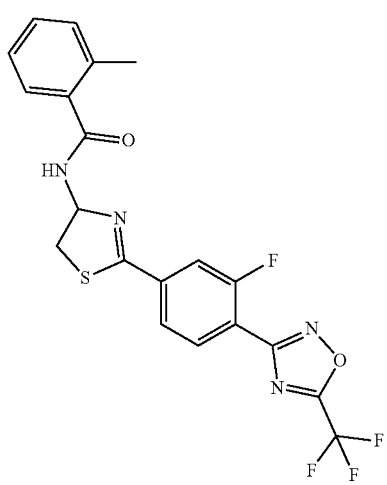 [SMILES: Cc1ccccc1C(=O)NC1CSC(c2ccc(-c3noc(C(F)(F)F)n3)c(F)c2)=N1] | | | | 144-155 |

TABLE A-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| A-24 | N-[2-[3-fluoro-4-[5-(trifluoromethyl)-1,2,4-oxadiazol-3-yl]phenyl]-4,5-dihydrothiazol-4-yl]-N',N'-dimethyl-oxamide | 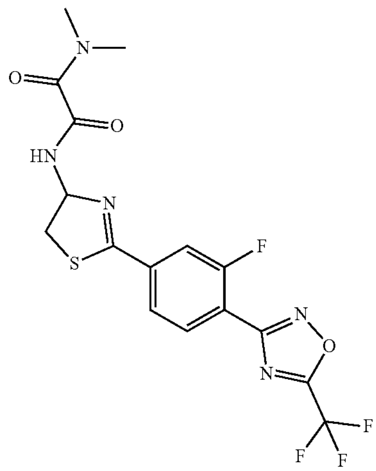 [SMILES: CN(C)C(=O)C(=O)NC1CSC(c2ccc(-c3noc(C(F)(F)F)n3)c(F)c2)=N1] | | | | 120-165 |
| A-25 | N-[2-[3-fluoro-4-[5-(trifluoromethyl)-1,2,4-oxadiazol-3-yl]phenyl]-4,5-dihydrothiazol-4-yl]-2-methoxy-acetamide | 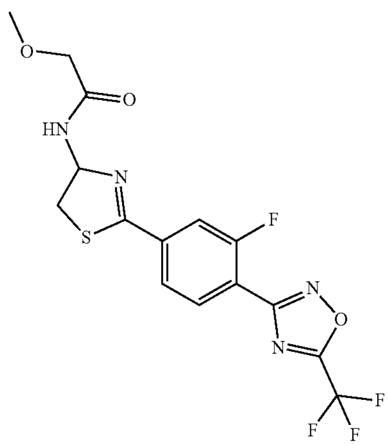 [SMILES: COCC(=O)NC1CSC(c2ccc(-c3noc(C(F)(F)F)n3)c(F)c2)=N1] | | | | 141-175 |
| A-26 | N-[2-[3-fluoro-4-[5-(trifluoromethyl)-1,2,4-oxadiazol-3-yl]phenyl]-4,5-dihydrothiazol-4-yl]-2-methyl-propane-2-sulfinamide | 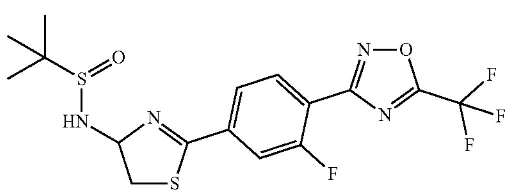 [SMILES: CC(C)(C)S(=O)NC1CSC(c2ccc(-c3noc(C(F)(F)F)n3)c(F)c2)=N1] | 1.09 | 437 | A | |
| A-27 | N-[2-[4-[5-(trifluoromethyl)-1,2,4-oxadiazol-3-yl]phenyl]-4,5-dihydrothiazol-4-yl]cyclopropane-carboxamide | 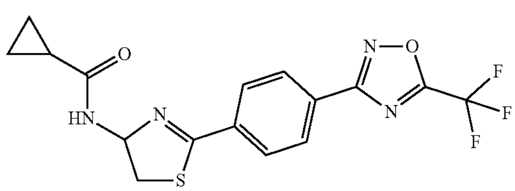 [SMILES: O=C(NC1CSC(c2ccc(-c3noc(C(F)(F)F)n3)cc2)=N1)C1CC1] | 1.04 | 383 | A | |
| A-28 | 2-methoxy-N-(2-[4-[5-(trifluoromethyl)-1,2,4-oxadiazol-3-yl]phenyl]-4,5-dihydrothiazol-4-yl]acetamide | 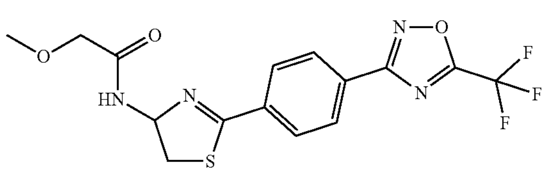 [SMILES: COCC(=O)NC1CSC(c2ccc(-c3noc(C(F)(F)F)n3)cc2)=N1] | 1.02 | 387 | A | |

TABLE A-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| A-29 | 2-methyl-N-[2-[4-[5-(trifluoromethyl)-1,2,4-oxadiazol-3-yl]phenyl]-4,5-dihydrothiazol-4-yl]propane-2-sulfinamide | 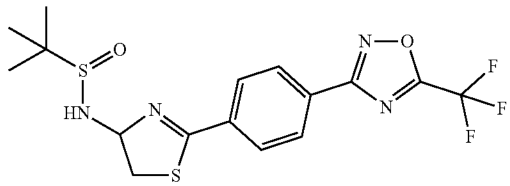 [SMILES: CC(C)(C)S(=O)NC1CSC(c2ccc(-c3noc(C(F)(F)F)n3)cc2)=N1] | 1.09 | 419 | A | |
| A-30 | 3-[4-(1-methylsulfonyl-pyrrolidin-2-yl)phenyl]-5-(trifluoromethyl)-1,2,4-oxadiazole | 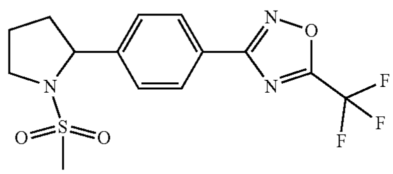 [SMILES: CS(=O)(=O)N1CCCC1c1ccc(-c2noc(C(F)(F)F)n2)cc1] | | | | 117.7-118.6 |
| A-31 | N-methoxy-N-methyl-2-[4-[5-(trifluoromethyl)-1,2,4-oxadiazol-3-yl]phenyl]pyrrolidine-1-carboxamide | 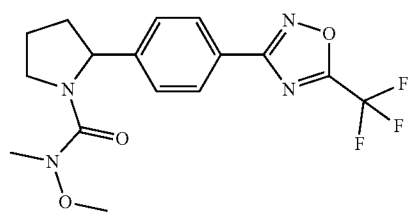 [SMILES: CON(C)C(=O)N1CCCC1c1ccc(-c2noc(C(F)(F)F)n2)cc1] | 1.09 | 371 | A | |
| A-32 | methyl 2-[4-[5-(trifluoromethyl)-1,2,4-oxadiazol-3-yl]phenyl]pyrrolidine-1-carboxylate | 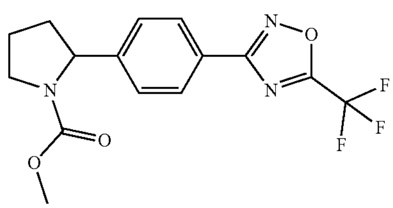 [SMILES: COC(=O)N1CCCC1c1ccc(-c2noc(C(F)(F)F)n2)cc1] | 1.13 | 342 | A | |
| A-33 | 2-methoxy-1-[2-[4-[5-(trifluoromethyl)-1,2,4-oxadiazol-3-yl]phenyl]pyrrolidin-1-yl]ethanone | 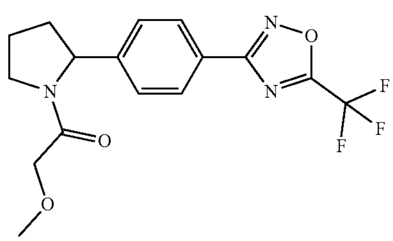 [SMILES: COCC(=O)N1CCCC1c1ccc(-c2noc(C(F)(F)F)n2)cc1] | 1.00 | 356 | A | |
| A-34 | 3-(4-pyrrolidin-1-ium-2-ylphenyl)-5-(trifluoromethyl)-1,2,4-oxadiazole; chloride | 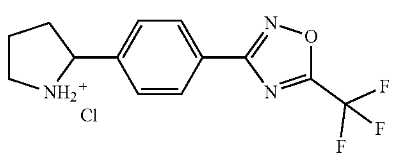 [SMILES: FC(F)(F)c1nc(-c2ccc(C3CCCN3)cc2)no1 ; Cl] | | | | 154.4-158.5 |
| A-35 | imidazol-1-yl-[2-[4-[5-(trifluoromethyl)-1,2,4-oxadiazol-3-yl]phenyl]pyrrolidin-1-yl]methanone | 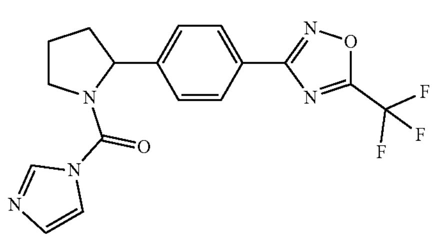 [SMILES: O=C(N1CCCC1c1ccc(-c2noc(C(F)(F)F)n2)cc1)n1ccnc1] | 0.92 | 378 | A | |

TABLE A-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| A-36 | cyclopropyl-[2-[4-[5-(trifluoromethyl)-1,2,4-oxadiazol-3-yl]phenyl]pyrrolidin-1-yl]methanone | 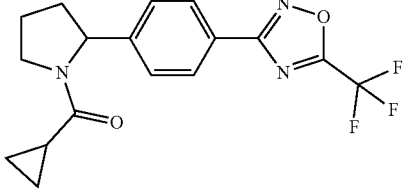 | 1.08 | 352 | A | |
| A-37 | 1-[2-[4-[5-(trifluoromethyl)-1,2,4-oxadiazol-3-yl]phenyl]pyrrolidin-1-yl]propan-1-one | 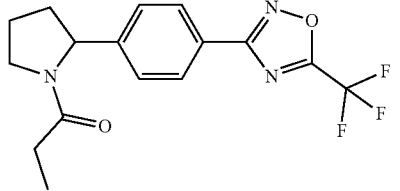 [SMILES: CCC(=O)N1CCCC1c1ccc(-c2noc(C(F)(F)F)n2)cc1] | 1.06 | 340 | A | |
| A-38 | 1-[2-[4-[5-(trifluoromethyl)-1,2,4-oxadiazol-3-yl]phenyl]pyrrolidin-1-yl]ethanone | 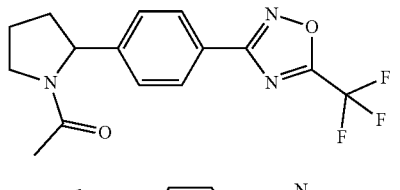 | 1.00 | 326 | A | |
| A-39 | tert-butyl 2-[4-[5-(trifluoromethyl)-1,2,4-oxadiazol-3-yl]phenyl]pyrrolidine-1-carboxylate | 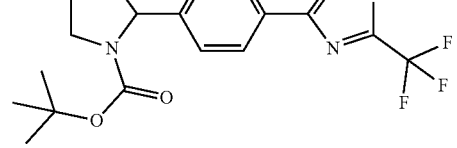 | 1.24 | 384 | A | |
| A-40 | 4-cyano-N-methoxy-N,1,3-trimethyl-5-oxo-2-[4-[5-(trifluoromethyl)-1,2,4-oxadiazol-3-yl]phenyl]pyrrole-2-carboxamide | 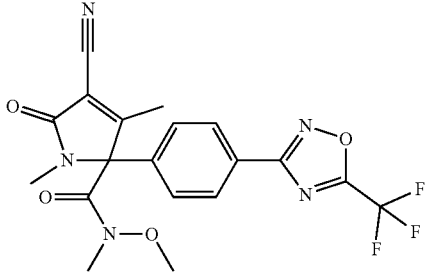 [SMILES: CON(C)C(=O)C1(c2ccc(-c3noc(C(F)(F)F)n3)cc2)C(C)=C(C#N)C(=O)N1C] | 1.02 | 436 | A | |
| A-41 | methyl 4-cyano-1,3-dimethyl-5-oxo-2-[4-[5-(trifluoromethyl)-1,2,4-oxadiazol-3-yl]phenyl]pyrrole-2-carboxylate | 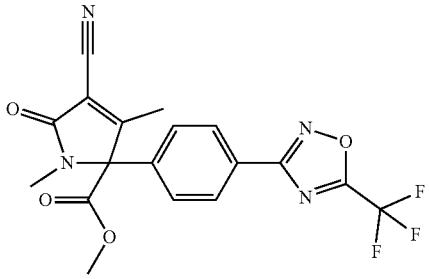 [SMILES: COC(=O)C1(c2ccc(-c3noc(C(F)(F)F)n3)cc2)C(C)=C(C#N)C(=O)N1C] | 1.05 | 407 | A | |
| A-42 | 3-[4-(5-(4-methoxyphenyl)-4,5-dihydroisoxazol-3-yl]phenyl]-5-(trifluoromethyl)-1,2,4-oxadiazole | 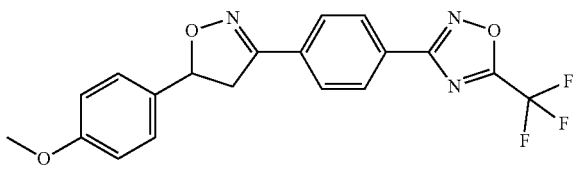 [SMILES: COc1ccc(C2CC(c3ccc(-c4noc(C(F)(F)F)n4)cc3)=NO2)cc1] | 1.96 | 390 | B | |

TABLE A-continued

Melting point (mp) and/or LC/MS data for compounds of Formula (I):

| Entry | Compound Name | Structure | $t_R$ (min) | [M + H]+ (measured) | method | mp (° C) |
|---|---|---|---|---|---|---|
| A-43 | 3-[4-[5-(trifluoromethyl)-1,2,4-oxadiazol-3-yl]phenyl]-1-oxa-2-azaspiro[4,4]non-2-ene | 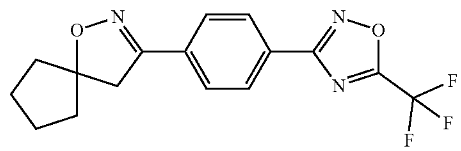 [SMILES: FC(F)(F)c1nc(-c2ccc(C3=NOC4(CCCC4)C3)cc2)no1] | 2.01 | 338 | B | |
| A-44 | 3-[4-(5-methyl-5-phenyl-4H-isoxazol-3-yl)phenyl]-5-(trifluoromethyl)-1,2,4-oxadiazole | 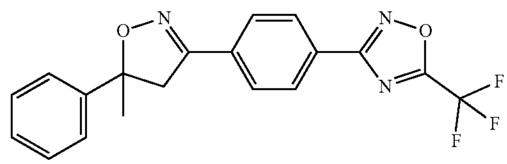 [SMILES: CC1(c2ccccc2)CC(c2ccc(-c3noc(C(F)(F)F)n3)cc2)=NO1] | 2.08 | 374 | B | |
| A-45 | 3-[4-(5-phenyl-4,5-dihydroisoxazol-3-yl)phenyl]-5-(trifluoromethyl)-1,2,4-oxadiazole | 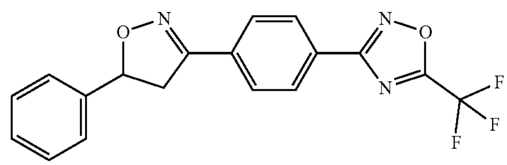 [SMILES: FC(F)(F)c1nc(-c2ccc(C3=NOC(c4ccccc4)C3)cc2)no1] | 1.99 | 360 | B | |
| A-46 | 3-[4-[5-(3-fluorophenyl)-4,5-dihydroisoxazol-3-yl]phenyl]-5-(trifluoromethyl)-1,2,4-oxadiazole | 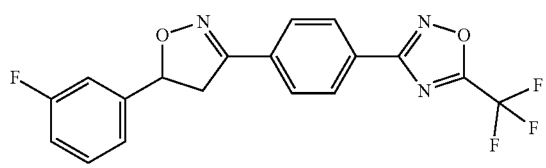 [SMILES: Fc1cccc(C2CC(c3ccc(-c4noc(C(F)(F)F)n4)cc3)=NO2)c1] | 2.00 | 378 | B | |
| A-47 | 3-[4-(5-(4-fluorophenyl)-4,5-dihydroisoxazol-3-yl]phenyl]-5-(trifluoromethyl)-1,2,4-oxadiazole | 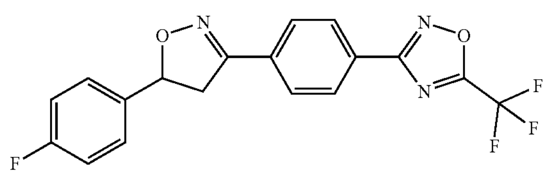 [SMILES: Fc1ccc(C2CC(c3ccc(-c4noc(C(F)(F)F)n4)cc3)=NO2)cc1] | 1.99 | 378 | B | |
| A-48 | 3-[4-[5-(2-methoxyphenyl)-4,5-dihydroisoxazol-3-yl]phenyl]-5-(trifluoromethyl)-1,2,4-oxadiazole | 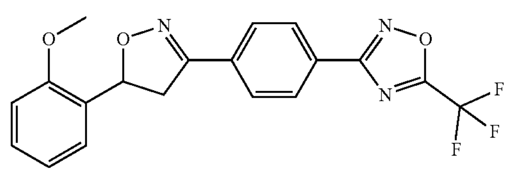 [SMILES: COc1ccccc1C1CC(c2ccc(-c3noc(C(F)(F)F)n3)cc2)=NO1] | 2.06 | 390 | B | |
| A-49 | 3-[4-[3-(4-pyridyl)-4,5-dihydroisoxazol-5-yl]phenyl]-5-(trifluoromethyl)-1,2,4-oxadiazole | 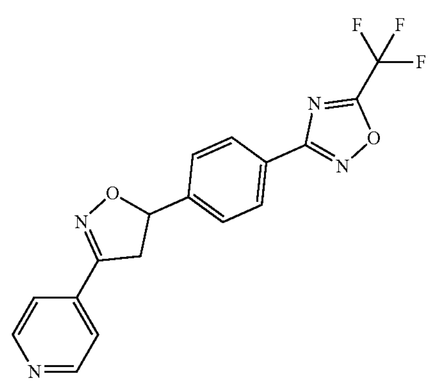 [SMILES: FC(F)(F)c1nc(-c2ccc(C3CC(c4ccncc4)=NO3)cc2)no1] | 1.01 | 361 | A | |

TABLE A-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| A-50 | 3-[4-(3-phenyl-4,5-dihydroisoxazol-5-yl)phenyl]-5-(trifluoromethyl)-1,2,4-oxadiazole | 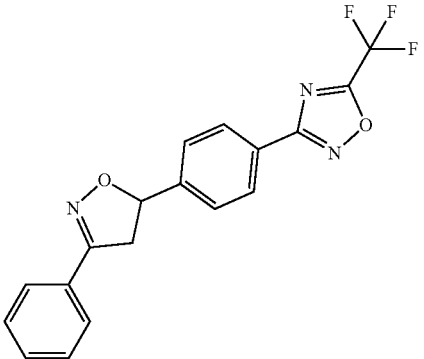 [SMILES: FC(F)(F)c1nc(-c2ccc(C3CC(c4ccccc4)=NO3)cc2)no1] | | | | 139-142 |
| A-51 | 2-[3-fluoro-4-[5-(trifluoromethyl)-1,2,4-oxadiazol-3-yl]phenyl]-5,5-dimethyl-1,3-oxazinan-4-one | 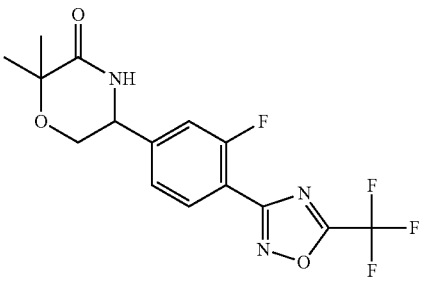 [SMILES: CC1(C)OCC(c2ccc(-c3noc(C(F)(F)F)n3)c(F)c2)NC1=O] | | | | 153-157 |

TABLE B

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| B-1 | 2-[4-[5-(trifluoromethyl)-1,2,4-oxadiazol-3-yl]phenyl]oxazinane | 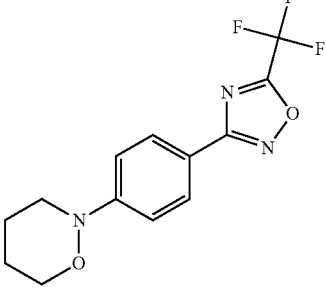 | | | | 94-96 |

TABLE C

Melting point (mp) and/or LC/MS data for compounds of Formula (I):

| Entry | Compound Name | Structure | $t_R$ (min) | [M + H]⁺ (measured) | method | mp (° C) |
|---|---|---|---|---|---|---|
| C-1 | [2-[4-[5-(trifluoromethyl)-1,2,4-oxadiazol-3-yl]phenyl]oxazol-5-yl]methyl acetate | 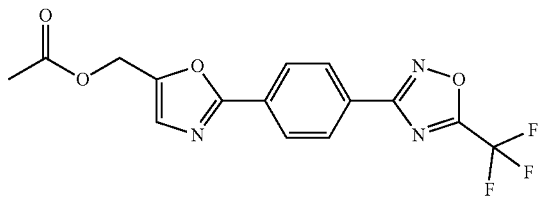 [SMILES: CC(=O)OCc1cnc(-c2ccc(-c3noc(C(F)(F)F)n3)cc2)o1] | | | | 69-71 |
| C-2 | 3-[4-(5-methyloxazol-2-yl)phenyl]-5-(trifluoromethyl)-1,2,4-oxadiazole | 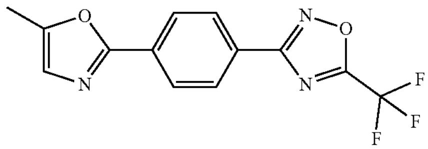 [SMILES: Cc1cnc(-c2ccc(-c3noc(C(F)(F)F)n3)cc2)o1] | | | | 110-111 |
| C-3 | 3-(4-oxazol-2-ylphenyl)-5-(trifluoromethyl)-1,2,4-oxadiazole | 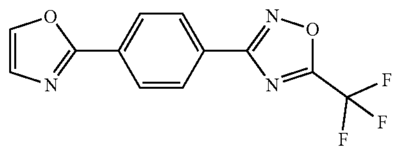 [SMILES: FC(F)(F)c1nc(-c2ccc(-c3ncco3)cc2)no1] | | | | 94-97 |
| C-4 | 3-[4-[4-(chloromethyl)oxazol-2-yl]phenyl]-5-(trifluoromethyl)-1,2,4-oxadiazole | 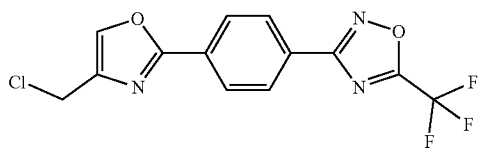 [SMILES: FC(F)(F)c1nc(-c2ccc(-c3nc(CCl)co3)cc2)no1] | | | | 106-107 |
| C-5 | 3-[4-[5-(ethoxymethyl)isoxaizol-3-yl]phenyl]-5-(trifluoromethyl)-1,2,4-oxadiazole | 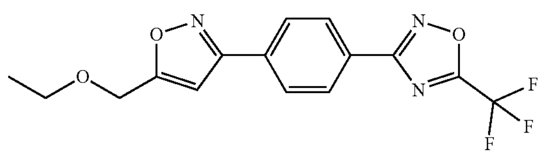 [SMILES: CCOCc1cc(-c2ccc(-c3noc(C(F)(F)F)n3)cc2)no1] | 1.92 | 340.3 | B | |
| C-6 | methyl 3-[4-[5-(trifluoromethyl)-1,2,4-oxadiazol-3-yl]phenyl]isoxazole-5-carboxylate | 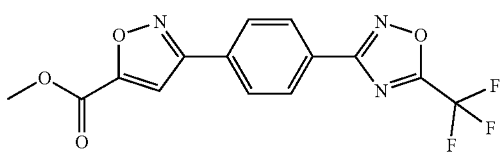 [SMILES: COC(=O)c1cc(-c2ccc(-c3noc(C(F)(F)F)n3)cc2)no1] | 1.83 | 340.2 | B | |
| C-7 | 3-[4-(5-cyclopropylisoxazol-3-yl)phenyl]-5-(trifluoromethyl)-1,2,4-oxadiazole | 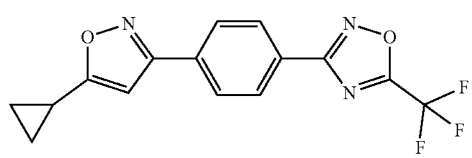 [SMILES: FC(F)(F)c1nc(-c2ccc(-c3cc(C4CC4)on3)cc2)no1] | 1.98 | 322.2 | B | |
| C-8 | 3-[4-(4-methylthiazol-2-yl)phenyl]-5-(trifluoromethyl)-1,2,4-oxadiazole | 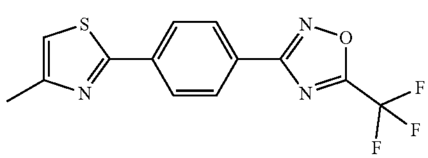 [SMILES: Cc1csc(-c2ccc(-c3noc(C(F)(F)F)n3)cc2)n1] | | | | 89-90 |
| C-9 | 3-[4-[4-(chloromethyl)thiazol-2-yl]phenyl]-5-(trifluoromethyl)-1,2,4-oxadiazole | 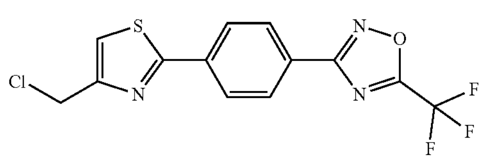 [SMILES: FC(F)(F)c1nc(-c2ccc(-c3nc(CCl)cs3)cc2)no1] | | | | 91-92 |

TABLE C-continued

Melting point (mp) and/or LC/MS data for compounds of Formula (I):

| Entry | Compound Name | Structure | $t_R$ (min) | [M + H]+ (measured) | method | mp (° C) |
|---|---|---|---|---|---|---|
| C-10 | 3-[4-(3-cyclopropylisoxazol-5-yl)phenyl]-5-(trifluoromethyl)-1,2,4-oxadiazole | 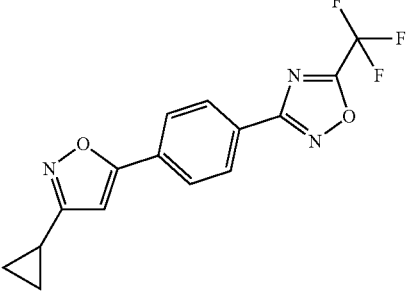 | | | | 143-146 |
| C-11 | 3-[4-(3-methylisoxazol-5-yl)phenyl]-5-(trifluoromethyl)-1,2,4-oxadiazole | 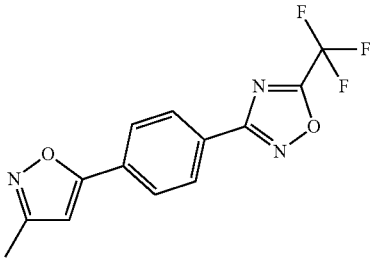 [SMILES: Cc1cc(-c2ccc(-c3noc(C(F)(F)F)n3)cc2)on1] | 1.12 | 296 | A | |
| C-12 | 3-[4-[4-(3-pyridyl)thiazol-2-yl]phenyl]-5-(trifluoromethyl)-1,2,4-oxadiazole | 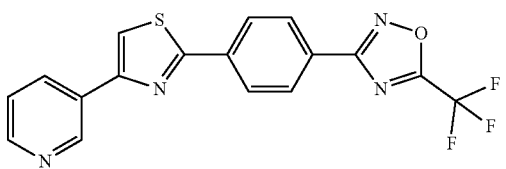 [SMILES: FC(F)(F)c1nc(-c2ccc(-c3nc(-c4cccnc4)cs3)cc2)no1] | | | | 142-143 |
| C-13 | 3-[4-(3-phenylthiazol-2-yl)phenyl]-5-(trifluoromethyl)-1,2,4-oxadiazole | 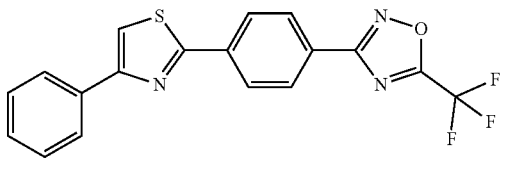 [SMILES: FC(F)(F)c1nc(-c2ccc(-c3nc(-c4ccccc4)cs3)cc2)no1] | | | | 150-151 |
| C-14 | 3-[4-(3-phenylisoxazol-3-yl)phenyl]-5-(trifluoromethyl)-1,2,4-oxadiazole | 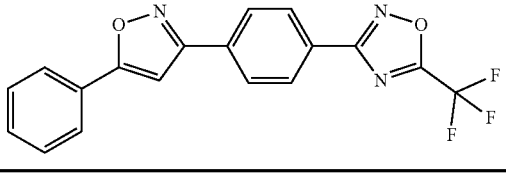 | 2.19 | 358 | B | |

TABLE D

Melting point (mp) and/or LC/MS data for compounds of Formula (I):

| Entry | Compound Name | Structure | $t_R$ (min) | [M + H]+ (measured) | method | mp (° C) |
|---|---|---|---|---|---|---|
| D-1 | 1-ethyl-3-[6-[4-[5-(trifluoromethyl)-1,2,4-oxadiazol-3-yl]phenyl]-2-pyridyl]urea | 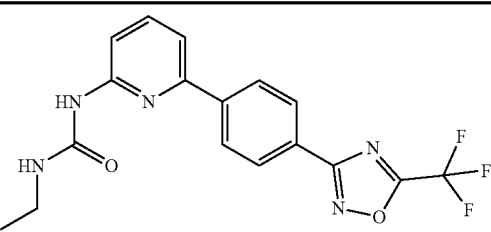 | | | | 200-205 |

TABLE D-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| D-2 | 1-ethyl-3-[5-[4-[5-(trifluoromethyl)-1,2,4-oxadiazol-3-yl]phenyl]-2-pyridyl]urea | 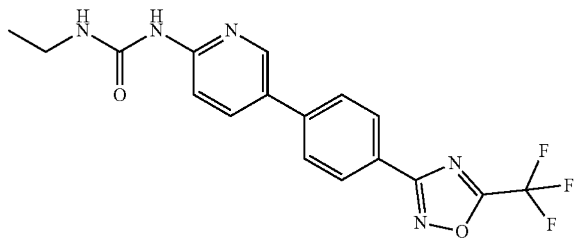 [SMILES: CCNC(=O)Nc1ccc(-c2ccc(-c3noc(C(F)(F)F)n3)cc2)cn1] | | | | 190-195 |
| D-3 | 1-ethyl-3-[4-[4-[5-(trifluoromethyl)-1,2,4-oxadiazol-3-yl]phenyl]-2-pyridyl]urea | 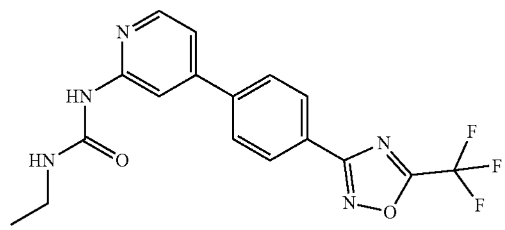 [SMILES: CCNC(=O)Nc1cc(-c2ccc(-c3noc(C(F)(F)F)n3)cc2)ccn1] | | | | 180-185 |
| D-4 | 2,2,2-trifluoro-N-[6-[4-[5-(trifluoromethyl)-1,2,4-oxadiazol-3-yl]phenyl]-2-pyridyl]acetamide | 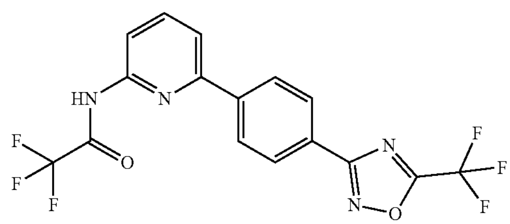 [SMILES: O=C(Nc1cccc(-c2ccc(-c3noc(C(F)(F)F)n3)cc2)n1)C(F)(F)F] | | | | 125-130 |
| D-5 | 3-[4-(6-fluoro-2-pyridyl)phenyl]-5-(trifluoromethyl)-1,2,4-oxadiazole | 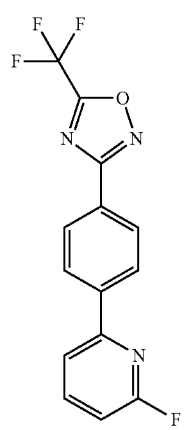 [SMILES: Fc1cccc(-c2ccc(-c3noc(C(F)(F)F)n3)cc2)n1] | | | | 75-80 |
| D-6 | 3-[4-(6-fluoro-3-pyridyl)phenyl]-5-(trifluoromethyl)-1,2,4-oxadiazole | 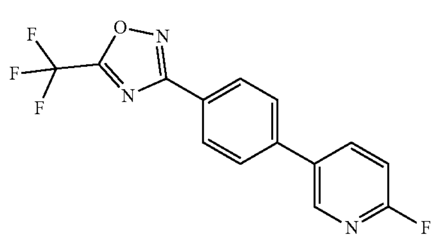 [SMILES: Fc1ccc(-c2ccc(-c3noc(C(F)(F)F)n3)cc2)cn1] | | | | 75-80 |

TABLE D-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| D-7 | 3-[4-(2-fluoro-4-pyridyl)phenyl]-5-(trifluoromethyl)-1,2,4-oxadiazole | 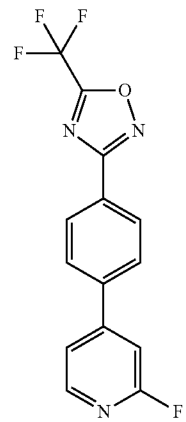 [SMILES: Fc1cc(-c2ccc(-c3noc(C(F)(F)F)n3)cc2)ccn1] | | | | 105-110 |
| D-8 | N-ethyl-6-[4-[5-(trifluoromethyl)-1,2,4-oxadiazol-3-yl]phenyl]pyridin-2-amine | 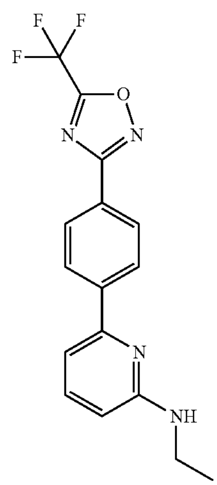 [SMILES: CCNc1cccc(-c2ccc(-c3noc(C(F)(F)F)n3)cc2)n1] | | | | 120-125 |
| D-9 | N-ethyl-4-[4-[5-(trifluoromethyl)-1,2,4-oxadiazol-3-yl]phenyl]pyridin-2-amine | 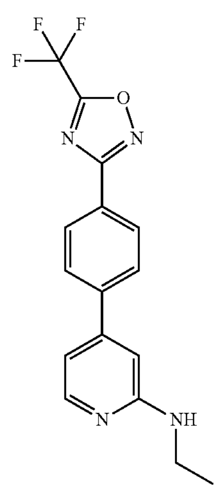 [SMILES: CCNc1cc(-c2ccc(-c3noc(C(F)(F)F)n3)cc2)ccn1] | | | | 130-135 |

TABLE D-continued

Melting point (mp) and/or LC/MS data for compounds of Formula (I):

| Entry | Compound Name | Structure | $t_R$ (min) | [M + H]+ (measured) | method | mp (° C) |
|---|---|---|---|---|---|---|
| D-10 | N-(cyclopropanecarbonyl)-N-[5-[4-[5-(trifluoromethyl)-1,2,4-oxadiazol-3-yl]phenyl]-2-pyridyl]cyclopropane carboxamide | 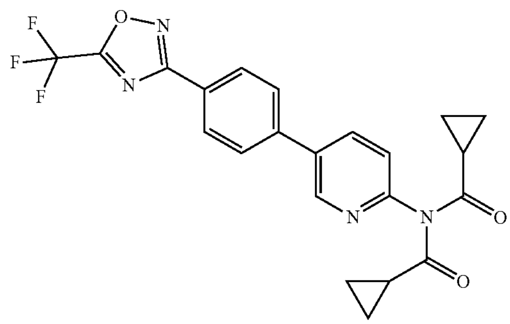 [SMILES: O=C(C1CC1)N(C(=O)C1CC1)c1ccc(-c2ccc(-c3noc(C(F)(F)F)n3)cc2)cn1] | | | | 150-155 |
| D-11 | N-[5-[4-[5-(trifluoromethyl)-1,2,4-oxadiazol-3-yl]phenyl]-2-pyridyl]cyclopropane carboxamide | 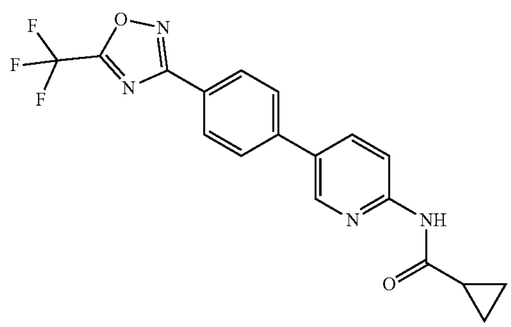 [SMILES: O=C(Nc1ccc(-c2ccc(-c3noc(C(F)(F)F)n3)cc2)cn1)C1CC1] | | | | 175-180 |
| D-12 | 5-[4-[5-(trifluoromethyl)-1,2,4-oxadiazol-3-yl]phenyl]pyridin-2-amine | 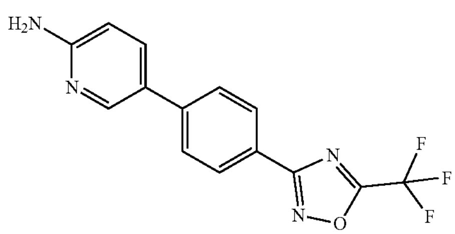 [SMILES: Nc1ccc(-c2ccc(-c3noc(C(F)(F)F)n3)cc2)cn1] | | | | 155-160 |
| D-13 | 2,2,2-trifluoro-N-[5-[4-[5-(trifluoromethyl)-1,2,4-oxadiazol-3-yl]phenyl]-2-pyridyl]acetamide | 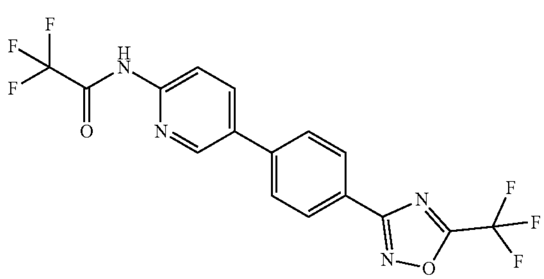 [SMILES: O=C(Nc1ccc(-c2ccc(-c3noc(C(F)(F)F)n3)cc2)cn1)C(F)(F)F] | | | | 135-140 |
| D-14 | N-[6-[4-[5-(trifluoromethyl)-1,2,4-oxadiazol-3-yl]phenyl]-2-pyridyl]cyclopropane carboxamide | 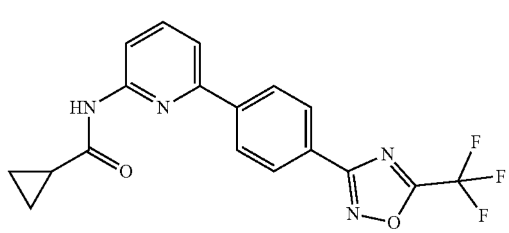 [SMILES: O=C(Nc1cccc(-c2ccc(-c3noc(C(F)(F)F)n3)cc2)n1)C1CC1] | | | | 125-130 |

TABLE D-continued

Melting point (mp) and/or LC/MS data for compounds of Formula (I):

| Entry | Compound Name | Structure | $t_R$ (min) | [M + H]⁺ (measured) | method | mp (° C) |
|---|---|---|---|---|---|---|
| D-15 | 6-[4-[5-(trifluoromethyl)-1,2,4-oxadiazol-3-yl]phenyl]pyridin-2-amine | 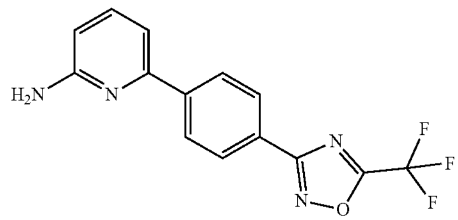 [SMILES: Nc1cccc(-c2ccc(-c3noc(C(F)(F)F)n3)cc2)n1] | | | | 135-140 |
| D-16 | N-(cyclopropanecarbonyl)-N-[4-[4-[5-(trifluoromethyl)-1,2,4-oxadiazol-3-yl]phenyl]-2-pyridyl]cyclopropane carboxamide | 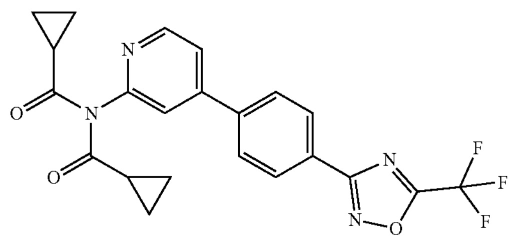 [SMILES: O=C(C1CC1)N(C(=O)C1CC1)c1cc(-c2ccc(-c3noc(C(F)(F)F)n3)cc2)ccn1] | | | | 120-125 |
| D-17 | N-[4-[4-(5-(trifluoromethyl)-1,2,4-oxadiazol-3-yl]phenyl]-2-pyridyl]cyclopropane carboxamide | 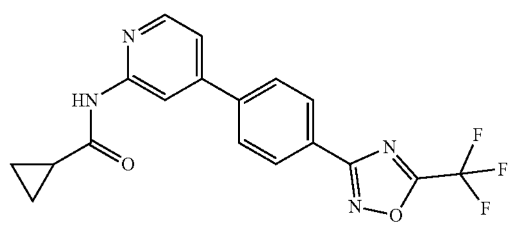 [SMILES: O=C(Nc1cc(-c2ccc(-c3noc(C(F)(F)F)n3)cc2)ccn1)C1CC1] | | | | 140-145 |
| D-18 | 4-[4-[5-(trifluoromethyl)-1,2,4-oxadiazol-3-yl]phenyl]pyridin-2-amine | 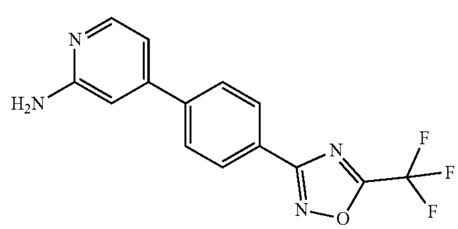 [SMILES: Nc1cc(-c2ccc(-c3noc(C(F)(F)F)n3)cc2)ccn1] | | | | 195-200 |
| D-19 | 2,2,2-trifluoro-N-[4-[4-[5-(trifluoromethyl)-1,2,4-oxadiazol-3-yl]phenyl]-2-pyridyl]acetamide | 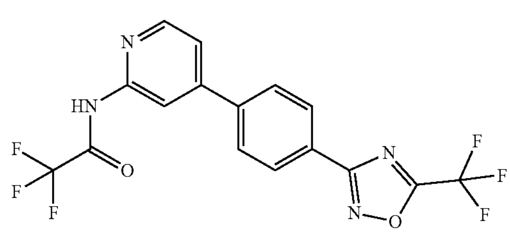 [SMILES: O=C(Nc1cc(-c2ccc(-c3noc(C(F)(F)F)n3)cc2)ccn1)C(F)(F)F] | | | | 230-235 |
| D-20 | N-ethyl-5-[4-[5-(trifluoromethyl)-1,2,4-oxadiazol-3-yl]phenyl]pyridin-2-amine | 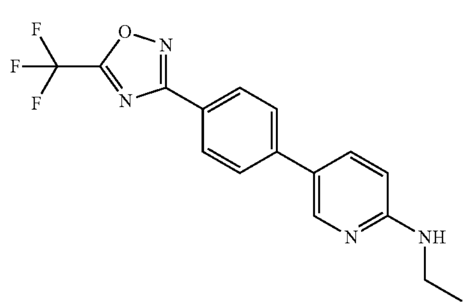 [SMILES: CCNc1ccc(-c2ccc(-c3noc(C(F)(F)F)n3)cc2)cn1] | | | | 120-125 |

TABLE D-continued

Melting point (mp) and/or LC/MS data for compounds of Formula (I):

| Entry | Compound Name | Structure | t_R (min) | [M + H]+ (measured) | method | mp (° C) |
|---|---|---|---|---|---|---|
| D-21 | N-cyclopropyl-5-[4-[5-(trifluoromethyl)-1,2,4-oxadiazol-3-yl]phenyl]pyridin-2-amine | 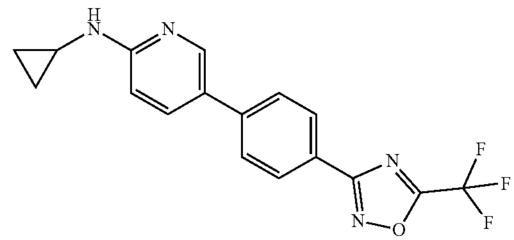 [SMILES: FC(F)(F)c1nc(-c2ccc(-c3ccc(NC4CC4)nc3)cc2)no1] | | | | 135-140 |
| D-22 | 3-[4-(6-chloro-2-pyridyl)phenyl]-5-(trifluoromethyl)-1,2,4-oxadiazole | 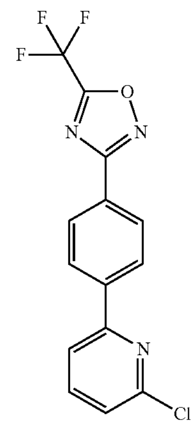 [SMILES: FC(F)(F)c1nc(-c2ccc(-c3cccc(Cl)n3)cc2)no1] | | | | 115-120 |
| D-23 | 4-[5-[4-[5-(trifluoromethyl)-1,2,4-oxadiazol-3-yl]phenyl]-2-pyridyl]morpholine | 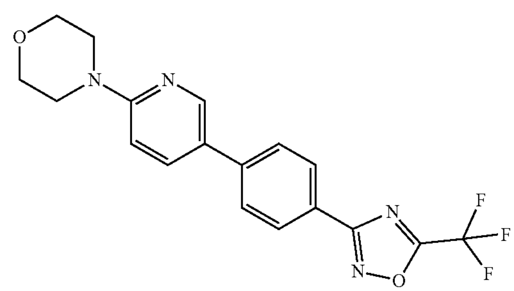 [SMILES: FC(F)(F)c1nc(-c2ccc(-c3ccc(N4CCOCC4)nc3)cc2)no1] | | | | 150-155 |
| D-24 | 4-[6-[4-[5-(trifluoromethyl)-1,2,4-oxadiazol-3-yl]phenyl]-2-pyridyl]morpholine | 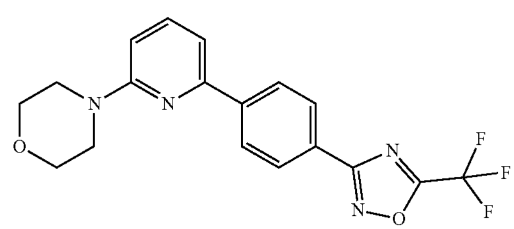 [SMILES: FC(F)(F)c1nc(-c2ccc(-c3cccc(N4CCOCC4)n3)cc2)no1] | | | | 100-105 |
| D-25 | 4-[4-[4-[5-(trifluoromethyl)-1,2,4-oxadiazol-3-yl]phenyl]-2-pyridyl]morpholine | 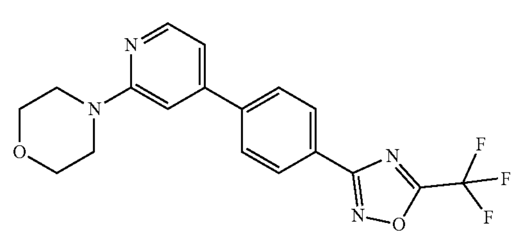 [SMILES: FC(F)(F)c1nc(-c2ccc(-c3ccnc(N4CCOCC4)c3)cc2)no1] | | | | 95-100 |

TABLE D-continued

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| D-26 | 3-[4-(2-chloro-4-pyridyl)phenyl]-5-(trifluoromethyl)-1,2,4-oxadiazole | 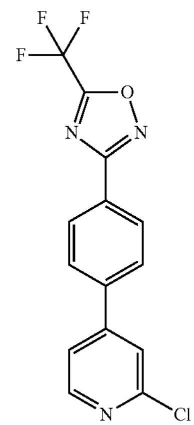 [SMILES: FC(F)(F)c1nc(-c2ccc(-c3ccnc(Cl)c3)cc2)no1] | | | | 110-115 |
| D-27 | 3-[4-(6-chloro-3-pyridyl)phenyl]-5-(trifluoromethyl)-1,2,4-oxadiazole | 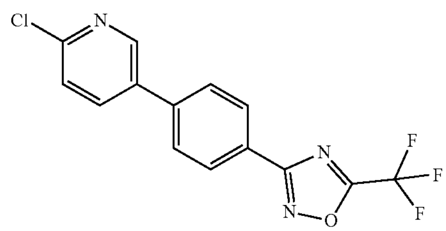 [SMILES: FC(F)(F)c1nc(-c2ccc(-c3ccc(Cl)nc3)cc2)no1] | | | | 140-145 |

TABLE E

Melting point (mp) and/or LC/MS data for compounds of Formula (I):

| Entry | Compound Name | Structure | $t_R$ (min) | $[M + H]^+$ (measured) | method | mp (° C) |
|---|---|---|---|---|---|---|
| E-1 | 3-[4-(3,5-dimethylpyrazol-1-yl)phenyl]-5-(trifluoromethyl)-1,2,4-oxadiazole | 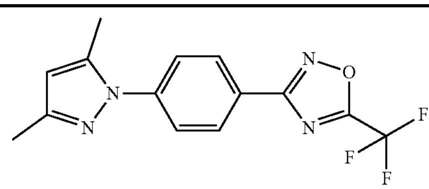 | 1.12 | 309.4 | A | |

BIOLOGICAL EXAMPLES

General Examples of Leaf Disk Tests in Well Plates:

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/ml) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates:

*Mycelia* fragments or conidia suspensions of a fungus, prepared either freshly from liquid cultures of the fungus or from cryogenic storage, are directly mixed into nutrient broth. DMSO solutions of the test compound (max. 10 mg/ml) is diluted with 0.025% Tween20 by a factor of 50 and 10 µl of this solution is pipetted into a microtiter plate (96-well format). The nutrient broth containing the fungal spores/*mycelia* fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Example 1: Fungicidal Activity Against *Glomerella lagenarium* (*Colletotrichum lagenarium*) Liquid Culture/Cucumber/Preventative (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds gave at least 80% control of *Glomerella lagenarium* at 20 ppm when compared to untreated control under the same conditions, which showed extensive disease development:

A-1, A-2, A-4, A-5, A-6, A-7, A-8, A-9, A-10, A-11, A-12, A-13, A-14, A-21, A-22, A-23, A-24, A-25, A-26, A-28, A-29, A-30, A-31, A-32, A-33, A-35, A-36, A-37, A-38, A-41, A-48, A-49, A-51, C-4, C-8, C-9, D-4, D-5, D-6, D-7, D-8, D-12, D-13, D-15, D-19, D-25, D-26, E-1.

Example 2: Fungicidal Activity Against *Phakopsora pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12-14 days after application).

The following compounds gave at least 80% control of *Phakopsora pachyrhizi* at 200 ppm when compared to untreated control under the same conditions, which showed extensive disease development:
A-1, A-3, A-4, A-5, A-6, A-9, A-10, A-12, A-21, A-28, A-29, A-36, C-1, C-2, C-4, C-5, D-12, D-26.

Example 3: Fungicidal Activity Against *Puccinia recondita* f. sp. *Tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates are stored in darkness at 19° C. and 75% rh. The formulated test compound diluted in water is applied 1 day after inoculation. The leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (6-8 days after application).

The following compounds gave at least 80% control of *Puccinia recondita* f. sp. *tritici* at 200 ppm when compared to untreated control under the same conditions, which showed extensive disease development:
A-1, A-2, A-3, A-4, A-5, A-6, A-9, A-11, A-13, A-21, A-22, A-24, A-26, A-28, A-29, A-30, A-31, A-32, A-33, A-35, A-36, A-37, A-38, A-51, C-1, C-2, C-3, C-8, C-11, D-6, D-7, D-26, E-1.

Example 4: Fungicidal Activity Against *Puccinia recondita* f. sp. *tritici*/Wheat/Leaf Disc Preventative (Brown Rust)

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

The following compounds gave at least 80% control of *Puccinia recondita* f. sp. *tritici* at 200 ppm when compared to untreated control under the same conditions, which showed extensive disease development:
A-1, A-2, A-3, A-4, A-5, A-6, A-8, A-9, A-10, A-11, A-12, A-13, A-21, A-23, A-24, A-25, A-26, A-28, A-29, A-30, A-31, A-33, A-34, A-35, A-38, A-51, C-1, C-2, C-3, C-9, C-11, D-6, D-7, D-12, D-15, D-19, D-26, E-1.

The invention claimed is:
1. A compound of formula (I):

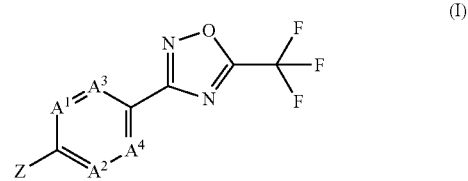

wherein
$A^1$ represents N or $CR^1$, wherein $R^1$ represents hydrogen, halogen, methyl, ethyl, difluoromethyl, trifluoromethyl, methoxy, ethoxy or difluoromethoxy;
$A^2$ represents N or $CR^2$, wherein $R^2$ represents hydrogen, halogen, methyl, ethyl, difluoromethyl, trifluoromethyl, methoxy, ethoxy or difluoromethoxy;
$A^3$ represents N or $CR^3$, wherein $R^3$ represents hydrogen or halogen;
$A^4$ represents N or $CR^4$, wherein $R^4$ represents hydrogen or halogen; and
wherein 0, 1 or 2 of $A^1$, $A^2$, $A^3$ and $A^4$ are N;
Z is selected from $Z^1$, $Z^2$, $Z^3$, $Z^4$ or $Z^5$; wherein
$Z^1$ represents a 5- or 6-membered non-aromatic heterocycle containing 1 ring nitrogen, wherein, optionally:
(i) the heterocycle ring further comprises 1 or 2 groups independently selected from N, $NR^5$, C(O) and $S(O)_2$ or 1 group selected from O or S; (ii) the heterocycle ring is 5-membered and further comprises 1 group selected from N, $NR^5$, C(O) and $S(O)_2$ and 1 group selected from O or S; (iii) the heterocycle ring is 6-membered and further comprises 1 or 2 groups independently selected from N, $NR^5$, C(O) and $S(O)_2$ and 1 group selected from O or S; or (iv) the heterocycle ring further comprises 1 group which is C(O) and 2 groups independently selected from N and $NR^5$; and wherein the heterocycle ring is optionally substituted by 1, 2 or 3 substituents, which may be the same or different, selected from $R^9$, or a single substituent selected from $R^{11}$, and wherein the 5- or 6-membered non-aromatic heterocycle is bound to the rest of the molecule by a carbon-carbon bond through a ring carbon;

$Z^2$ represents a 5- or 6-membered non-aromatic heterocycle containing 1 ring nitrogen, wherein optionally: (i) the heterocycle ring further comprises 1 or 2 groups independently selected from C(O) and S(O)$_2$ or 1 group selected from O or S; or (ii) the heterocycle ring further comprises 1 or 2 groups independently selected from C(O) and S(O)$_2$ and 1 group selected from O or S; and wherein when the heterocycle ring is 5-membered it is optionally substituted by 1 or 2 substituents, which may be the same or different, selected from $R^{10}$, or a single substituent selected from $R^{11}$, and wherein when the heterocycle ring is 6-membered it is optionally substituted by 1, 2 or 3 substituents, which may be the same or different, selected from $R^{10}$, or a single substituent selected from $R^{11}$, and wherein a position α to the ring nitrogen is not C(O) or S(O)$_2$, and the heterocycle ring is bound to the rest of the molecule by a nitrogen-carbon bond through the ring nitrogen;

$Z^3$ represents a 5-membered heteroaryl containing 1 ring nitrogen, wherein optionally the heteroaryl ring further comprises 1 or 2 groups independently selected from N and $NR^5$, and is optionally substituted by 1, 2 or 3 substituents, which may be the same or different, selected from $R^{12}$, and wherein the heteroaryl is bound to the rest of the molecule by a carbon-carbon bond through a ring carbon; or $Z^3$ represents a heteroaryl selected from:

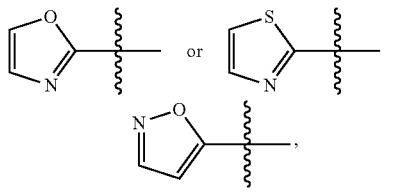

optionally substituted by 1 or 2 substituents, which may be the same or different, selected from $R^{12}$;

$Z^4$ represents a 6-membered heteroaryl containing 1 ring nitrogen, wherein optionally the heteroaryl ring further comprises 1 or 2 additional ring nitrogen atoms, and is optionally substituted by 1, 2 or 3 substituents, which may be the same or different selected from $R^{13}$, and wherein the heteroaryl is bound to the rest of the molecule by a carbon-carbon bond through a ring carbon; and $Z^5$ represents a 5-membered heteroaryl containing 1 ring nitrogen, wherein optionally the heteroaryl ring further comprises 1 or 2 additional ring nitrogen atoms, and is optionally substituted by 1, 2 or 3 substituents, which may be the same or different selected from $R^{13}$, and wherein the heteroaryl is bound to the rest of the molecule by a nitrogen-carbon bond through a ring nitrogen;

$R^5$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^6$, $S(O)_2R^6$, $C(O)OR^7$, $C(O)N(R^7)(R^8)$ or $S(O)_2N(R^7)(R^8)$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano;

$R^6$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl, or $C_{3-6}$cycloalkyl;

$R^7$ represents hydrogen, $C_{1-6}$alkyl, $C_{3-6}$cycloalkyl, $C_{3-6}$cycloalkyl-$C_{1-2}$alkyl, $C_{1-4}$alkoxy-$C_{1-4}$alkyl, wherein $C_{1-6}$alkyl, $C_{3-6}$cycloalkyl, $C_{3-6}$cycloalkyl-$C_{1-2}$-alkyl and $C_{1-4}$alkoxy-$C_{1-4}$alkyl are optionally substituted by halogen or cyano;

$R^8$ represents hydrogen, $C_{1-4}$alkyl, $C_{1-4}$haloalkyl, $C_{1-4}$alkoxy or $C_{1-4}$alkoxy-$C_{1-4}$alkyl, $R^9$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl;

$R^{10}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl;

$R^{11}$ represents a three- to six-membered saturated carbocycle which shares a carbon atom of the heterocycle as defined by $Z^1$ or $Z^2$ to form a spirocycle, and wherein optionally the saturated carbocycle further comprises one group selected from O or S;

$R^{12}$ represents $C_{1-4}$alkyl, $C_{1-4}$haloalkyl, methoxy, ethoxy, iso-propoxy, n-butoxy, sec-butoxy, iso-butoxy, tert-butoxy, $C_{1-4}$alkoxy$C_{1-4}$alkyl, $C_{1-4}$haloalkoxy, $C_{1-4}$alkylcarbonyl, $C_{1-4}$alkoxycarbonyl, $C_{1-4}$alkylcarbonyloxy$C_{1-4}$alkyl, or $C_{3-6}$cycloalkyl; and $R^{13}$ represents cyano, halogen, hydroxy, $C_{1-4}$alkyl, $C_{2-4}$alkenyl, $C_{2-4}$alkynyl, $C_{1-4}$haloalkyl, $C_{2-4}$haloalkenyl, $C_{1-4}$alkoxy, $C_{1-4}$alkoxy$C_{1-4}$alkyl, $C_{1-4}$haloalkoxy, $C_{3-4}$alkenyloxy, $C_{3-4}$alkynyloxy, $C_{1-4}$alkylcarbonyl, $C_{1-4}$alkoxycarbonyl, $C_{1-4}$alkylcarbonylamino, N—$C_{1-4}$alkylaminocarbonyl, N,N-di$C_{1-4}$alkylaminocarbonyl or $C_{3-6}$cycloalkyl; or a salt or N-oxide thereof.

2. A compound according to claim 1, wherein one of $A^1$ to $A^4$ represents C-halogen and three of $A^1$ to $A^4$ represent C—H, or $A^1$ to $A^4$ represent C—H.

3. A compound according to claim 1, wherein $A^1$ to $A^4$ represent C—H, or $A^1$, $A^2$ and $A^4$ represent C—H and $A^3$ is C—F.

4. A compound according to claim 1, wherein Z is $Z^1$.

5. A compound according to claim 1, wherein Z is $Z^2$.

6. A compound according to claim 1, wherein Z is unsubstituted $Z^3$.

7. A compound according to claim 1, wherein Z is $Z^4$.

8. A compound according to claim 1, wherein Z is $Z^5$.

9. A compound according to claim 1, wherein Z is $Z^3$, and $Z^3$ is a heteroaryl selected from:

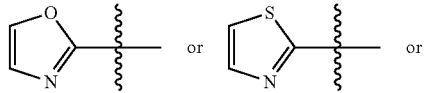

-continued

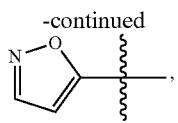

optionally substituted by 1 or 2 substituents, which may be the same or different, selected from $R^{12}$, wherein $R^{12}$ is $C_{1-4}$alkyl, $C_{1-4}$haloalkyl, $C_{1-4}$alkoxy$C_{1-4}$alkyl, $C_{1-4}$alkoxycarbonyl, $C_{1-4}$alkylcarbonyloxy$C_{1-4}$alkyl, or $C_{3-6}$cycloalkyl.

10. An agrochemical composition comprising a fungicidally effective amount of a compound of formula (I) according to claim 1.

11. The composition according to claim 10, further comprising at least one additional active ingredient and/or an agrochemically-acceptable diluent or carrier.

12. An agrochemical composition comprising a fungicidally effective amount of a compound of formula (I) according to claim 2.

13. The composition according to claim 12, further comprising at least one additional active ingredient and/or an agrochemically-acceptable diluent or carrier.

14. An agrochemical composition comprising a fungicidally effective amount of a compound of formula (I) according to claim 3.

15. The composition according to claim 14, further comprising at least one additional active ingredient and/or an agrochemically-acceptable diluent or carrier.

16. An agrochemical composition comprising a fungicidally effective amount of a compound of formula (I) according to claim 9.

17. The composition according to claim 16, further comprising at least one additional active ingredient and/or an agrochemically-acceptable diluent or carrier.

18. A compound of formula (I):

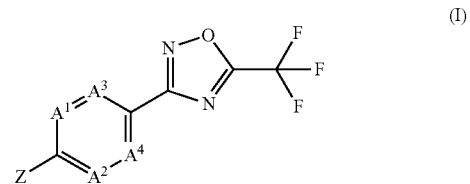

wherein
$A^1$ represents N or $CR^1$, wherein $R^1$ represents hydrogen, halogen, methyl, ethyl, difluoromethyl, trifluoromethyl, methoxy, ethoxy or difluoromethoxy;
$A^2$ represents N or $CR^2$, wherein $R^2$ represents hydrogen, halogen, methyl, ethyl, difluoromethyl, trifluoromethyl, methoxy, ethoxy or difluoromethoxy;
$A^3$ represents N or $CR^3$, wherein $R^3$ represents hydrogen or halogen;
$A^4$ represents N or $CR^4$, wherein $R^4$ represents hydrogen or halogen; and
wherein 0, 1 or 2 of $A^1$, $A^2$, $A^3$ and $A^4$ are N;
$Z^3$ represents a heteroaryl selected from:

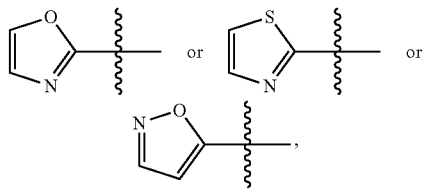

substituted by 1 phenyl or pyridinyl; or
a salt or N-oxide thereof.

19. A compound according to claim 18, wherein one of $A^1$ to $A^4$ represents C-halogen and three of $A^1$ to $A^4$ represent C—H, or $A^1$ to $A^4$ represent C—H.

20. A compound according to claim 18, wherein $A^1$ to $A^4$ represent C—H, or $A^1$, $A^2$ and $A^4$ represent C—H and $A^3$ is C—F.

* * * * *